(12) United States Patent
Kordis et al.

(10) Patent No.: US 9,895,072 B2
(45) Date of Patent: Feb. 20, 2018

(54) BASKET STYLE CARDIAC MAPPING CATHETER HAVING AN ATRAUMATIC, METALLIC TWO-PART DISTAL TIP FOR DETECTION OF CARDIAC RHYTHM DISORDERS

(71) Applicant: Topera, Inc., Scottsdale, AZ (US)

(72) Inventors: Thomas F. Kordis, San Diego, CA (US); Eric T. Johnson, Temecula, CA (US); Phillip C. Burke, Pala, CA (US); Darrin J. Kent, Murrieta, CA (US); Robert Ryan Ragland, Temecula, CA (US)

(73) Assignee: Topera, Inc., Menlo Park, CA (US)

( * ) Notice: Subject to any disclaimer, the term of this patent is extended or adjusted under 35 U.S.C. 154(b) by 861 days.

(21) Appl. No.: 14/247,330

(22) Filed: Apr. 8, 2014

(65) Prior Publication Data
US 2014/0228663 A1    Aug. 14, 2014

Related U.S. Application Data

(63) Continuation of application No. 13/929,838, filed on Jun. 28, 2013, now Pat. No. 9,504,399, which is a
(Continued)

(51) Int. Cl.
*A61B 5/042* (2006.01)
*A61B 5/00* (2006.01)
(Continued)

(52) U.S. Cl.
CPC ............ *A61B 5/0422* (2013.01); *A61B 5/042* (2013.01); *A61B 5/6858* (2013.01);
(Continued)

(58) Field of Classification Search
CPC ............... A61B 5/6858; A61B 5/6859; A61B 2017/00358; A61B 2017/2212;
(Continued)

(56) References Cited

U.S. PATENT DOCUMENTS

| 3,326,207 A | 6/1967 | Egan |
| 3,517,128 A | 6/1970 | Hines |

(Continued)

FOREIGN PATENT DOCUMENTS

| EP | 0689397 B1 | 7/2000 |
| EP | 1190671 B2 | 12/2006 |

(Continued)

OTHER PUBLICATIONS

Examination Report dated Nov. 12, 2014 for Counterpart Australian Application AU 2014202011.
(Continued)

*Primary Examiner* — Lee S Cohen
*Assistant Examiner* — Erin M Cardinal
(74) *Attorney, Agent, or Firm* — Hoffmann & Baron, LLP

(57) ABSTRACT

A system for sensing multiple local electric voltages from endocardial surface of a heart, includes: an elongate tubular member having a lumen, a proximal end and a distal end; a plurality of flexible splines; an anchor for securably affixing the proximal portions of the splines, where the anchor is securably affixed within the lumen of the elongate tubular member at the distal end of the elongate tubular member; and a metallic tip for securably affixing the distal portions of the splines.

19 Claims, 44 Drawing Sheets

Related U.S. Application Data continuation of application No. 13/687,274, filed on Nov. 28, 2012, now Pat. No. 8,504,133, which is a continuation of application No. 13/409,263, filed on Mar. 1, 2012, now Pat. No. 8,346,339.

(60) Provisional application No. 61/555,190, filed on Nov. 3, 2011, provisional application No. 61/478,340, filed on Apr. 22, 2011.

(51) Int. Cl.
 *A61B 18/14* (2006.01)
 *A61B 18/00* (2006.01)

(52) U.S. Cl.
 CPC ........ *A61B 5/6859* (2013.01); *A61B 18/1492* (2013.01); *A61B 2018/0016* (2013.01); *A61B 2018/00267* (2013.01); *A61B 2018/00351* (2013.01); *F04C 2270/0421* (2013.01); *Y10T 29/49117* (2015.01)

(58) Field of Classification Search
 CPC ........ A61B 2018/00267; A61B 17/221; A61B 5/0422; A61B 5/042; A61B 18/1492
 USPC .................... 600/372, 373, 393, 509; 606/41
 See application file for complete search history.

(56) References Cited

U.S. PATENT DOCUMENTS

| | | |
|---|---|---|
| 3,557,794 A | 1/1971 | Van Patten |
| 3,825,015 A | 7/1974 | Berkovits |
| 3,865,118 A | 2/1975 | Bures |
| 3,903,897 A | 9/1975 | Woollons et al. |
| 3,995,623 A | 12/1976 | Blake et al. |
| 4,172,451 A | 10/1979 | Kline |
| 4,254,766 A | 3/1981 | Kordis |
| 4,281,660 A | 8/1981 | Fujiwara |
| 4,289,138 A | 9/1981 | Halvorsen |
| 4,360,031 A | 11/1982 | White |
| 4,522,212 A | 6/1985 | Gelinas et al. |
| 4,555,157 A | 11/1985 | Johnson et al. |
| 4,573,473 A | 3/1986 | Hess |
| 4,628,937 A | 12/1986 | Hess et al. |
| 4,638,802 A | 1/1987 | Okada |
| 4,641,649 A | 2/1987 | Walinsky et al. |
| 4,649,924 A | 3/1987 | Taccardi |
| 4,660,571 A | 4/1987 | Hess et al. |
| 4,664,120 A | 5/1987 | Hess |
| 4,677,990 A | 7/1987 | Neubauer |
| 4,682,596 A | 7/1987 | Bales et al. |
| 4,690,148 A | 9/1987 | Hess |
| 4,699,147 A | 10/1987 | Chilson et al. |
| 4,785,815 A | 11/1988 | Cohen |
| 4,869,248 A | 9/1989 | Narula |
| 4,882,777 A | 11/1989 | Narula |
| 4,920,980 A | 5/1990 | Jackowski |
| 4,922,912 A | 5/1990 | Watanabe |
| 4,940,064 A | 7/1990 | Desai |
| 4,960,134 A | 10/1990 | Webster, Jr. |
| 4,976,710 A | 12/1990 | Mackin |
| 5,010,894 A | 4/1991 | Edhag |
| 5,041,973 A | 8/1991 | Lebron et al. |
| 5,056,517 A | 10/1991 | Fenici |
| 5,057,114 A | 10/1991 | Wittich et al. |
| 5,059,205 A | 10/1991 | El-Nounou et al. |
| 5,078,717 A | 1/1992 | Parins et al. |
| 5,117,828 A | 6/1992 | Metzger et al. |
| 5,156,151 A | 10/1992 | Imran |
| 5,215,103 A | 6/1993 | Desai |
| 5,228,442 A | 7/1993 | Imran |
| 5,231,995 A | 8/1993 | Desai |
| 5,237,996 A | 8/1993 | Waldman et al. |
| 5,239,999 A | 8/1993 | Imran |
| 5,242,462 A | 9/1993 | El-Nounou et al. |
| 5,255,679 A | 10/1993 | Imran |
| 5,263,493 A | 11/1993 | Avitall |
| 5,279,299 A | 1/1994 | Imran |
| 5,293,868 A | 3/1994 | Nardella |
| 5,297,549 A | 3/1994 | Beatty et al. |
| 5,309,910 A | 5/1994 | Edwards et al. |
| 5,313,943 A | 5/1994 | Houser et al. |
| 5,320,214 A | 6/1994 | Kordis |
| 5,324,284 A | 6/1994 | Imran |
| 5,327,889 A | 7/1994 | Imran |
| 5,345,936 A | 9/1994 | Pomeranz et al. |
| 5,365,926 A | 11/1994 | Desai |
| 5,383,917 A | 1/1995 | Desai et al. |
| 5,397,339 A | 3/1995 | Desai |
| 5,400,783 A | 3/1995 | Pomeranz et al. |
| 5,404,638 A | 4/1995 | Imran |
| 5,406,946 A | 4/1995 | Imran |
| 5,409,000 A | 4/1995 | Imran |
| 5,409,008 A | 4/1995 | Svenson et al. |
| 5,411,025 A | 5/1995 | Webster, Jr. |
| 5,425,364 A | 6/1995 | Imran |
| 5,429,131 A | 7/1995 | Scheinman et al. |
| 5,433,198 A | 7/1995 | Desai |
| 5,454,370 A | 10/1995 | Avitall |
| 5,465,717 A | 11/1995 | Imran et al. |
| 5,471,982 A | 12/1995 | Edwards et al. |
| 5,476,495 A | 12/1995 | Kordis et al. |
| 5,482,037 A | 1/1996 | Borghi |
| 5,487,391 A | 1/1996 | Panescu |
| 5,499,981 A | 3/1996 | Kordis |
| 5,500,011 A | 3/1996 | Desai |
| 5,509,419 A | 4/1996 | Edwards et al. |
| 5,549,108 A | 8/1996 | Edwards et al. |
| 5,549,661 A | 8/1996 | Kordis et al. |
| 5,555,883 A | 9/1996 | Avitall |
| 5,558,073 A | 9/1996 | Pomeranz et al. |
| 5,571,164 A | 11/1996 | Ekwall et al. |
| 5,575,810 A | 11/1996 | Swanson et al. |
| 5,578,007 A | 11/1996 | Imran |
| 5,628,313 A | 5/1997 | Webster, Jr. |
| 5,636,634 A | 6/1997 | Kordis et al. |
| 5,647,870 A | 7/1997 | Kordis et al. |
| 5,657,755 A | 8/1997 | Desai |
| 5,662,108 A | 9/1997 | Budd et al. |
| 5,681,308 A | 10/1997 | Edwards et al. |
| 5,687,737 A | 11/1997 | Branham et al. |
| 5,722,401 A | 3/1998 | Pietroski et al. |
| 5,725,525 A | 3/1998 | Kordis |
| 5,730,128 A | 3/1998 | Pomeranz et al. |
| 5,730,704 A | 3/1998 | Avitall |
| 5,757,810 A | 5/1998 | Fall |
| 5,782,239 A | 7/1998 | Webster, Jr. |
| 5,782,899 A | 7/1998 | Imran |
| 5,785,706 A | 7/1998 | Bednarek |
| RE35,880 E | 8/1998 | Waldman et al. |
| 5,819,740 A | 10/1998 | Muhlenberg |
| 5,823,189 A * | 10/1998 | Kordis ................ A61B 5/0422 600/373 |
| 5,836,947 A | 11/1998 | Fleischman et al. |
| 5,846,196 A | 12/1998 | Siekmeyer et al. |
| 5,871,443 A | 2/1999 | Edwards et al. |
| 6,088,614 A | 7/2000 | Swanson |
| 6,119,030 A * | 9/2000 | Morency ................ A61B 5/042 600/374 |
| 6,142,994 A | 11/2000 | Swanson et al. |
| 6,152,920 A | 11/2000 | Thompson et al. |
| 6,165,169 A | 12/2000 | Panescu et al. |
| 6,216,043 B1 * | 4/2001 | Swanson ............... A61B 5/0422 600/374 |
| 6,402,740 B1 | 6/2002 | Ellis et al. |
| 6,542,773 B2 | 4/2003 | Dupree et al. |
| 6,615,073 B1 | 9/2003 | Panescu et al. |
| 6,647,281 B2 | 11/2003 | Morency |
| 6,647,617 B1 | 11/2003 | Beatty et al. |
| 6,788,969 B2 | 9/2004 | Dupree et al. |
| 6,826,420 B1 | 11/2004 | Beatty et al. |
| 6,944,490 B1 | 9/2005 | Chow |
| 7,184,811 B2 | 2/2007 | Phan et al. |
| 7,245,973 B2 | 7/2007 | Liu et al. |

(56) References Cited

U.S. PATENT DOCUMENTS

| | | | |
|---|---|---|---|
| 7,289,843 B2 | 10/2007 | Beatty et al. | |
| 7,306,594 B2 | 12/2007 | Collins et al. | |
| 7,311,704 B2 | 12/2007 | Paul et al. | |
| 7,326,204 B2 | 2/2008 | Paul et al. | |
| 7,326,206 B2 | 2/2008 | Paul et al. | |
| 7,326,208 B2 | 2/2008 | Vanney et al. | |
| 7,331,959 B2 | 2/2008 | Cao et al. | |
| 7,338,436 B1 | 3/2008 | Snell et al. | |
| 7,416,552 B2 | 8/2008 | Paul et al. | |
| 7,419,489 B2 | 9/2008 | Vanney et al. | |
| 7,474,909 B2 | 1/2009 | Phan et al. | |
| 7,504,172 B2 | 3/2009 | Irvine et al. | |
| 7,505,810 B2 | 3/2009 | Harlev et al. | |
| 7,515,954 B2 | 4/2009 | Harlev et al. | |
| 7,526,342 B2 | 4/2009 | Chin et al. | |
| 7,606,609 B2 | 10/2009 | Muranushi et al. | |
| 7,632,265 B2 | 12/2009 | Hauck et al. | |
| RE41,334 E | 5/2010 | Beatty et al. | |
| 7,715,604 B2 | 5/2010 | Sun et al. | |
| 7,729,752 B2 | 6/2010 | Harlev et al. | |
| 7,776,034 B2 | 8/2010 | Kampa | |
| 7,789,877 B2 | 9/2010 | Vanney | |
| 7,819,866 B2 | 10/2010 | Bednarek | |
| 7,824,415 B2 | 11/2010 | Teague et al. | |
| 7,826,881 B1 | 11/2010 | Beatty et al. | |
| 7,857,810 B2 | 12/2010 | Wang et al. | |
| 7,930,018 B2 | 4/2011 | Harlev et al. | |
| 7,953,475 B2 | 5/2011 | Harlev et al. | |
| 8,007,495 B2 | 8/2011 | McDaniel et al. | |
| 8,167,845 B2 | 5/2012 | Wang et al. | |
| 8,224,431 B2 | 7/2012 | Drew | |
| 8,315,709 B2 | 11/2012 | Corndorf | |
| 8,364,235 B2* | 1/2013 | Kordis | A61B 5/0422 600/373 |
| 8,489,171 B2 | 7/2013 | Hauck et al. | |
| 8,560,086 B2 | 10/2013 | Just et al. | |
| 8,588,885 B2 | 11/2013 | Hall et al. | |
| 2001/0001315 A1 | 5/2001 | Bates et al. | |
| 2001/0031981 A1* | 10/2001 | Evans | A61B 17/221 606/200 |
| 2003/0088254 A1* | 5/2003 | Gregory, Jr. | A61B 17/221 606/127 |
| 2006/0015140 A1 | 1/2006 | Tsugita et al. | |
| 2006/0058813 A1* | 3/2006 | Teague | A61B 17/32056 606/113 |
| 2006/0235286 A1* | 10/2006 | Stone | A61B 5/02007 600/381 |
| 2008/0103523 A1 | 5/2008 | Chiu et al. | |
| 2009/0171274 A1 | 7/2009 | Harlev et al. | |
| 2009/0264745 A1 | 10/2009 | Markowitz et al. | |
| 2010/0094274 A1 | 4/2010 | Narayan et al. | |
| 2010/0274150 A1 | 10/2010 | Harlev et al. | |
| 2011/0213231 A1* | 9/2011 | Hall | A61B 5/0422 600/373 |
| 2011/0251505 A1 | 10/2011 | Narayan et al. | |
| 2012/0184858 A1 | 7/2012 | Harlev et al. | |
| 2013/0172715 A1* | 7/2013 | Just | A61B 18/1492 600/374 |
| 2013/0178850 A1 | 7/2013 | Lopes et al. | |
| 2013/0190587 A1 | 7/2013 | Lopes et al. | |
| 2013/0197513 A1 | 8/2013 | Lopes et al. | |
| 2013/0296729 A1 | 11/2013 | Datta | |
| 2013/0304065 A1 | 11/2013 | Lopes et al. | |
| 2013/0345537 A1 | 12/2013 | Thakur et al. | |
| 2014/0018656 A1 | 1/2014 | Hauck et al. | |
| 2014/0025069 A1 | 1/2014 | Willard et al. | |
| 2014/0052120 A1 | 2/2014 | Benscoter et al. | |
| 2014/0088591 A1 | 3/2014 | Just et al. | |
| 2015/0342491 A1* | 12/2015 | Marecki | A61B 18/1492 600/374 |

FOREIGN PATENT DOCUMENTS

| | | |
|---|---|---|
| EP | 2641534 A1 | 9/2013 |
| WO | 2013112844 A2 | 8/2013 |

OTHER PUBLICATIONS

PCT/ISA/206; Invitation to Pay Additional Fees and, Where Applicable, Protest Fee, for PCT/US2012/027183, dated Jun. 5, 2012; including Annex to Form PCT/ISA/206; Communication Relating to the Results of the Partial International Search.

Strohsterne, Apr. 14, 2010, retrieved from the Internet: URL:http://web.archive.org/web/20100414000125/http://www.peppiclip.de/Basteln%20Weihnachten%201/html/strohsterne.html.

Transom Knot, Sep. 19, 2000, retrieved from the Internet: URL:http://web.archive.org/web/20000919183833/http://www.realknots.com/knots/constric.htm#transom.

U.S. Appl. No. 13/217,123 to Carey Robert Briggs et al., filed Aug. 24, 2011.

U.S. Appl. No. 61/481,512 to Sanjiv Narayan et al., filed May 2, 2011.

U.S. Appl. No. 61/481,607 to Carey Robert Briggs et al., filed May 2, 2011.

U.S. Appl. No. 61/569,132 to Sanjiv Narayan et al., filed Dec. 9, 2011.

* cited by examiner

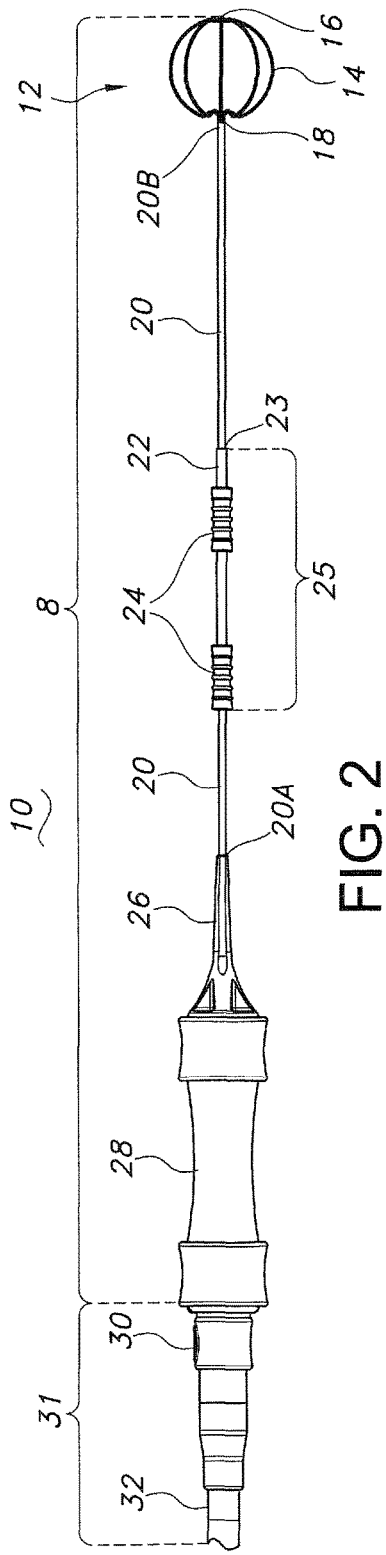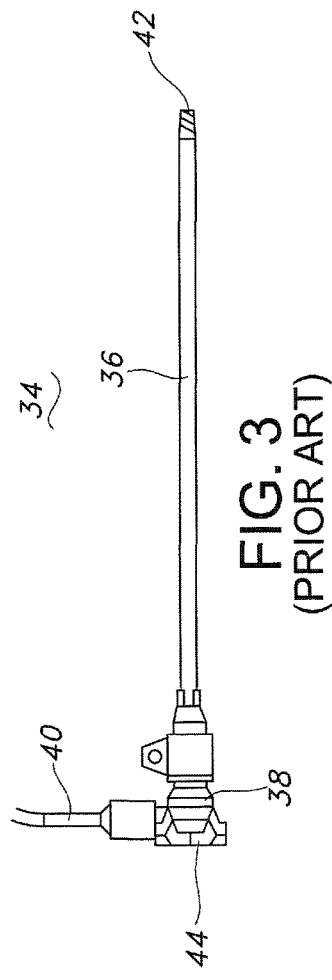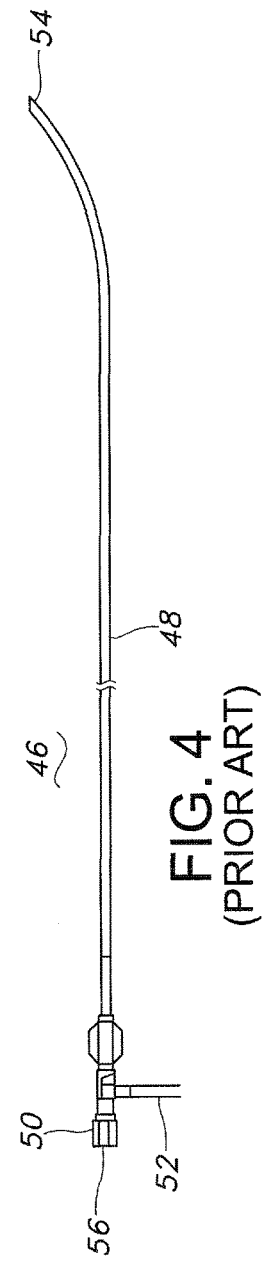
FIG. 2
FIG. 3 (PRIOR ART)
FIG. 4 (PRIOR ART)

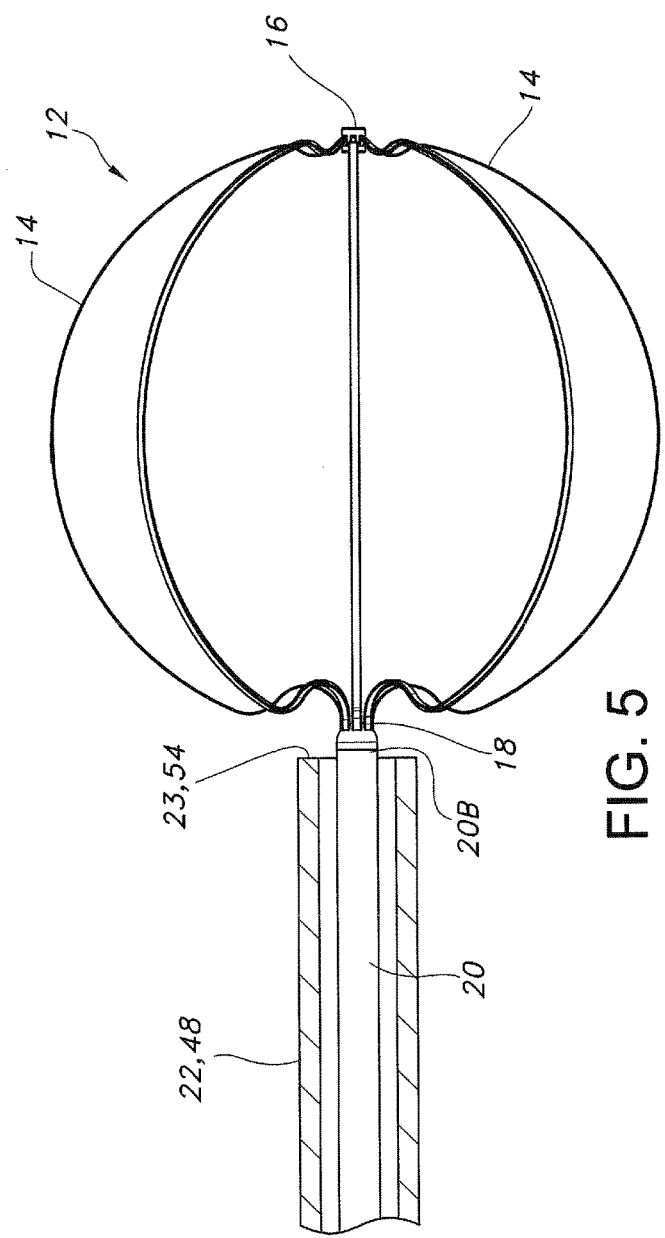
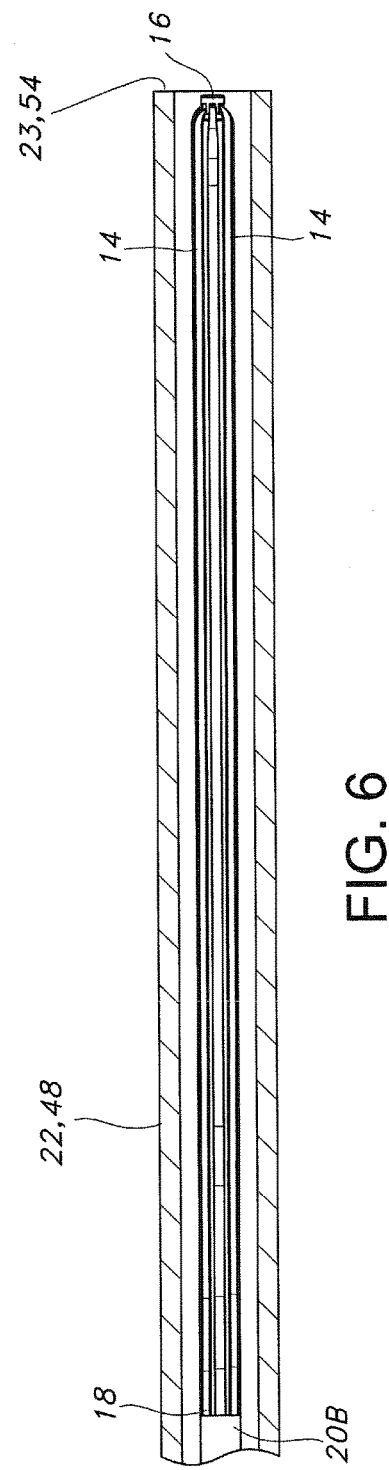

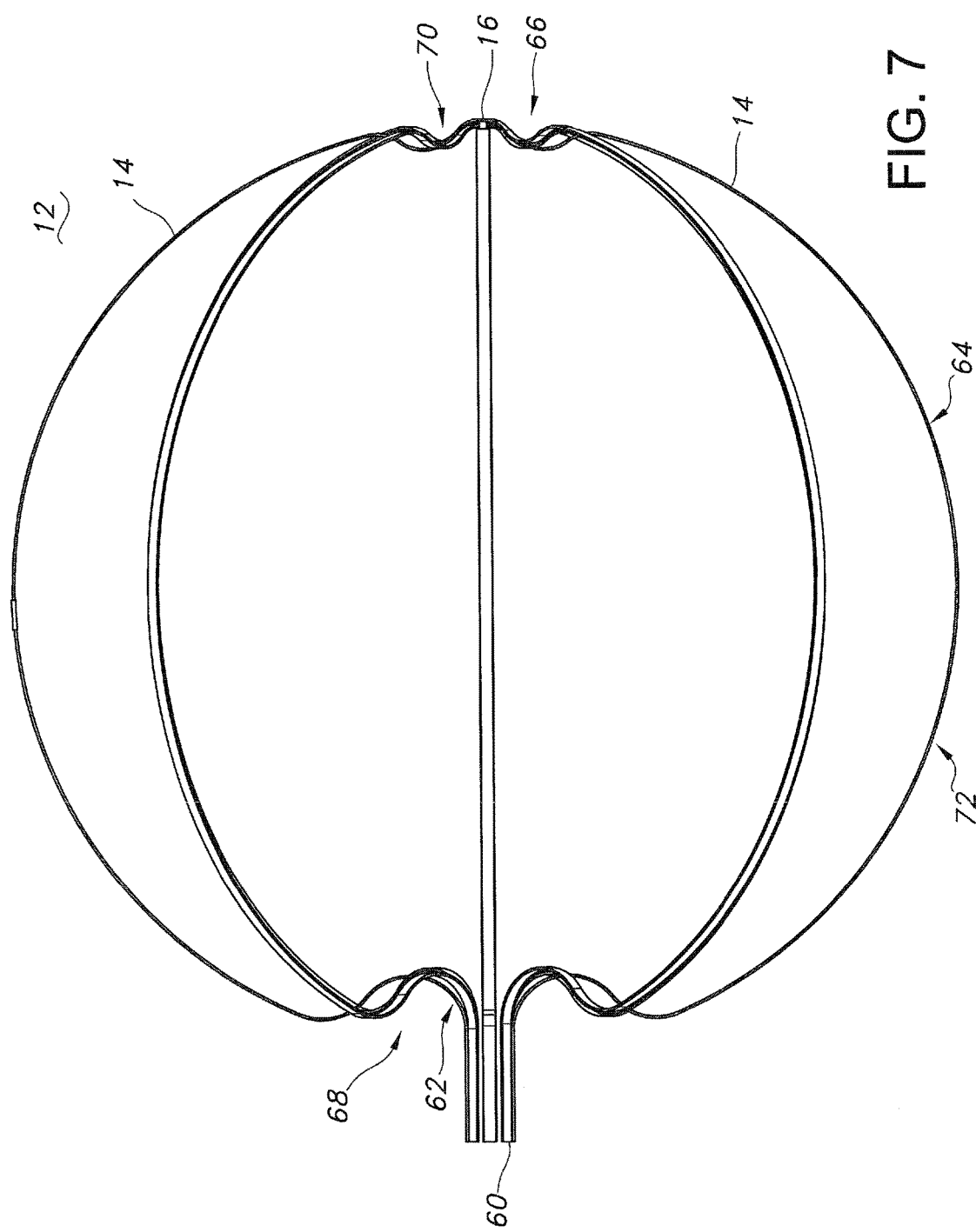

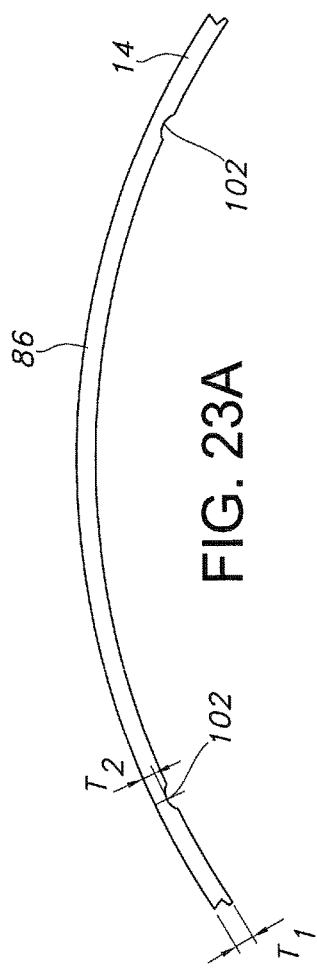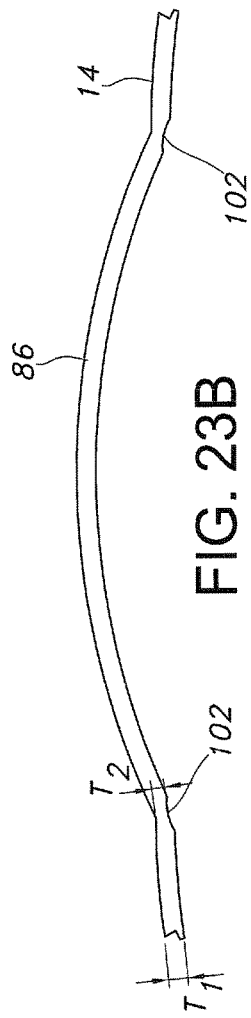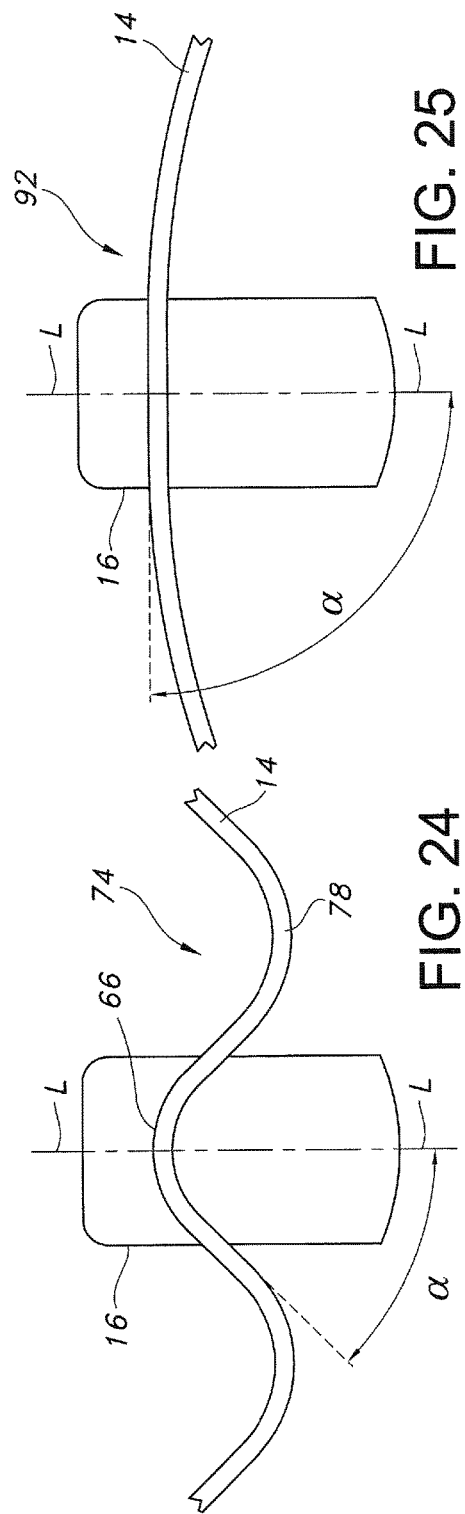

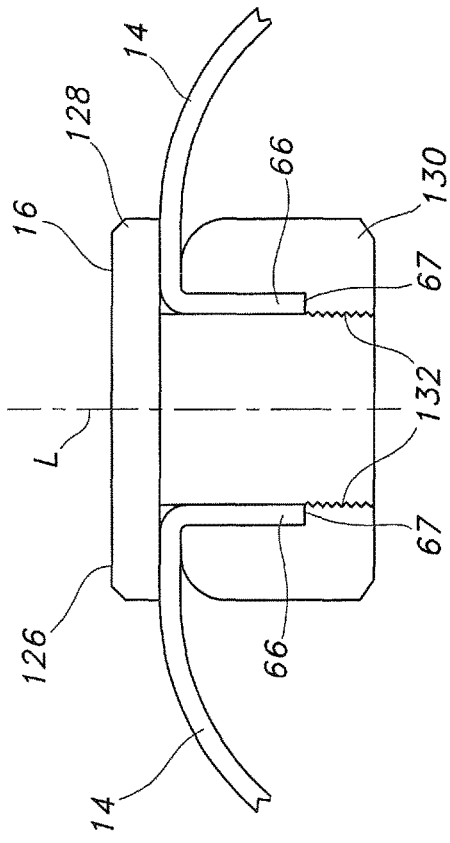
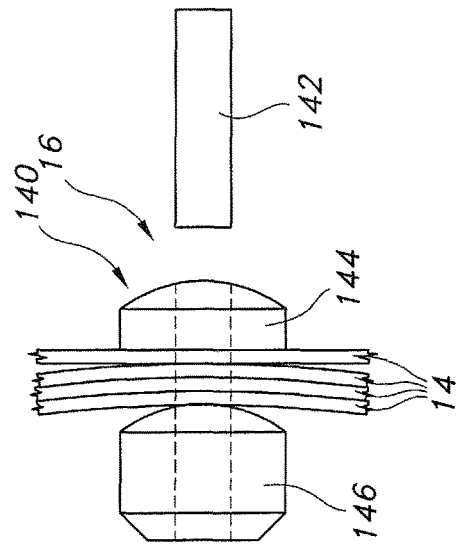
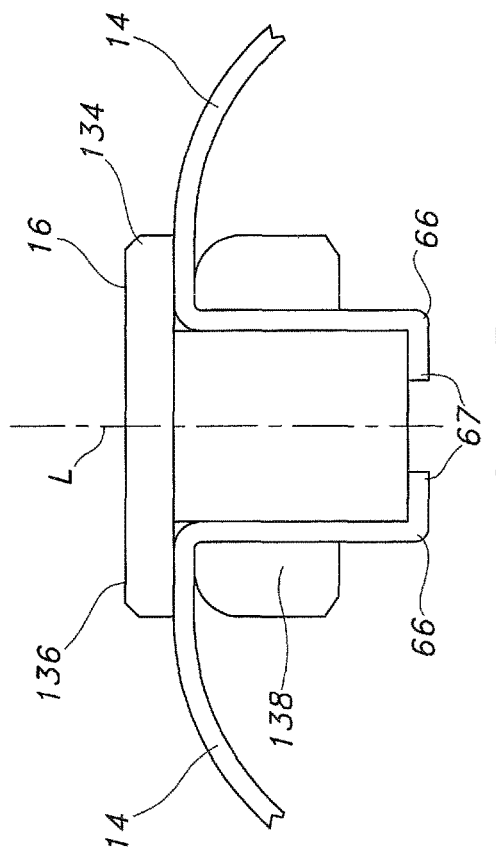
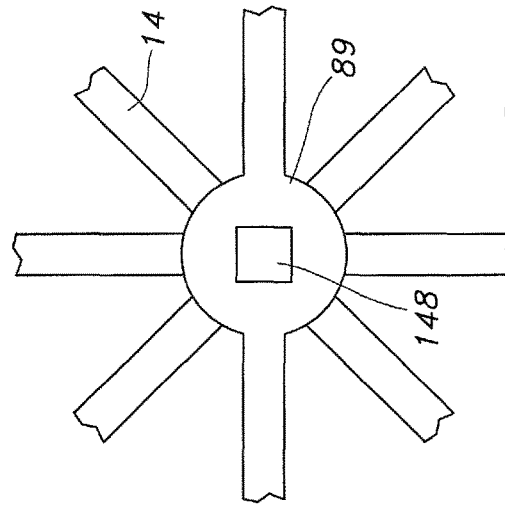
FIG. 28A
FIG. 28B
FIG. 28C
FIG. 28D

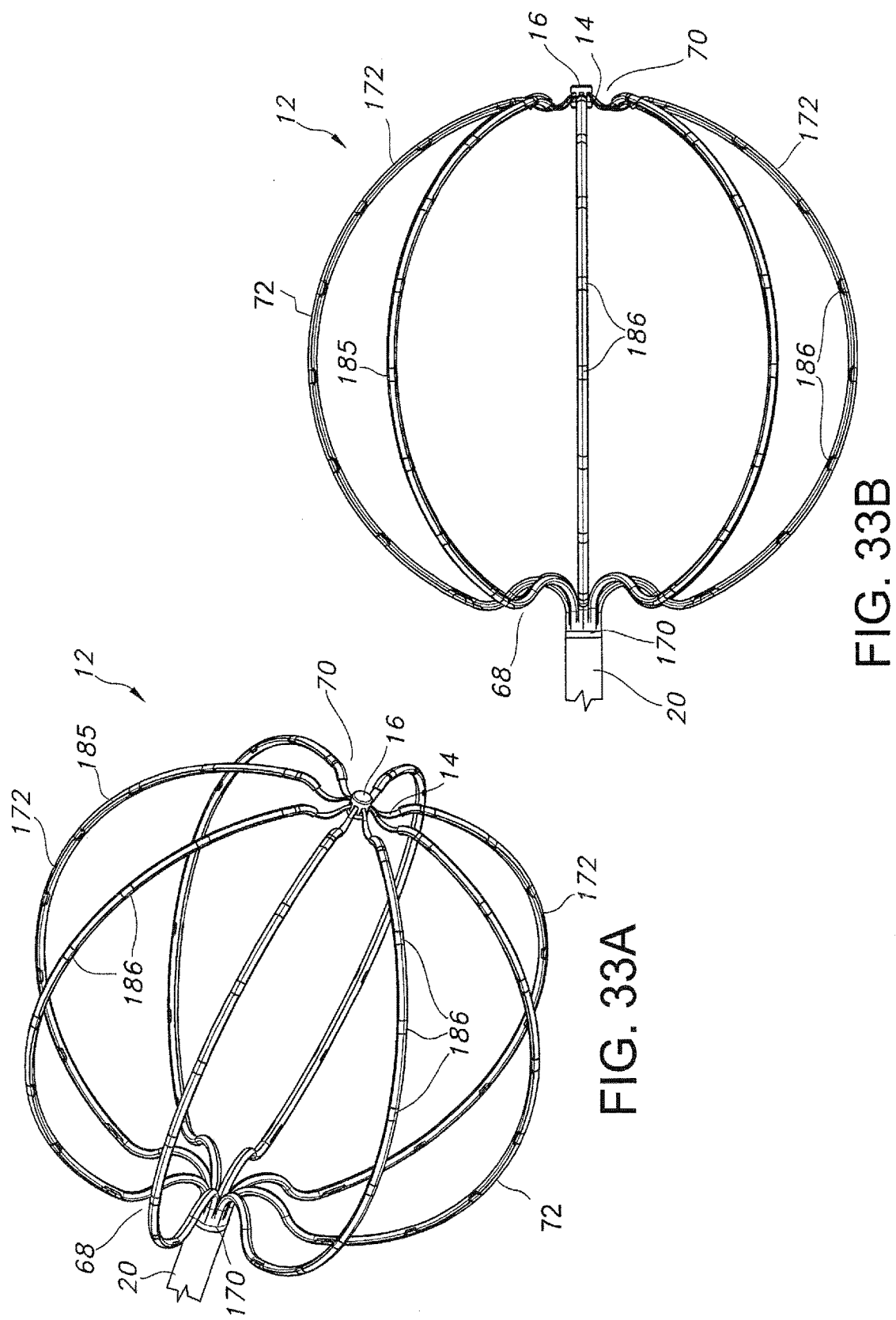

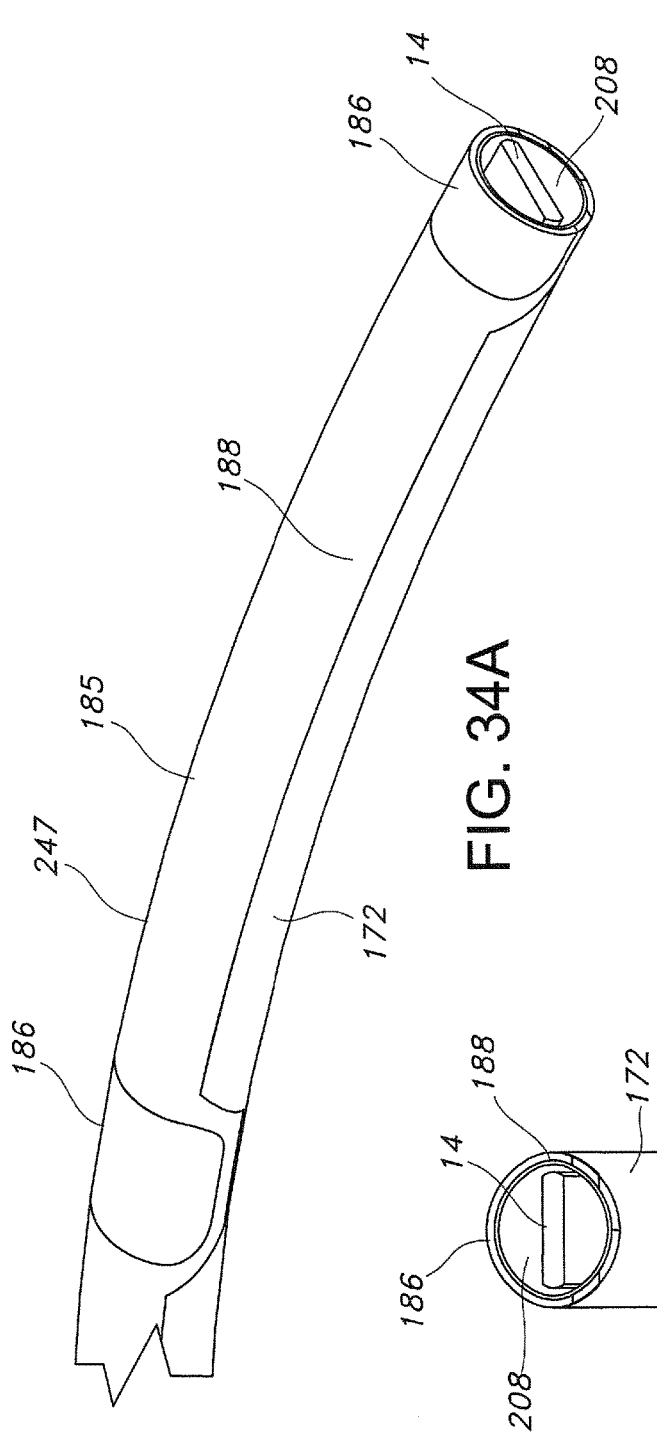
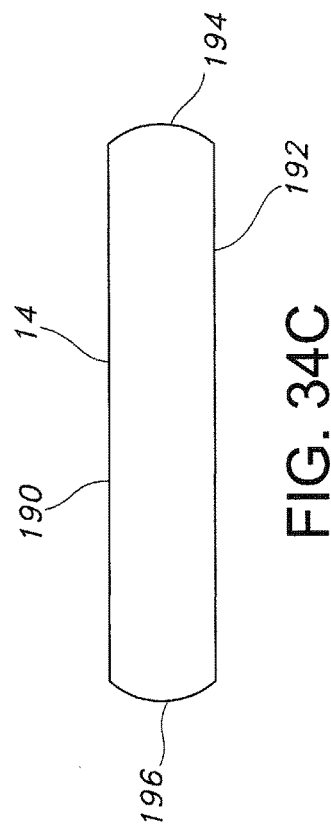
FIG. 34A
FIG. 34B
FIG. 34C

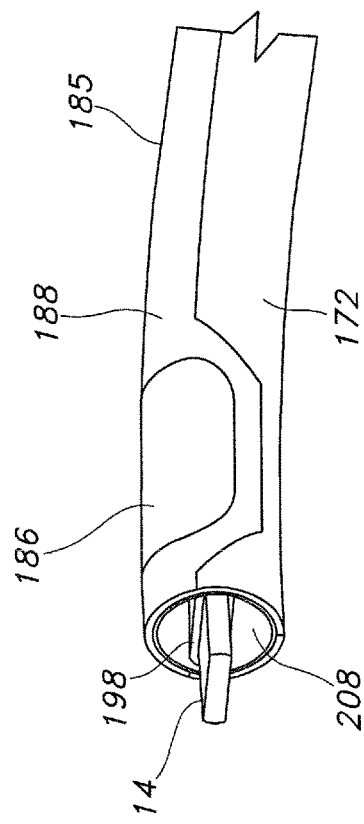
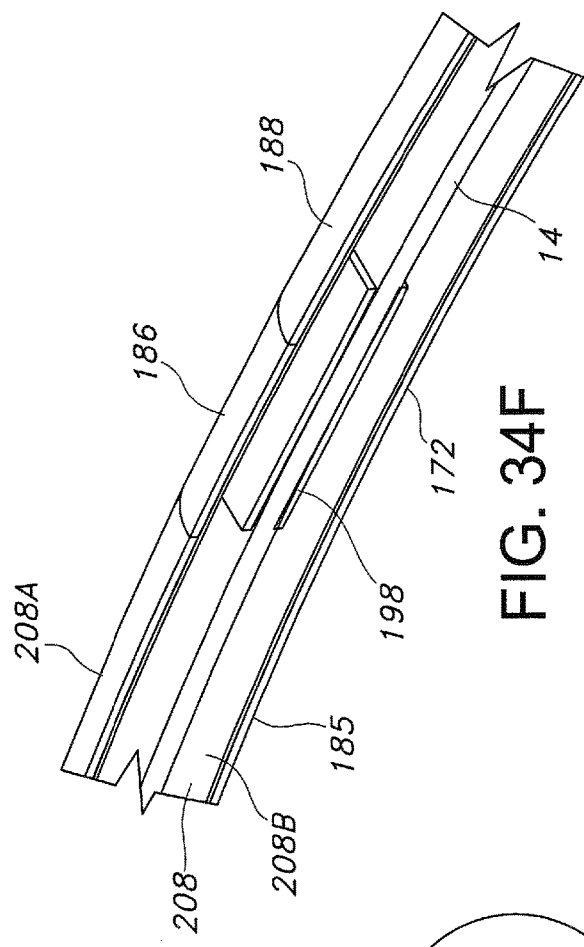
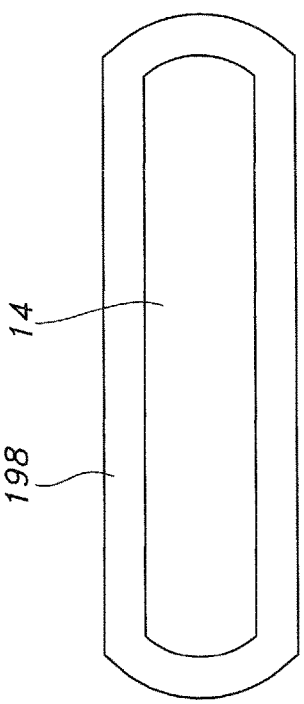
FIG. 34D
FIG. 34F
FIG. 34E

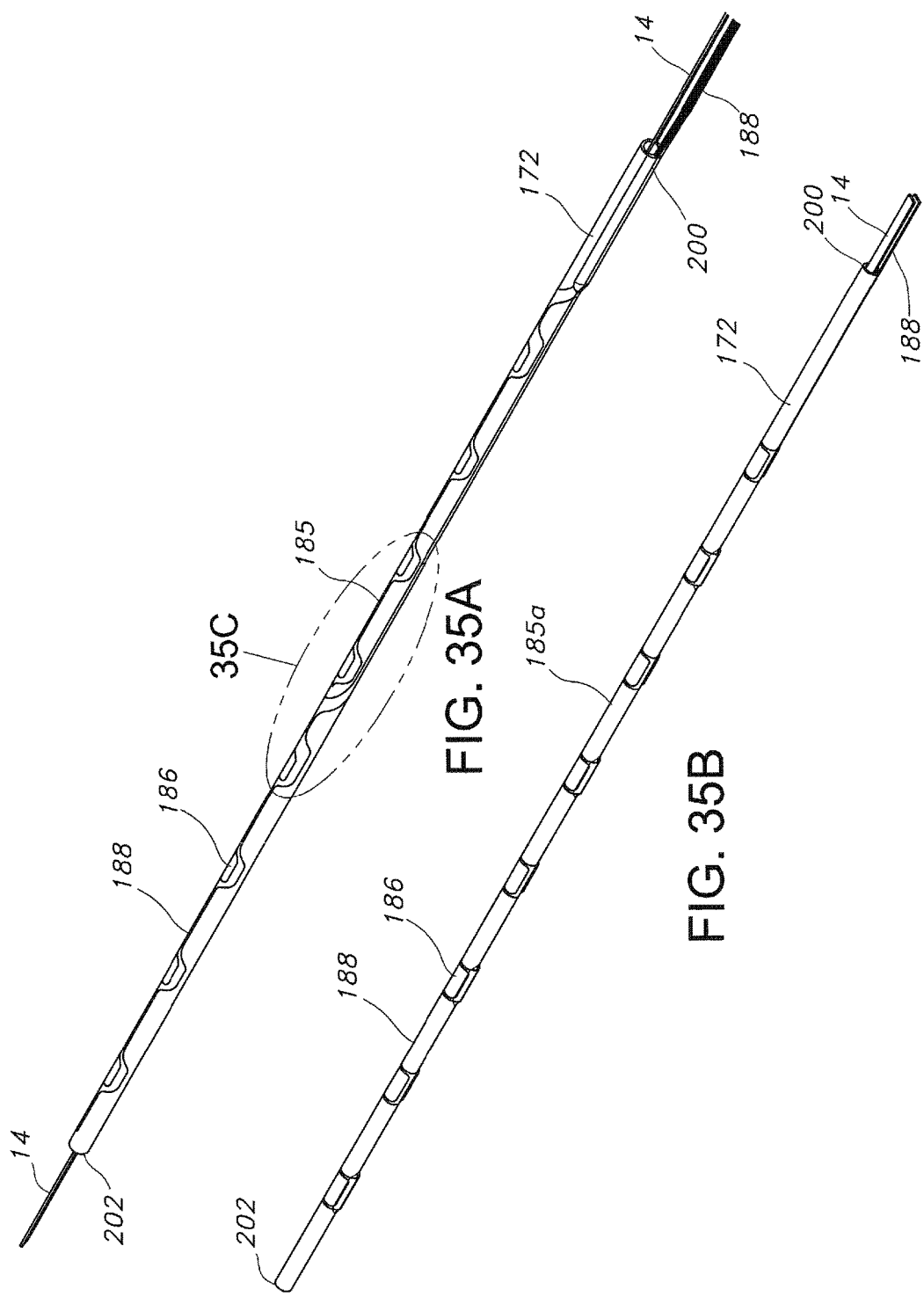

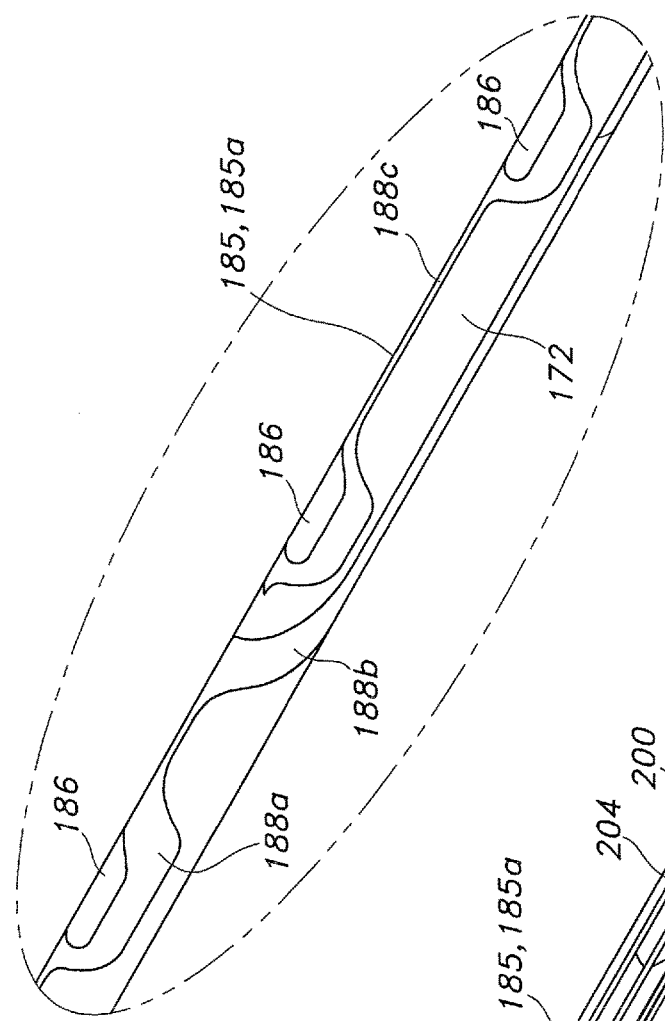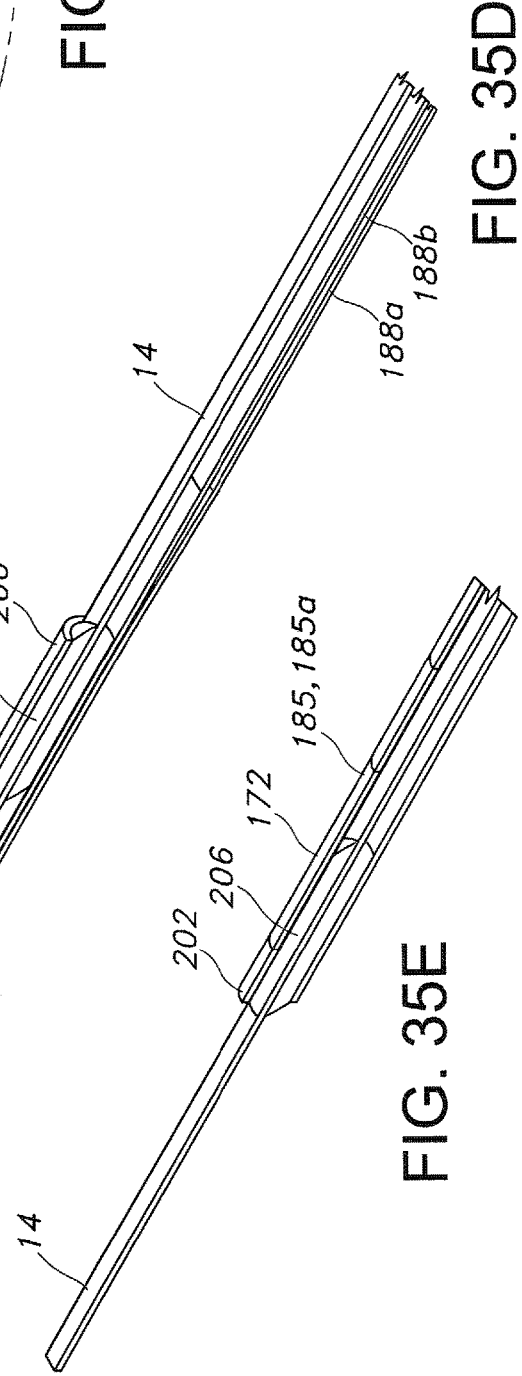

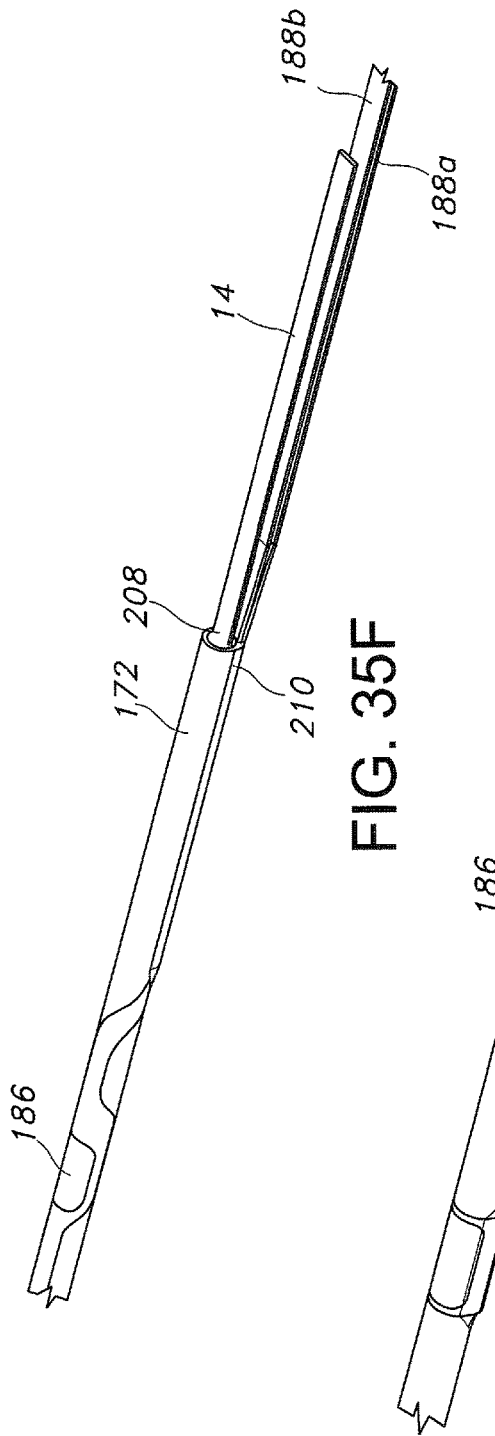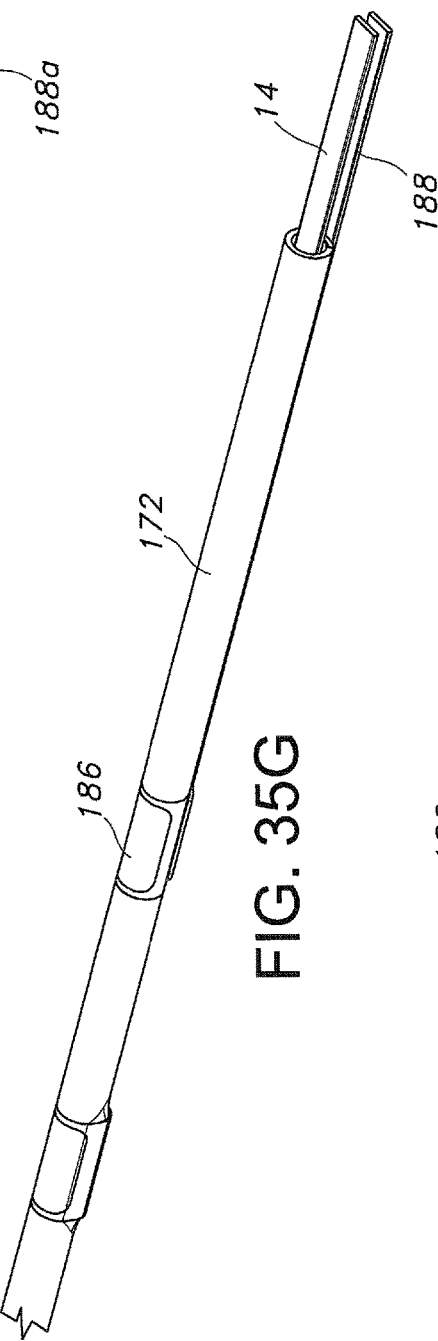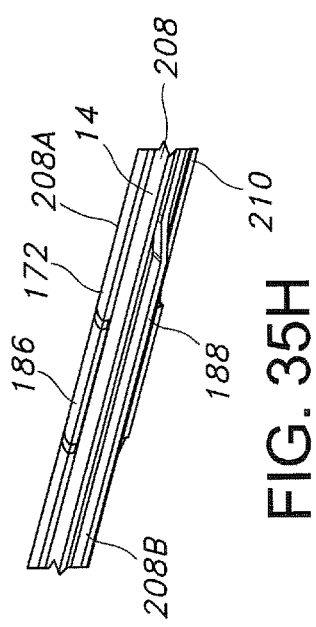

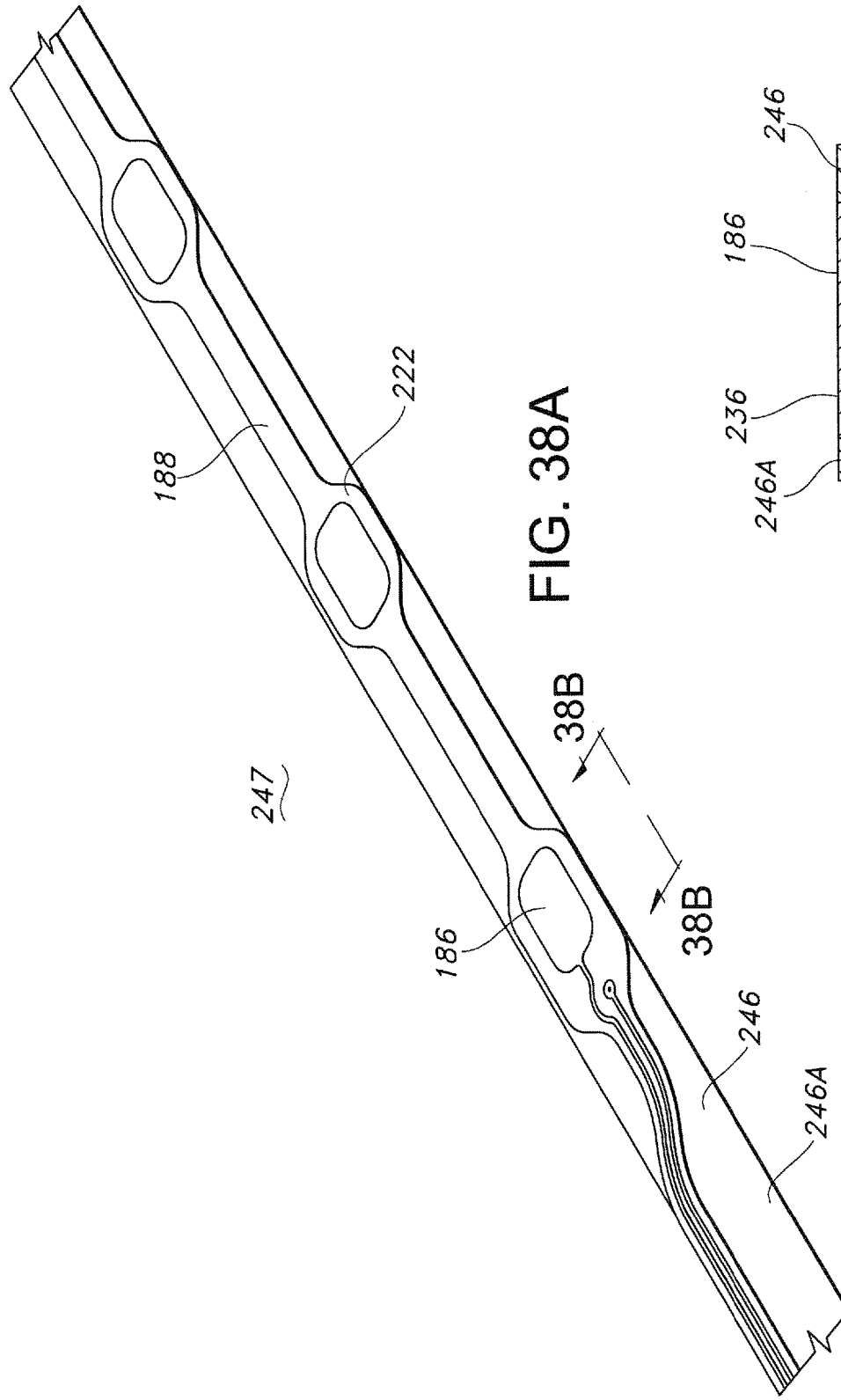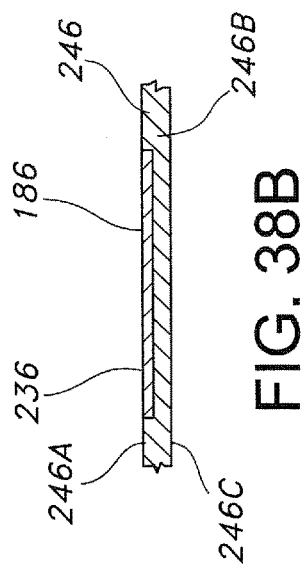

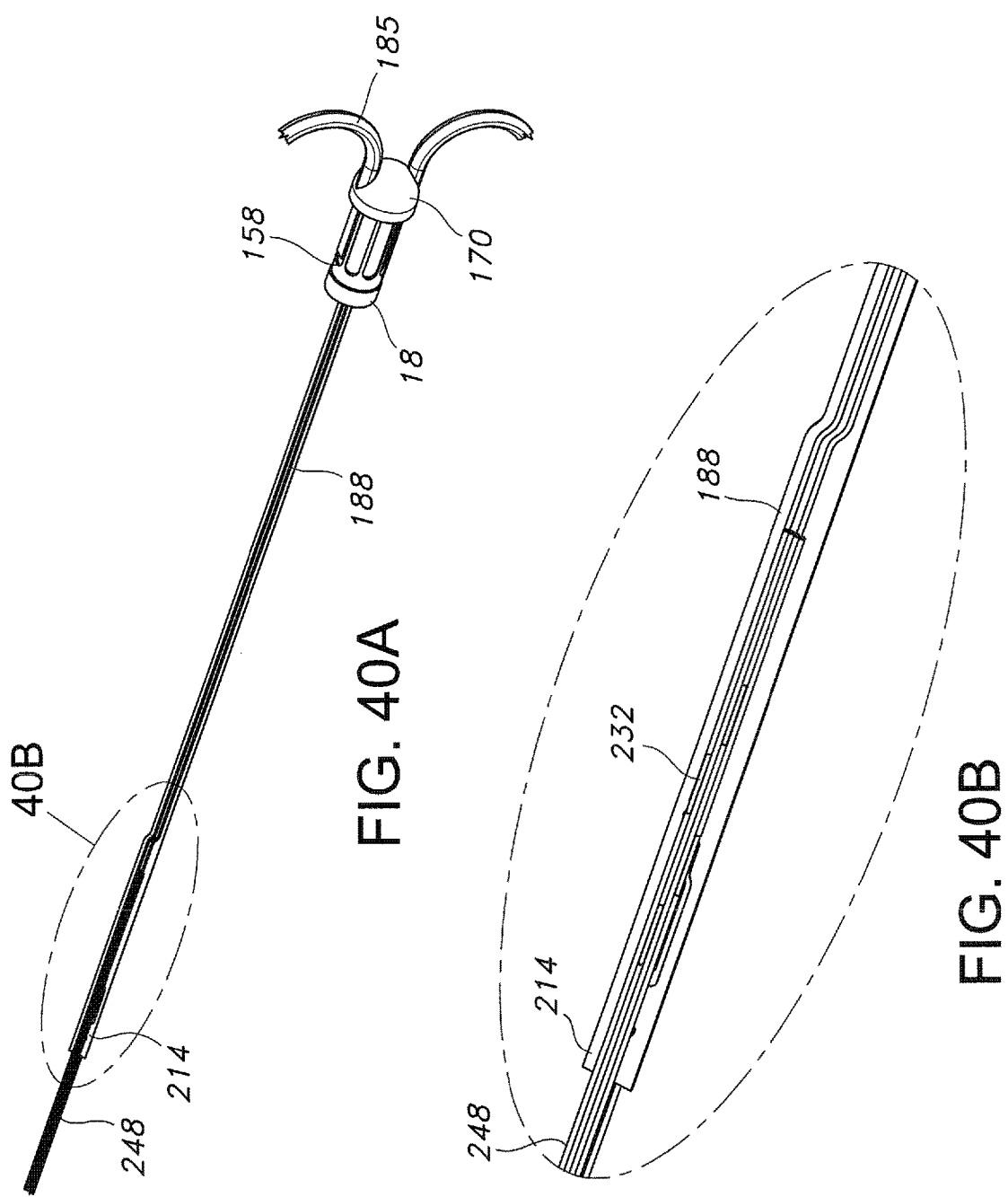

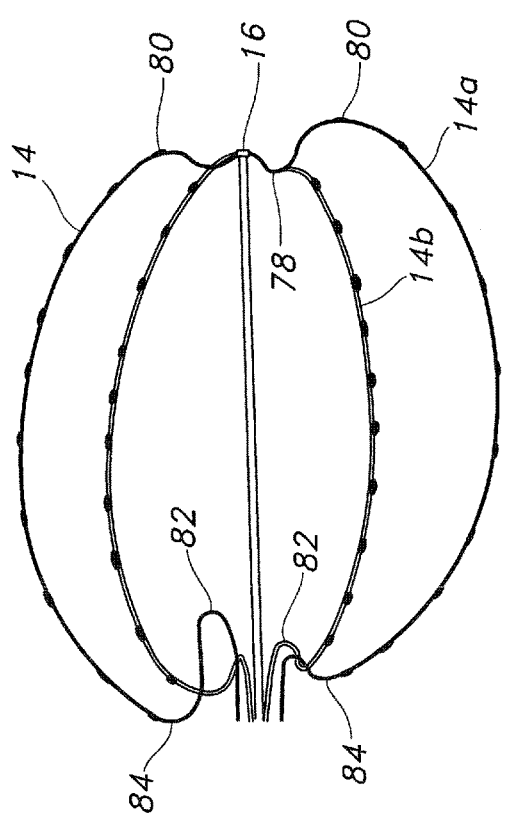
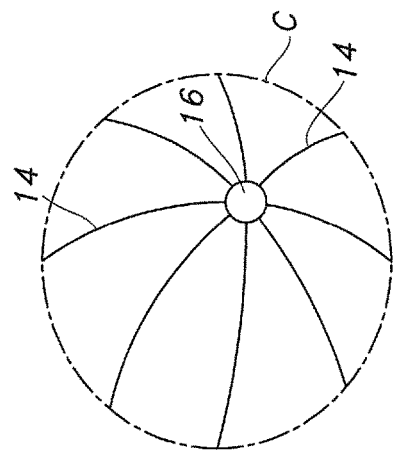
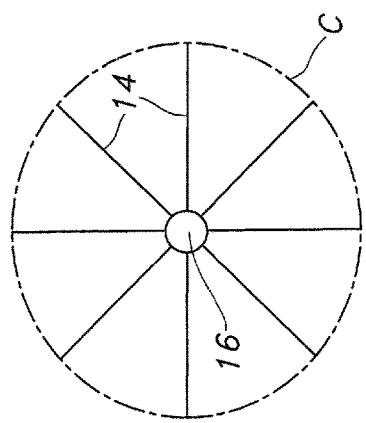
FIG. 42A
FIG. 42B
FIG. 42C

BASKET STYLE CARDIAC MAPPING CATHETER HAVING AN ATRAUMATIC, METALLIC TWO-PART DISTAL TIP FOR DETECTION OF CARDIAC RHYTHM DISORDERS

CROSS-REFERENCE TO RELATED APPLICATIONS

This application is a continuation of U.S. application Ser. No. 13/929,838, filed Jun. 28, 2013, now U.S. Pat. No. 9,504,399, which is a continuation of U.S. application Ser. No. 13/687,274, filed Nov. 28, 2012, now U.S. Pat. No. 8,504,133, which is a continuation of U.S. application Ser. No. 13/409,263, filed Mar. 1, 2012, now U.S. Pat. No. 8,346,339, which claims the benefit of U.S. Provisional Application No. 61/555,190, filed Nov. 3, 2011, and U.S. Provisional Application No. 61/478,340, filed Apr. 22, 2011, the contents of all of which are incorporated by reference herein.

FIELD OF THE INVENTION

The present invention is related to the detection of cardiac rhythm disorders by use of basket style cardiac mapping catheters. The present invention is further related to cardiac spline baskets having flexible spline tube assemblies with electrodes.

BACKGROUND OF THE INVENTION

Heart rhythm disorders are very common in the United States, and are significant causes of morbidity, lost days from work, and death. Heart rhythm disorders exist in many forms, of which the most complex and difficult to treat are atrial fibrillation (AF), ventricular tachycardia (VT) and ventricular fibrillation (VF). Other rhythms may be easier to treat, but may also be clinically significant including supraventricular tachycardia (SVT), atrial tachycardia (AT), atrial flutter (AFL), premature atrial complexes/beats (PAC, APC) and premature ventricular complexes/beats (PVC). Under certain conditions, rapid activation of the normal sinus node can even cause a heart rhythm disorder such as inappropriate sinus tachycardia or sinus node reentry.

Definitive diagnosis has often been performed using electrode-bearing catheters placed within the heart chambers. Electrodes have been positioned along a catheter shaft or basket splines in an attempt to analyze or map the electrical activity within a heart chamber. Mapping typically involves the use or formation external (patches on skin) of electrograms and internal (catheters with electrodes) electrograms. A typical electrocardiogram of the cardiac cycle (heartbeat) consists of a P wave, a QRS complex and a T wave. During normal atrial depolarization, the main electrical vector is directed from the SA node, and spreads from the right atrium to the left atrium. Atrial depolarization is represented by the P wave on the electrocardiogram. The QRS complex reflects the rapid depolarization of the right and left ventricles. The T wave represents the repolarization (or recovery) of the ventricles.

Devices of the prior art, however, often do not provide a complete and stable map of the electrical activity within a heart chamber (recording electrograms). In particular, electrical activity in certain portions of the right atrium and the left atrium (e.g. atrial septum, region of right pulmonary veins) are often difficult to map because of the inability of devices of the prior art to adequately conform to the irregular shape of the atria and their varying shapes during beating of the heart. Further, devices of the prior art do not provide dimensionally and/or spatially stable and complete electrograms as the prior art devices often move as the heart beats, thereby moving some or all of the electrodes away from the heart tissue and making the relative position of the electrodes variable to corresponding position of atrial tissue.

Thus, there is a need in the art for a cardiac mapping catheter that is capable of providing improved and dimensionally and/or spatially stable signals for diagnosis, and more complete coverage of the heart tissue, typically in the form of electrograms.

SUMMARY OF THE INVENTION

The present invention provides devices, systems and methods for the detection of cardiac rhythm disorders by use of a percutaneous catheter designed to permit acquisition of numerous, simultaneous endocardial electrograms from a three dimensional array of surface electrodes, herein referred to as "a basket style cardiac mapping catheter."

In one embodiment of the present invention, a system for sensing multiple local electric voltages from endocardial surface of a heart, includes: an elongate tubular member having a lumen, a proximal end and a distal end; a plurality of flexible splines having proximal portions, distal portions and medial portions therein between, wherein the splines comprise an outer surface, an inner surface and two side surfaces; an anchor for securably affixing the proximal portions of the splines, wherein the anchor is securably affixed within the lumen of the elongate tubular member at the distal end of the elongate tubular member; a tip for securably affixing the distal portions of the splines; and a polymeric member including opposed a first open end and a second open end defining an open lumen therein between and an inner member surface and an outer member surface, wherein at least one of the plurality of flexible splines is at least partially disposed within the lumen of the polymeric member; a flexible electrode assembly strip with one or more exposed electrodes disposed on at least a portion of the outer surface of the polymeric member; wherein the flexible electrode assembly strip includes: a polymeric substrate having an inner surface and an opposed outer surface; the one or more exposed electrodes disposed over at least part of the outer surface of the polymeric substrate; and one or more electrical traces disposed over at least a portion of the inner surface of the polymeric substrate or over at least a portion of the outer surface of the polymeric substrate, the one or more electrical traces being in electrical communication with the one or more exposed electrodes; wherein a portion of the flexible electrode assembly transitions from the outer surface of the polymeric member towards the inner surface of the polymeric member prior to the anchor; and wherein another portion of the flexible electrode assembly extends through at least a portion of the anchor and into the lumen of the elongate tubular member.

In one embodiment of the present invention, a system for sensing multiple local electric voltages from endocardial surface of a heart, includes: an elongate tubular member having a lumen, a proximal end and a distal end; a plurality of flexible splines having proximal portions, distal portions and medial portions therein between, wherein the splines comprise an outer surface, an inner surface and two side surfaces; an anchor for securably affixing the proximal portions of the splines, wherein the anchor is securably affixed within the lumen of the elongate tubular member at the distal end of the elongate tubular member; a tip for securably affixing the distal portions of the splines; and a polymeric member including opposed first and second open ends defining an open lumen therein between and an inner member surface and an outer member surface, wherein at least one of the plurality of flexible splines is at least partially disposed within the lumen of the polymeric member; a flexible electrode assembly strip with one or more exposed electrodes disposed on at least a portion of the outer surface of the polymeric member; wherein the flexible electrode assembly strip includes: a polymeric substrate having an inner surface and an opposed outer surface; the one or more exposed electrodes disposed over at least part of the outer surface of the polymeric substrate; and one or more electrical traces disposed over at least a portion of the inner surface of the polymeric substrate or over at least a portion of the outer surface of the polymeric substrate, the one or more electrical traces being in electrical communication with the one or more exposed electrodes; wherein the first opposed open end of the polymeric member is secured to the distal spline portion of the at least one of the plurality of flexible splines at a position near to the distal tip and the second opposed open end of the polymeric member is secured to the proximal spline portion of the at least one of the plurality of flexible splines at a position near to the anchor; and wherein medial portions of the polymeric member between the first opposed open end and the second opposed open end of the polymeric member are not secured to the medial portions of the at least one of the plurality of flexible splines.

In one embodiment of the present invention, a system for sensing multiple local electric voltages from endocardial surface of a heart, includes: an elongate tubular member having a lumen, a proximal end and a distal end; a plurality of flexible splines having proximal portions, distal portions and medial portions therein between, wherein the splines comprise an outer surface, an inner surface and two side surfaces, wherein the inner and outer spline surfaces have a substantially flat portion with the substantially flat portions being parallel to one and the other, and further wherein the two side spline surfaces are convexly rounded to define a rounded-rectangular shape; an anchor for securably affixing the proximal portions of the splines, wherein the anchor is securably affixed within the lumen of the elongate tubular member at the distal end of the elongate tubular member; a tip for securably affixing the distal portions of the splines; and a plurality of polymeric members each having opposed first and second open ends defining an open lumen therein between, wherein the polymeric members comprise an outer surface, an inner surface and two side surfaces where a cross-sectional profile of the polymeric members is elliptical to match a cross-sectional profile of the rounded-rectangular shape of the splines and is slightly larger than the cross-sectional profile of the rounded-rectangular shape of the splines and wherein each of the plurality of flexible splines is at least partially disposed within the lumen of a different one of the plurality of polymeric members; a flexible electrode assembly strip with one or more exposed electrodes disposed on at least a portion of the outer surface of the polymeric members; wherein the flexible electrode assembly strip includes: a polymeric substrate having an inner surface and an opposed outer surface; the one or more exposed electrodes disposed over at least part of the outer surface of the polymeric substrate; and one or more electrical traces disposed over at least a portion of the inner surface of the polymeric substrate or over at least a portion of the outer surface of the polymeric substrate, the one or more electrical traces being in electrical communication with the one or more exposed electrodes; wherein a portion of the flexible electrode assembly strip extends through at least a portion of the anchor and into the lumen of the elongate tubular member.

In one embodiment of the present invention, a system for sensing multiple local electric voltages from endocardial surface of a heart, includes: an elongate tubular member having a lumen, a proximal end and a distal end; a plurality of flexible splines having proximal portions, distal portions and medial portions therein between, wherein the splines comprise an outer surface, an inner surface and two side surfaces; an anchor for securably affixing the proximal portions of the splines, wherein the anchor is securably affixed within the lumen of the elongate tubular member at the distal end of the elongate tubular member; a tip for securably affixing the distal portions of the splines; and a plurality of polymeric members each having opposed first and second open ends defining an open lumen therein between and an outer surface and an inner surface, wherein each of the plurality of flexible splines is at least partially disposed within the lumen of a different one of the plurality of polymeric members; a flexible electrode assembly strip with one or more exposed electrodes disposed on at least a portion of the outer surface of the polymeric members; wherein the flexible electrode assembly strip includes: a polymeric substrate having an inner surface and an opposed outer surface; the one or more exposed electrodes disposed over at least part of the outer surface of the polymeric substrate; and one or more electrical traces disposed over at least a portion of the inner surface of the polymeric substrate or over at least a portion of the outer surface of the polymeric substrate, the one or more electrical traces being in electrical communication with the one or more exposed electrodes; wherein the flexible electrode assembly strip is compressed into the outer surface of the polymeric member; and wherein the flexible electrode assembly strip is thermally or adhesively bonded to the outer surface of the polymeric member.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

BRIEF DESCRIPTION OF THE DRAWINGS

FIG. 2 is a side elevational view of the basket style cardiac mapping catheter system of FIG. 1, according to the present invention.

FIG. 3 is a schematic view of an introducing catheter of the prior art useful for delivery of the basket style cardiac mapping catheter of FIG. 1 and guide catheter of FIG. 4 into a bodily lumen or organ.

FIG. 4 is a schematic view of a guide catheter of the prior art useful for delivery of the basket style cardiac mapping catheter of FIG. 1 into a bodily lumen or organ.

FIG. 5 is an expanded, partial cross-sectional view of a portion of the basket of the system of FIG. 1 showing an expanded basket beyond and outside a hemostat penetrator and/or a guide catheter, according to the present invention.

FIG. 6 is an expanded, partial cross-sectional view of a portion of the basket of the system of FIG. 1 showing a radially compressed basket within a hemostat penetrator and/or a guide catheter, according to the present invention.

FIG. 7 is an expanded side view of a portion of the basket of the system of FIG. 1 showing M-shaped, symmetric distal splines, according to the present invention.

FIG. 20 is an exploded view of a distal portion of the spline of FIG. 18, according to the present invention.

FIG. 23A depicts side view of a portion of a spline in a neutral position having buckle points, according to the present invention.

FIG. 23B depicts side view of a portion of a spline in a deflected position having buckle points, according to the present invention.

FIG. 24 is a schematic illustration of a spline emerging from a distal tip at an acute angle, according to the present invention.

FIG. 25 is a schematic illustration of a spline emerging from a distal tip at a substantially perpendicular angle, according to the present invention.

FIG. 28A is a side cross-sectional view of another embodiment of a two-part distal tip with half splines, according to the present invention.

FIG. 28B is a side cross-sectional view of another embodiment of a two-part distal tip with half splines, according to the present invention.

FIG. 28C is a side cross-sectional view of another embodiment of a two-part riveted distal tip with full splines, according to the present invention.

FIG. 28D is a top view of aligned splines useful with the distal tip of FIG. 28C, according to the present invention.

FIG. 33A is an exploded, perspective of the basket of the system of FIG. 1 showing splines with spline tube assemblies, according to the present invention.

FIG. 33B is a side elevational view of the basket of FIG. 33A, according to the present invention.

FIGS. 34A and 34B are cross-sectional views of a portion of the spline tube assembly of FIG. 33A, according to the present invention.

FIG. 34C is an exploded cross-section view of the spline of FIGS. 34A and 34B, according to the present invention.

FIG. 34D is a cross-sectional view of a spline tube assembly with a radiopaque marker, according to the present invention.

FIG. 34E is a cross-sectional view of the radiopaque marker of FIG. 34D, according to the present invention.

FIG. 34F is a partial cross-sectional view of a spline tube assembly along the length of the spline tube assembly with a radiopaque marker, according to the present invention.

FIG. 35A is a perspective view of spline tube assembly, according to the present invention.

FIG. 35B is another perspective views of spline tube assembly, according to the present invention.

FIG. 35C is an exploded perspective view of a spline tube assembly, according to the present invention.

FIG. 35D is an exploded, partial cross-sectional view of a proximal portion of the spline tube assembly, according to the present invention.

FIG. 35E is an exploded, partial cross-sectional view of a distal portion of the spline tube assembly, according to the present invention.

FIG. 35F is an exploded, partial cross-sectional view of a proximal portion of the spline tube assembly showing two flex circuits embedded with a wall of the spline tube assembly, according to the present invention.

FIG. 35G is an exploded, partial cross-sectional view of a proximal portion of the spline tube assembly showing one flex circuit embedded with a wall of the spline tube assembly, according to the present invention.

FIG. 35H is an exploded, partial cross-sectional view of a portion of the spline tube assembly showing a flex circuit transitioning into an inner lumen of the spline tube assembly, according to the present invention.

FIG. 38A is a perspective view of a flex circuit embedded or pressed into a substrate, according to the present invention.

FIG. 38B is a partial, side cross-sectional view of the flex circuit of FIG. 38A, according to the present invention.

FIG. 40A is a partial perspective view of a quad wire assembly with a flex circuit, according to the present invention.

FIG. 40B is a partial cross-sectional view of the quad wire assembly with a flex circuit of FIG. 40A, according to the present invention.

FIG. 42A is a side elevational view of asymmetric catheter basket FIG. 13, according to the present invention.

FIG. 42B is a front elevational view of a symmetric basket, according to the present invention.

FIG. 42C is a front elevational view of an asymmetric basket, according to the present invention.

DETAILED DESCRIPTION OF THE PREFERRED EMBODIMENTS

Figure 1:
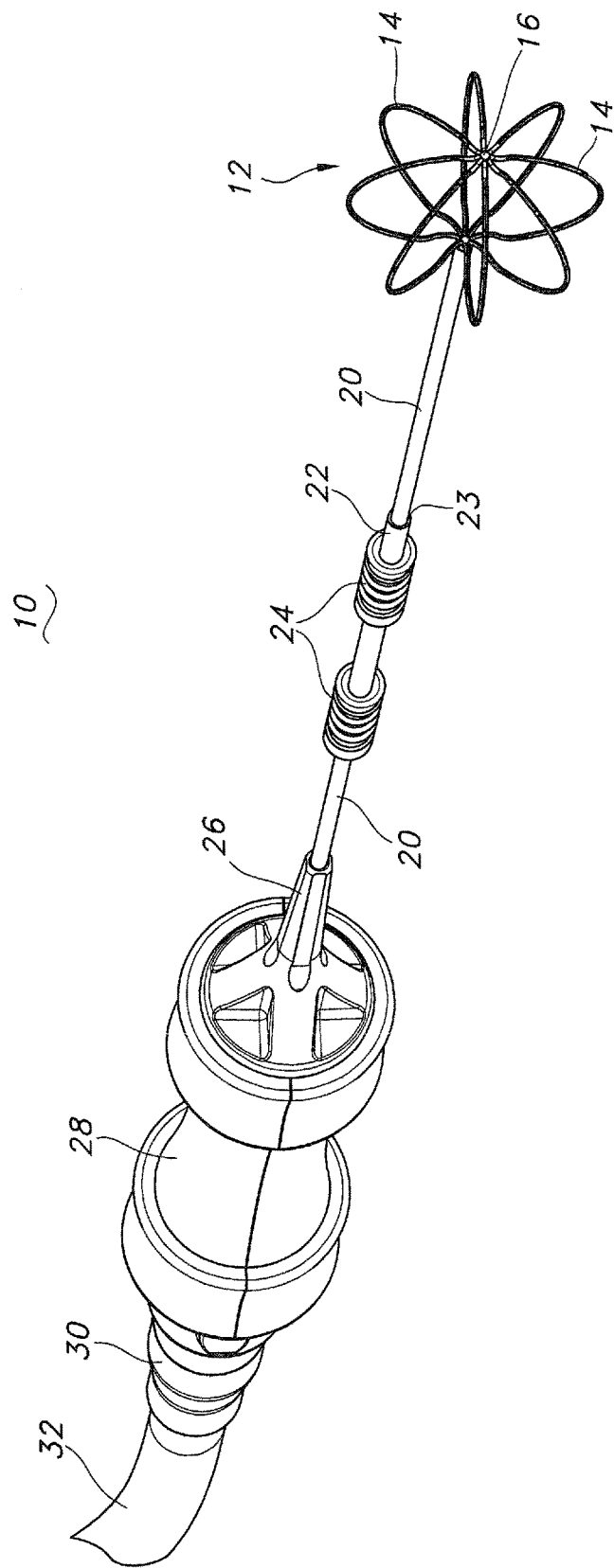
FIG. 1 is a perspective view of the basket style cardiac mapping catheter system of the present invention.

FIG. 1 is a perspective view of basket style cardiac mapping system or assembly 10 of the present invention, and FIG. 2 is a side elevation view of the catheter system or assembly 10 of FIG. 1. As depicted in FIGS. 1 and 2, the catheter system or assembly 10 consists of three subassemblies: the mapping catheter assembly 8, including hemostat penetrator assembly 25, and the extension cable assembly 31. The mapping catheter assembly 8 includes a spline basket 12, which includes splines 14 with spline tube assemblies (not shown) having electrodes (not shown); a catheter body or shaft 20; a hemostat penetrator assembly 25 (comprised of a hemostat penetrator tube 22 and hemostat penetrator handles 24); a handle strain relief 26; a handle 28, with an integral connector (not shown). The extension cable assembly 31 includes a mating connector 30 and an extension cable 32; interrelated as shown. The catheter assembly 8 allows ease of operation and precise positioning and control of the basket 12 within a patient. Desirably, connector 30 is round so there is no rotational bias as the basket 12 is disposed within a patient. A non-round connector grip, for example a rectangular connector grip (not shown) may provide a rotational bias which, if desired, may be used with the present invention. The mating connector cable assembly 31 is useful for connecting the catheter assembly 8 to external devices (not shown), such as devices that receive and analyze electrical signals from the catheter system 10. The strain relief section 26 is useful in providing kink resistance to the catheter body 20 especially when the catheter assembly 8 is disposed within a patient.

The splines 14 of the spline basket 12 are secured by a distal tip 16 at one end, i.e. the distal end, of the basket 12, and are further secured by a proximal anchor 18 at an opposed end, i.e. the proximal end, of the basket 12. The anchor 18 is secured to a distal end 20B of the catheter body 20 and/or within a lumen 20C of the catheter body 20 of the catheter 8 of the present invention. The proximal end 20A of the catheter body 20 is secured to the strain relief section 26 of the handle 28.

The spline basket 12 is deliverable through and into bodily organs, such as but not limited to the right atrium of a heart. One useful delivery technique includes the Seldinger delivery technique. The Seldinger techniques uses a short introducing catheter, such as the introducing catheter 34 as depicted in FIG. 3, and a longer catheter, such as the catheter 46, which may also be referred to as an guide catheter or delivery sheath when described with the system 10 of the present invention, as depicted in FIG. 4. The introducing catheter or introducer 34 is typically fairly short at about six inches in length and is used to navigate through muscle and into a desired vein. The catheter 46 is typically a long guide sheath, typically 60 mm to 80 long. In a typical Seldinger technique, a vessel or cavity is punctured with a sharp hollow needle or trocar (not shown). If desired, a guidewire (not shown) may be then advanced through the lumen of the trocar, and the trocar is withdrawn. The introducing catheter 34 may then be passed over the guidewire into the cavity or vessel. The introducing catheter 34 includes a hollow introducer lumen 36. The distal end 42 of the introducing catheter 34 is positioned with a vessel or cavity. The proximal end 44 of the introducing catheter 34 remains outside of the patient so as to allow a practitioner to control the position of the distal end of the introducing catheter 42. The proximal end 44 of the introducing catheter 34 may include a hemostat valve 38 and a saline flush lumen 40. The catheter lumen 48 of the guide catheter 46 is deliverable through the lumen 36 of the introducing catheter 34 to a desired bodily site. The guide catheter 46 includes a distal end 54 and a proximal end 56. The guide catheter 46 may also include a proximal hemostat valve 50 and a saline flush lumen 52.

As used herein the term "proximal" generally refers to a location or direction towards the practitioner. The term "distal" generally refers to a location or direction away from the practitioner. Further, the terms inner, inward and the like generally refer to a direction toward the inside of the basket 12, for example towards a longitudinal axis L between the distal tip 16 and the proximal anchor 18. The terms outer, outward and the like generally refer to a direction away from the inside of the basket 12, for example away from a longitudinal axis L between the distal tip 16 and the proximal anchor 18.

In preparation for insertion of the basket catheter 8, the basket 12 is collapsed within the hemostat penetrator tube 22 of the hemostat penetrator assembly 25. The distal end 23 of the hemostat penetrator is insertable through the hemostat valve 50 of the Guide catheter 46. The basket 12 and a portion of the catheter body 20 are advanced and deliverable through lumen 48 and past the distal end 54 of the catheter 46. Typically, the strain relief portion 26, the handle 28, the mating connector 30 and the connector 32 of the system 10 of the present invention remain outside of the body or proximally past the proximal end 56 of the catheter 46. Upon withdrawal of the hemostat penetrator tube 22 from the guide sheath hemostat valve 50, the guide sheath hemostat valve with create a leak-proof seal against the outer wall of the catheter body 20, preventing the loss of blood through the introducer system.

FIGS. 5 and 6 depict an embodiment of the distal end of the basket style cardiac mapping catheter 8 of the present invention. As depicted in FIG. 5 the spline basket 12 is deliverable through and past the distal end 54 of the lumen 48 of the catheter 46 and deliverable through and past the distal end 23 of the hemostat penetrator 25, which also has an open lumen. The distal end 23 of the hemostat penetrator 25 is useful for penetrating the hemostat valve 56 on the proximal end of the guide catheter 46.

As depicted in FIG. 5, the splines 14 of the spline basket 12 are in an expanded state, such as a radially expanded state. The overall shape of the expanded basket 14 is depicted as being an expanded, non-cylindrical shape. While the expanded splines 14 are depicted in a spherical or somewhat spherical orientation, the present invention is not so limited. Indeed, in preferred embodiments of the present invention the expanded splines 14 assume a non-spherical or substantially non-spherical shape, preferably asymmetric, especially but not limited to the spline portions near the distal tip 16 and/or the spline portions near the proximal anchor 18. Such overall shapes are non-limiting, and other overall basket shapes, including substantially spherical shapes, asymmetric spherical shapes, non-spherical shapes, non-spherical asymmetric shapes and the like may suitably be used.

As depicted in FIG. 6, the splines 14 of the spline basket 12 may be in a compressed state within the lumen 48 of the guide catheter 46 and/or of the lumen of the hemostat penetrator tube 22. The splines 14 are depicted in FIG. 6 as being in a compressed approximate or substantial elongate cylindrical shape. In such a compressed state the effective length of the splines 14 between the distal tip 16 and the proximal anchor 18 are substantially the same. Effective spline lengths between the distal tip 16 and the proximal anchor 18 in the expanded basket shape of, for example, FIG. 5 are not so limited and, if desired, may vary as described in further detail below.

FIG. 7 is an expanded side view of a portion of the basket 12 of the system 8 of FIG. 1 showing M-shaped, symmetric distal splines, according to the present invention. The distal basket portion 70 has distal spline portions 66 secured to one and the other by the distal tip 16. The proximal basket portion 68 contains proximal spline portions 62. The proximal spline ends 60 are secured by the proximal anchor 18 (not shown). Medial basket portions 72 and medial spline portions 64 are disposed between the respective ends.

As depicted in FIG. 7, the splines 14, including medial portions 64 of the splines 14, expand or bow outwardly to assume an expanded, non-cylindrical shape, with the basket 12 having a proximal basket portion 68, a distal basket portion 70 and a medial basket portion 72 there between. While the expanded splines are depicted in a spherical or somewhat spherical orientation, the present invention is not so limited. Indeed, in preferred embodiments of the present invention the expanded splines 14 assume a non-spherical or substantially non-spherical shape, preferably asymmetric.

Figure 8:
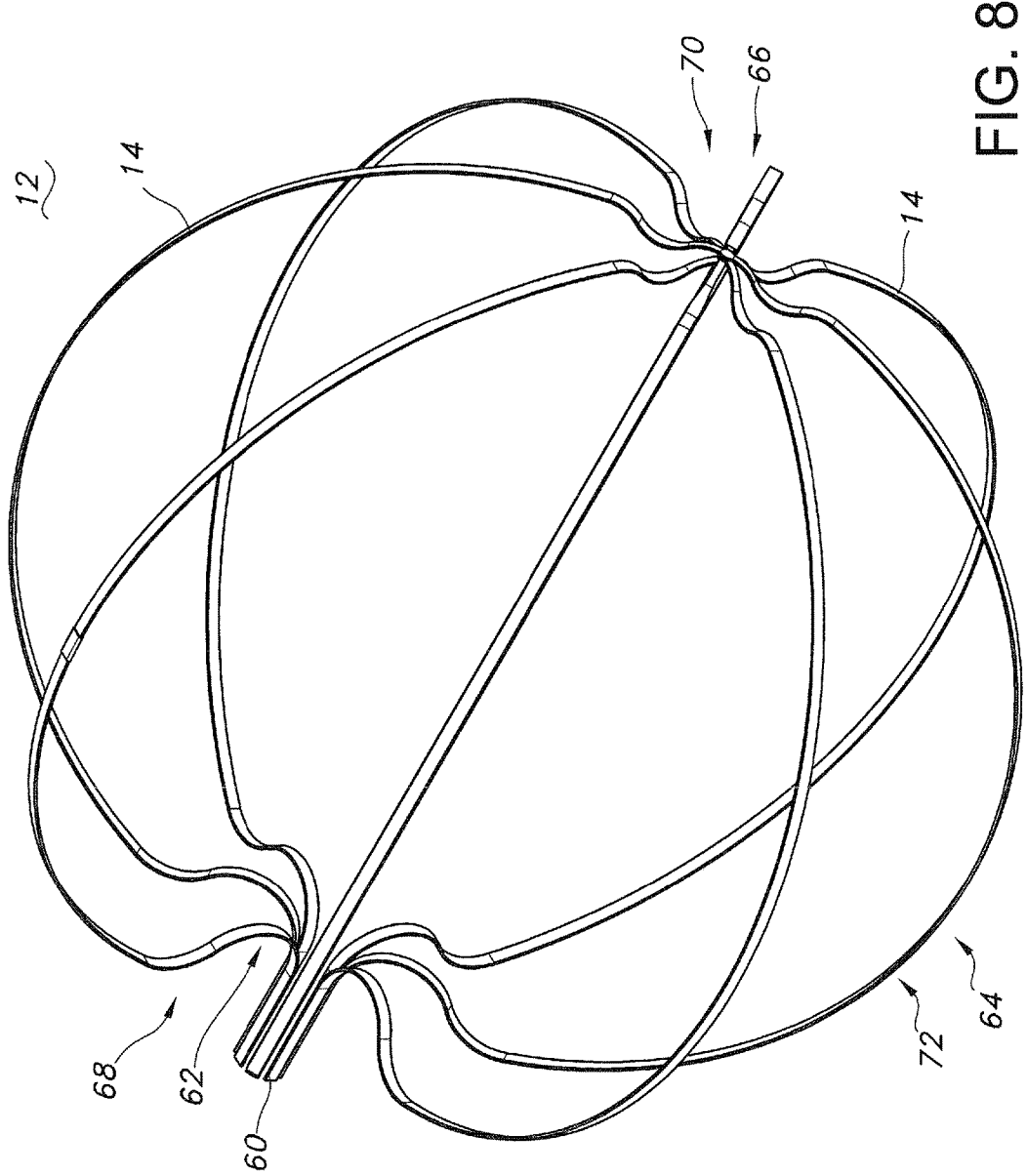
FIG. 8 is a perspective view of the M-shaped basket embodiment of FIG. 7, according to the present invention.
Figure 9:
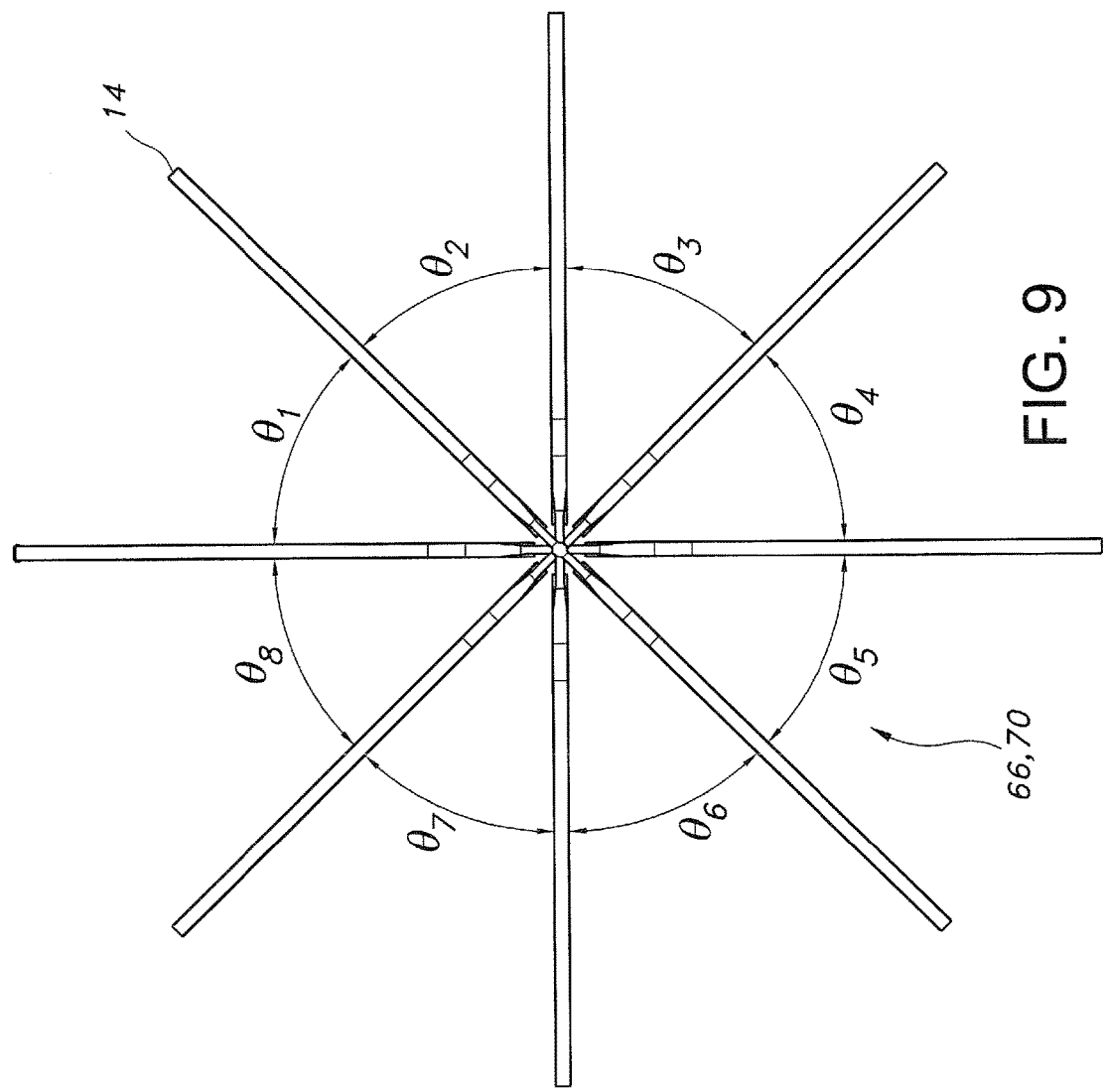
FIG. 9 is a right side view of the M-shaped basket embodiment of FIG. 7 depicting symmetric spline angles, according to the present invention.

FIG. 8 is a perspective view of the basket 12 of FIG. 7. Although eight splines 14 are depicted, the basket 12 of the present invention may have any useful number of splines. FIG. 9 is a right side view of the M-shaped basket embodiment of FIG. 7 depicting symmetric spline angles. As depicted in FIG. 9, the angles, θ1 through θ8, are all approximately equal at 45°. Such a relationship is a predetermined angular relationship to offer a symmetric or substantially symmetric basket 12 as viewed from a cross-sectional plane of the basket 12.

Figure 10:
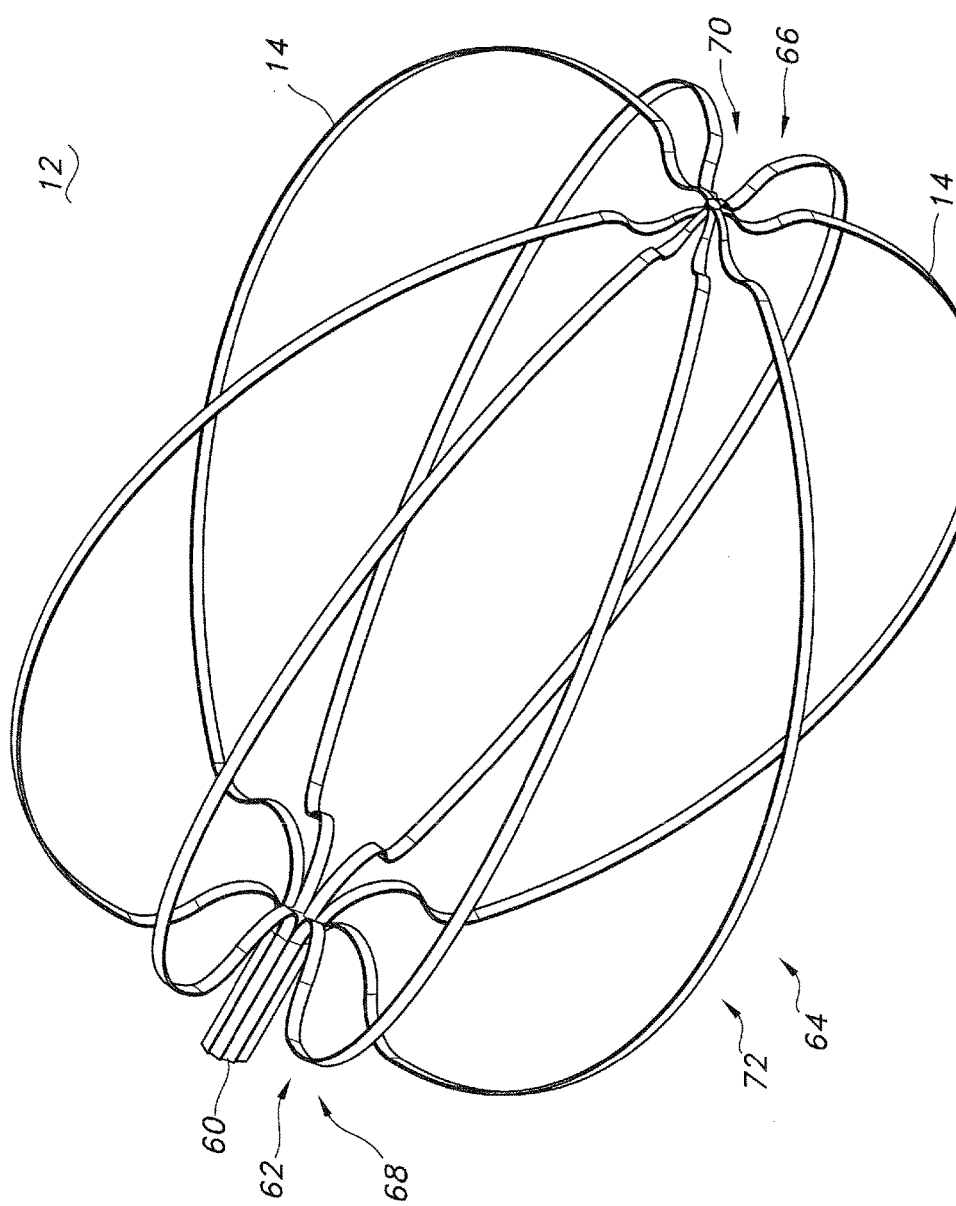
FIG. 10 is a perspective view of the basket of the system of FIG. 1 showing M-shaped, non-symmetric distal splines according to a basket embodiment of the present invention.
Figure 11:
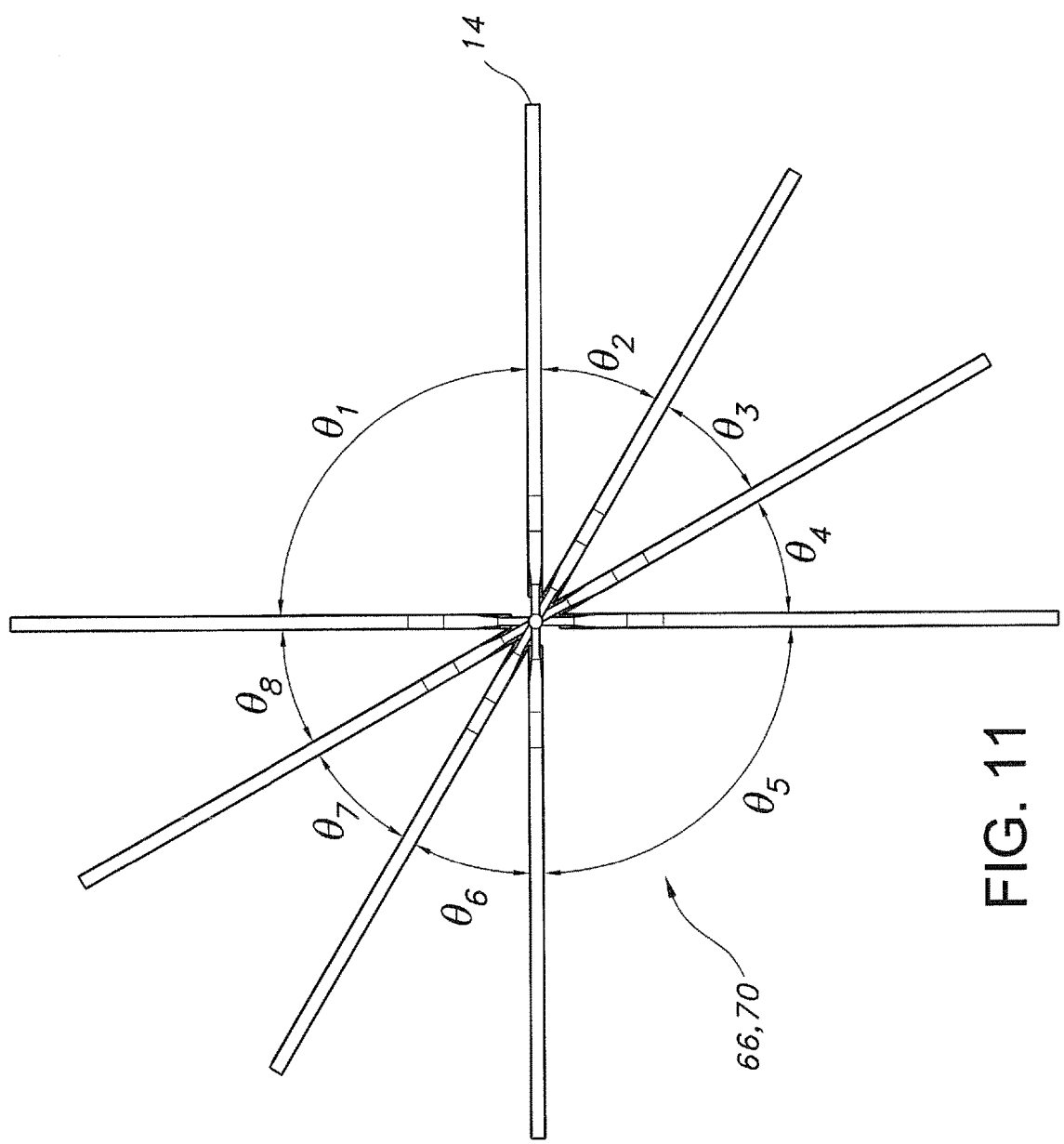
FIG. 11 is a right side view of the M-shaped basket embodiment of FIG. 10 depicting non-symmetric spline angles, according to the present invention.

The present invention, however, is not so limited. For example, as depicted in FIGS. 10 and 11, a predetermined angular relationship where the angles, θ1 through θ8, may vary may suitably be used. As depicted in FIG. 11, the angles θ1 and θ5 are approximately 90°, and the angles θ2 through θ4 and θ6 through θ8 are approximately 30°. These angles are non-limiting and any suitable arrangement of angles may be used. Such a non-symmetric angular relationship as depicted in FIGS. 10 and 11 may be useful, if desired, to concentrate a greater number of splines 14 at a particular location within the body, for example the right atrium of the heart.

Figure 12:
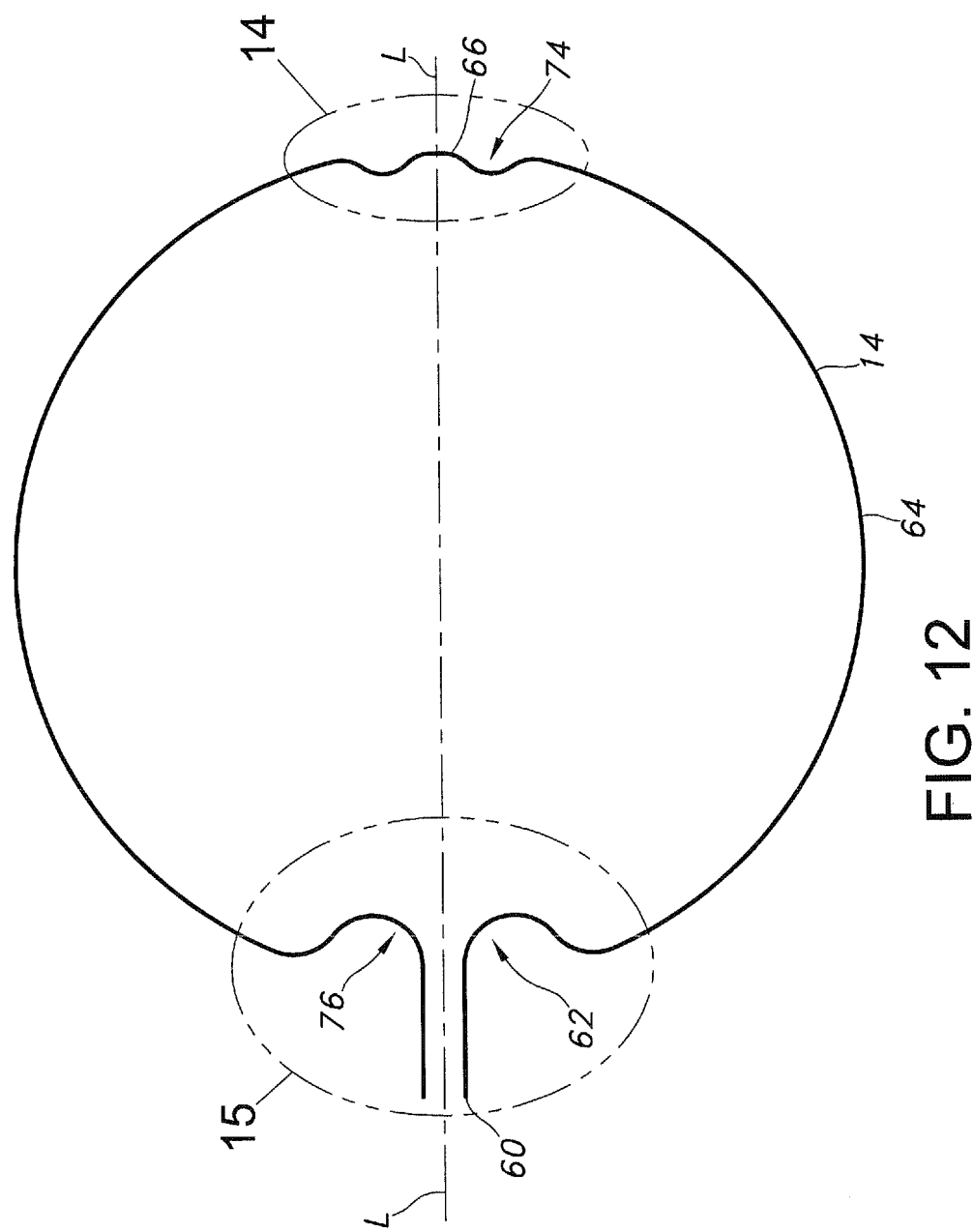
FIG. 12 a side elevational view of one of the splines of the M-shaped basket of FIG. 7 showing proximal spline recurves, according to the present invention.
Figure 13:
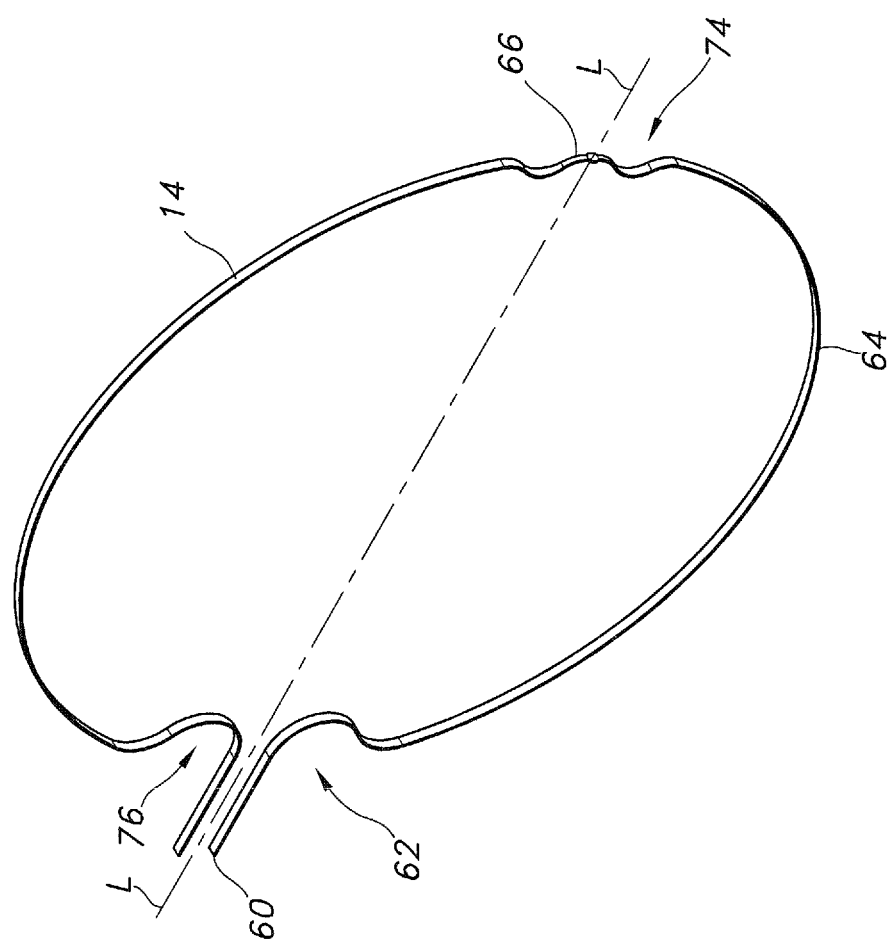
FIG. 13 is a perspective view of the spline of FIG. 12, according to the present invention.

FIG. 12 a side elevational view of one of the splines 14 of FIG. 7 showing the M-shaped distal curve 74 of basket 12 at the distal spline portion 66. The spline 14 also contains a proximal recurve 76 at the proximal spline portion 62. Further the spline 14 is also depicted as being symmetric in its expanded state about a longitudinal axis L, which is determined by the line segment axis from the proximal anchor 18 to the distal tip 16. FIG. 13 is a perspective view of the spline 14 of FIG. 12, further depicting the spline curvatures at the proximal spline portion 62 and the distal spline portion 66.

Figure 14:
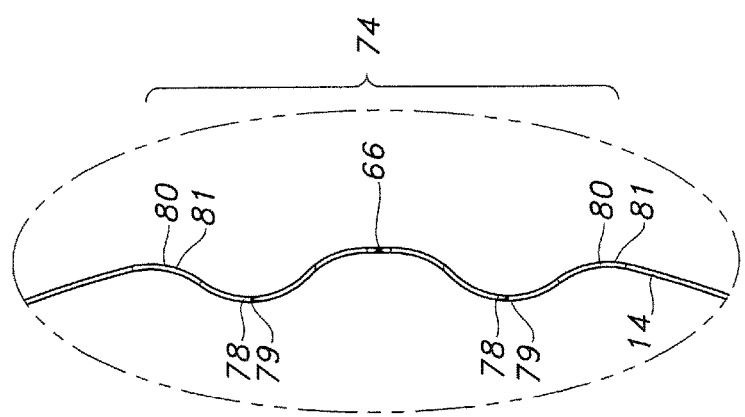
FIG. 14 is an exploded side view of a distal portion of the spline of FIG. 12, according to the present invention.

FIG. 14 is an exploded view of the distal M-shaped spline curve 74. The M-shaped spline curve 74 contains distal incurvate inward bends 78 and excurvate outward bends 80. Bend 78 is described as incurvate and/or inward because an apex 79 is directed towards the interior of the basket 12. Bend 80 is described as excurvate and/or outward because apex 81 is directed away from the interior of the basket 12. Bends 78 are useful in controlling angles from which splines 14 exit from or emerge into the distal tip 16, i.e., directed toward the exterior of basket 12. The bends 80 turn the splines 14 back in a proximal direction towards the proximal anchor 18.

Figure 15:
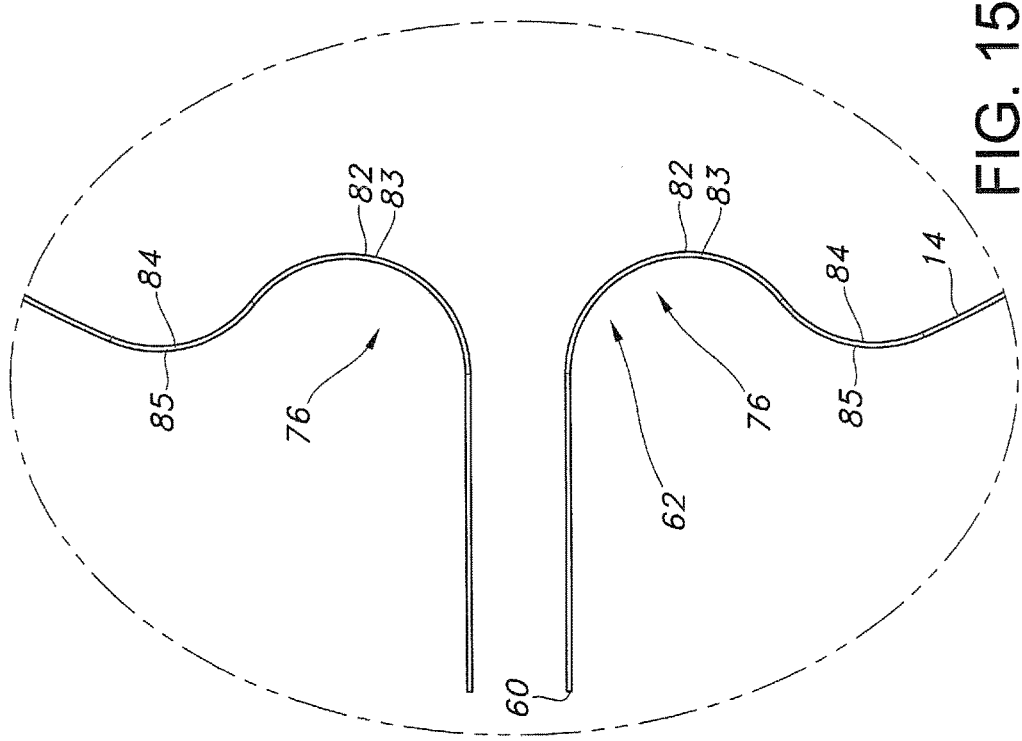
FIG. 15 is an exploded side view of a proximal portion of the spline of FIG. 12, according to the present invention.

FIG. 15 is an exploded view of the proximal spline portion 62 of the spline 14 of FIG. 12. The proximal spline portions 62 contain proximal recurves 76. The proximal recurves 76 include proximal incurvate bends 82 having apices 83 and proximal excurvate bends 84 having apices 85. The proximal recurves 76 impart several important features to the basket 12 of the present invention. The proximal recurves 76 allow for the geometry and flexibility of individual splines 14 to vary at the proximal end 62 which allows the basket 12 to become asymmetric and to better conform to the contours of the right atrium, as described in conjunction with FIG. 42A below. Further, the proximal recurves 76 allow for better placement of electrodes (not shown) at the proximal atrial tissue. Baskets common in the prior art do not often have good contact with proximal atrial tissue, thereby adversely effecting electrical activity detection thereat. Furthermore, the flexibility and geometry of the recurves 76 also permit enhanced electrode-tissue contact for the electrodes placed not only on the proximal spline portions 62, but also on the medial spline portions 64 and distal spline portions 66.

Figure 16:
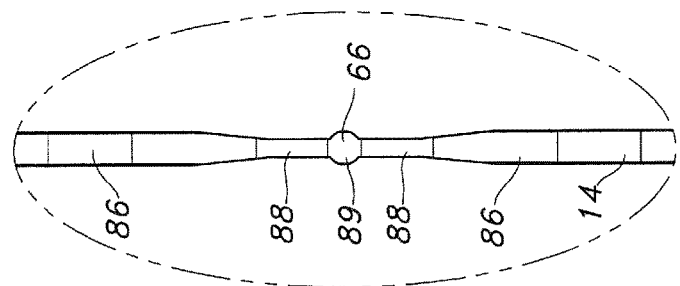
FIG. 16 is an exploded right side view of a portion of the distal portion of the spline of FIG. 12 showing a distal thinned portion, according to the present invention.

FIG. 16 is an exploded view of the distal spline portion 66. The splines 14 may contain portions of reduced spline widths 88 as compared to normal or non-reduced spline widths 86. Here the reduced spline widths 88 are depicted as being near the distal spline portion 66. Such reduced widths 88 may increase spline flexibility, as these spline portions are proximal to the distal tip 16 (not shown). The distal spline portion 66 may also include an alignment member 89 which, as described further below, is useful for aligning and/or securing the splines 14 within the distal tip 16 (not shown). The reduced width portions 88 at the spline distal portions also allows for less force to compress the basket 12, as depicted in FIG. 6, during removal of the basket 12 from the patient. Further, the reduced spline widths 88 aid in the basket 12 in achieving the substantially cylindrical shape, as depicted in FIG. 6. In other words, as compression of the basket 12 within a lumen 22, 48 goes from the medial basket portions 72 towards the distal basket portions 70, the reduced spline widths 88 allows the distal incurvate bends 78 to flex outward or away from the compression force so that the distal spline portions 66 do not retain the inward bends 78, or simply stated the bends 78 pop outward during radial compression of the basket 12. Another advantage of the distal M-Shaped spline curve 74 is that the distal tip 16 is directed towards the interior of the basket 12 when the basket 12 is deployed or is in its radially expanded state. This feature, if desired, keep the distal tip 16 away from distal heart tissue as the distal spline portions 66 may extend beyond the distal tip 16 in the longitudinal direction of the basket 14.

Figure 17:
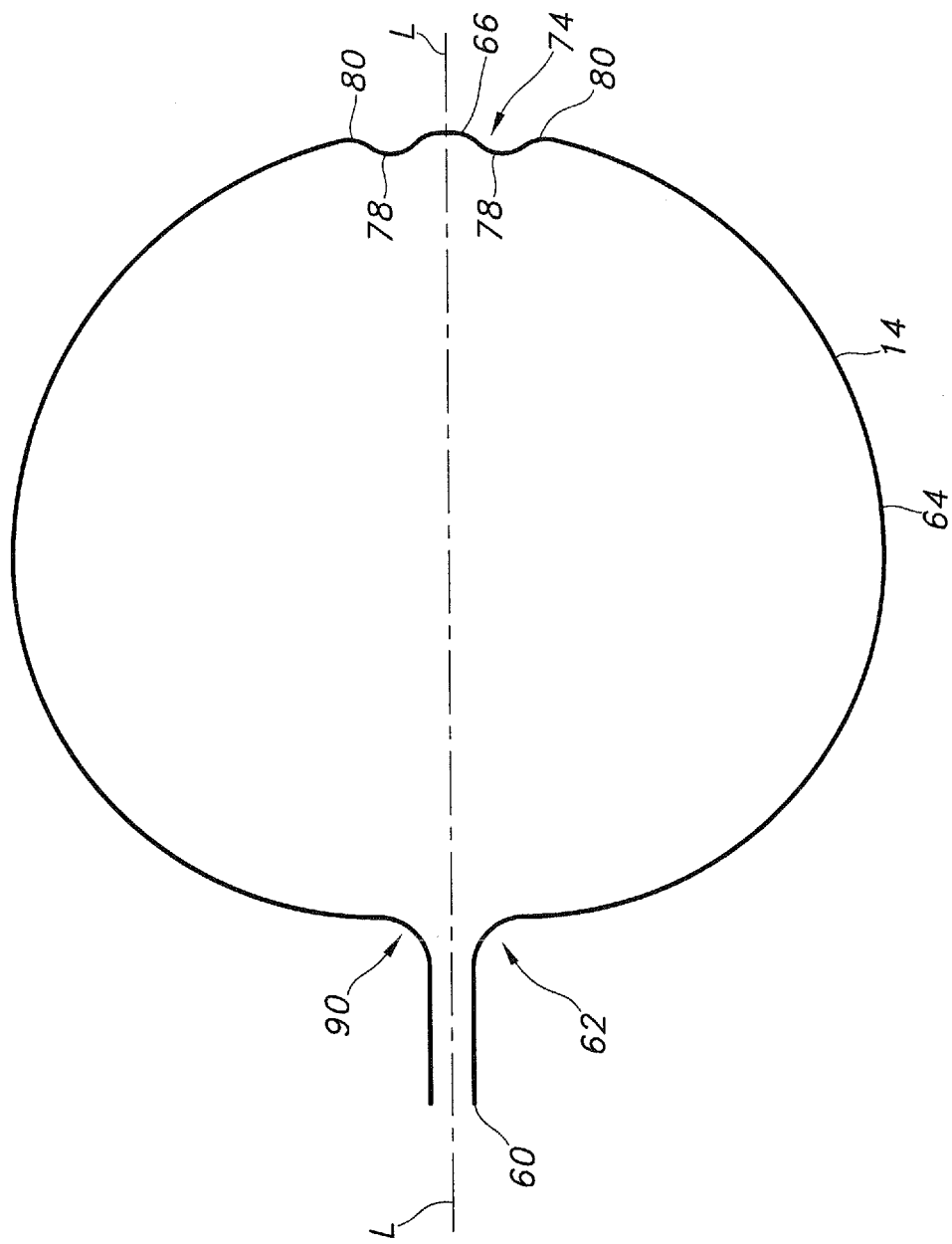
FIG. 17 is an expanded side view of another embodiment of a basket of the system of FIG. 1 showing M-shaped distal spline portion and proximal tangential spline curves, according to the present invention.

FIG. 17 is another embodiment of the spline 14 of FIG. 12. The spline 14 of FIG. 17 contains proximal tangential curves 90. While the tangential curve 90 may not offer the same degree of spline flexibility and basket stability as offered by the proximal spline recurve 76, such a proximal tangential curve 90 may be preferred by some practitioners in certain atrial procedures.

Figure 18:
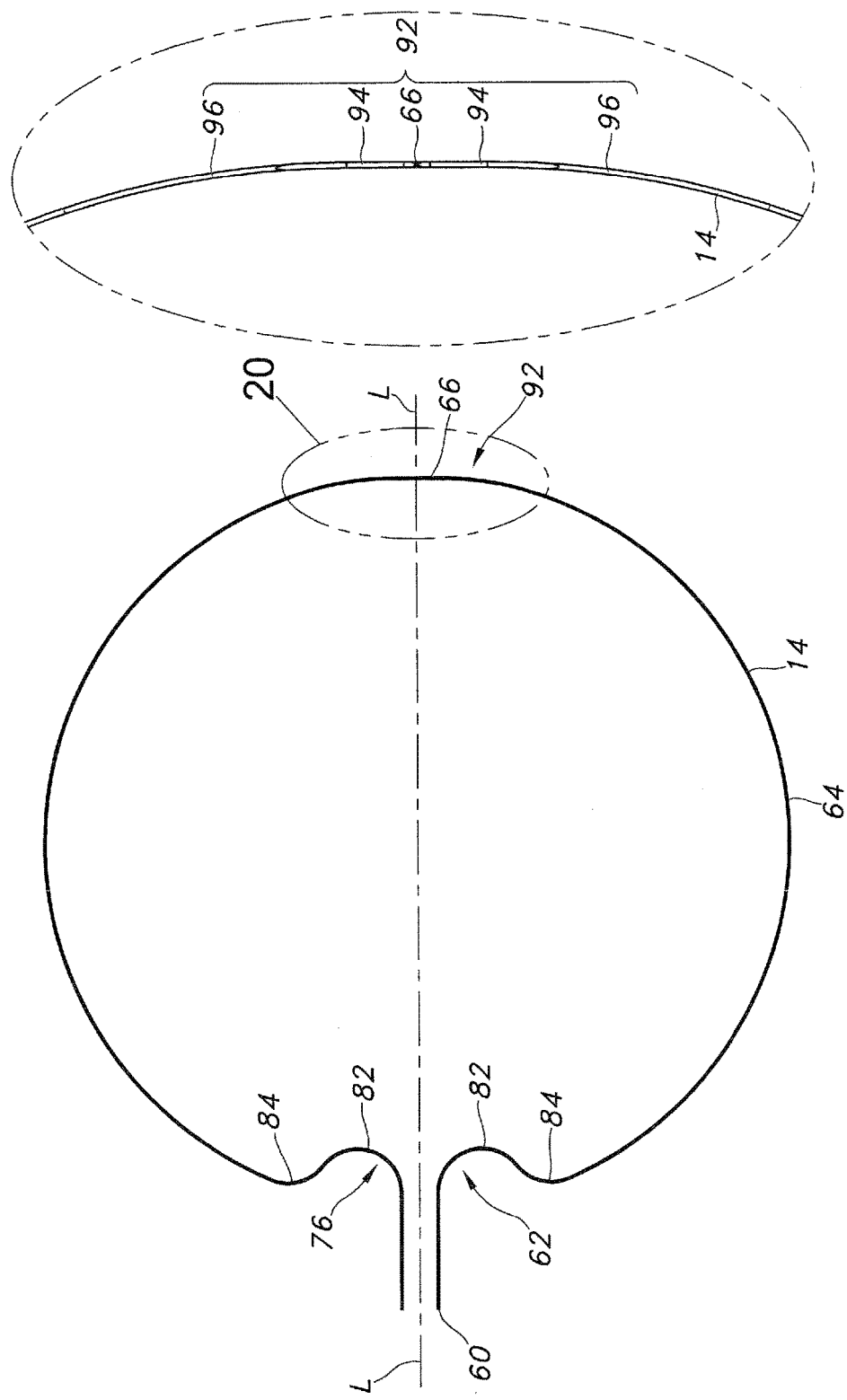
FIG. 18 is an expanded side view of another embodiment of a basket of the system of FIG. 1 showing a distal spline D-shaped curve and proximal recurves, according to the present invention.
Figure 19:
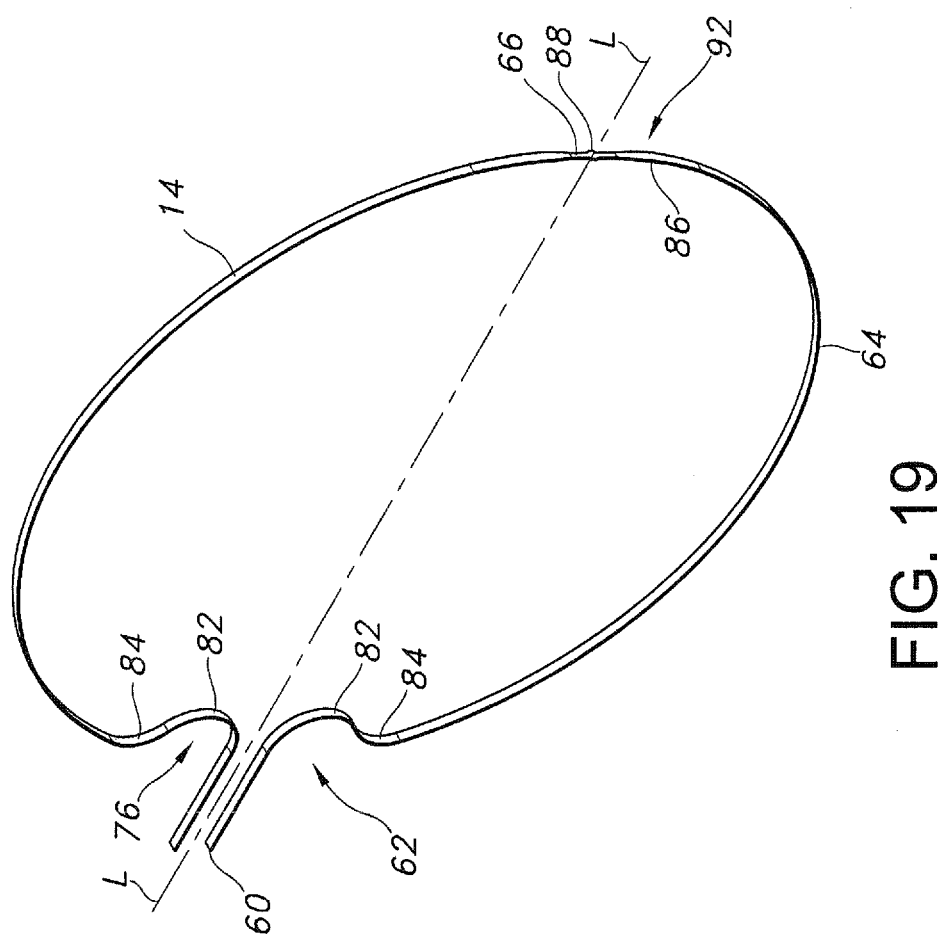
FIG. 19 is a perspective view of the spline of FIG. 18, according to the present invention.

FIG. 18 is a side elevational view of another spline 14 useful with the present invention. The spline 14 in FIG. 18 has a similar proximal spline recurve 76 as the spline 14 of FIG. 12. However, the spline 14 of FIG. 18 has a D-shaped 92 distal end portion 66. Such a D-shaped distal end 92 is useful with certain embodiments of distal tips 16 that are described below. FIG. 19 is a perspective view of the spline of FIG. 18 showing spline curvatures in further detail. FIG. 20 is an exploded view of the D-shaped spline portion 92 of FIG. 18. The distal spline portion 66 has substantially flat portions 94 followed by the curved portions 96. The curved portions 96 merge into the normal curvature of the overall basket shape. The substantially straight portion 94 are useful with certain distal tip 14 designs and where spline emergence or entrance angles at the distal tip 14 are desired to be about 90°.

Figure 21:
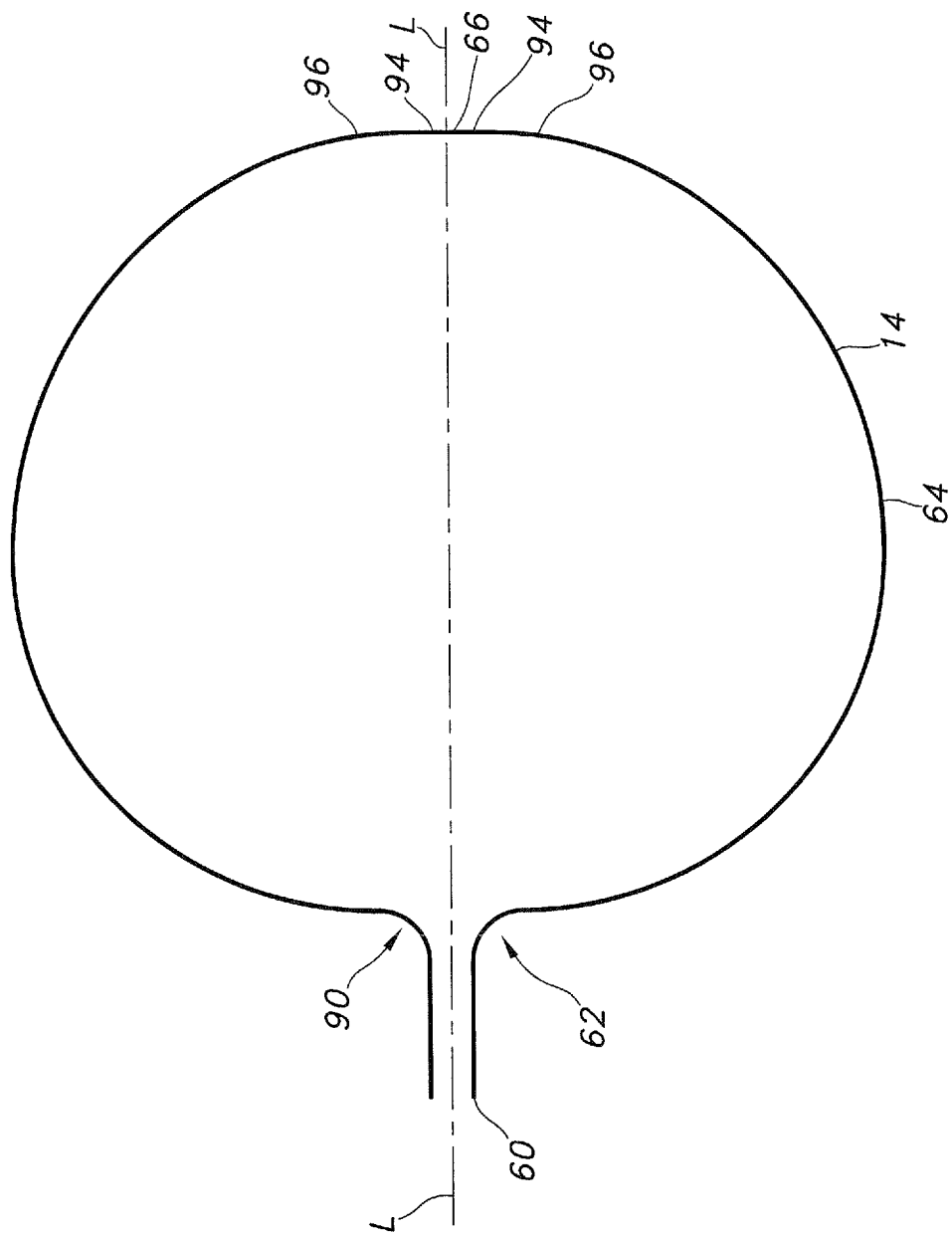
FIG. 21 is an expanded side view of another embodiment of a basket of the system of FIG. 1 showing a distal spline D-shaped curve and proximal tangential spline curves, according to the present invention.
Figure 22A:
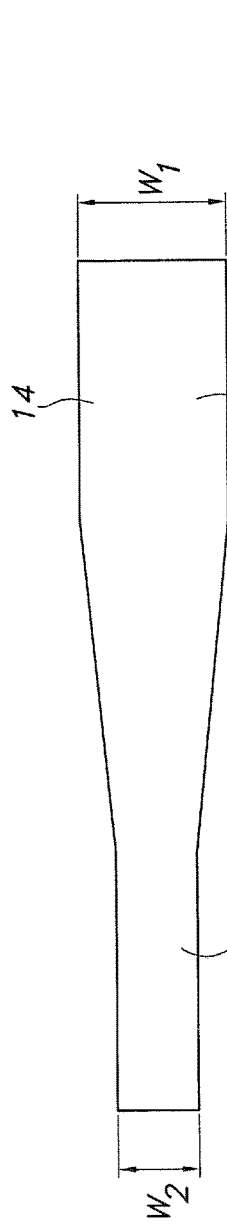
FIGS. 22A through 22D depict thinned side view spline portions, according to the present invention.
Figure 22B:
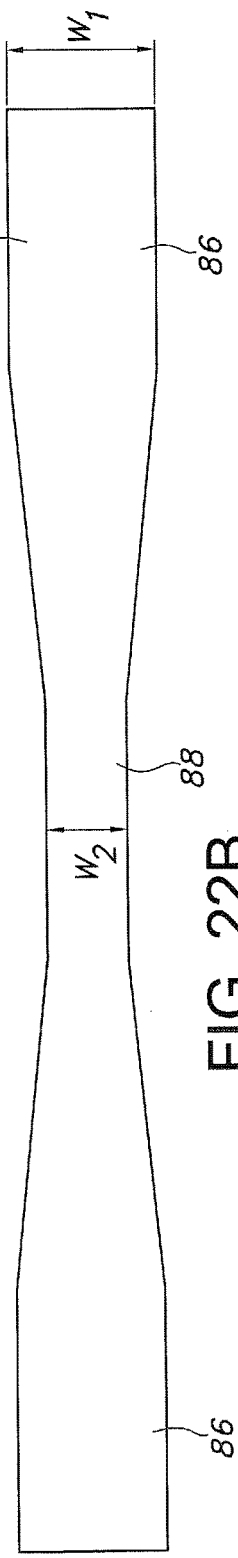
Figure 22C:
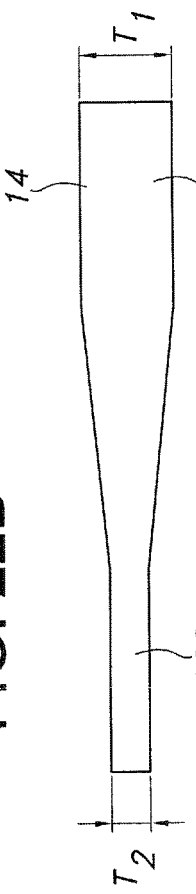
Figure 22D:
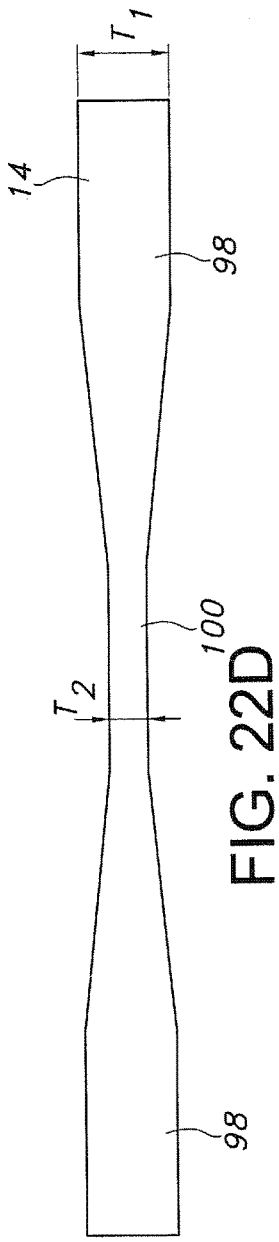

FIG. 21 depicts yet another spline 14 embodiment. The spline 14 of FIG. 21 contains D-shaped distal portions 94, 96 at the distal spline portion 66 and proximal tangential curves 90 at the proximal spline portion 62. Thus, the assembly 10 of the present invention may use any combination of the above-described spline geometries.

Splines 14 may be flattened splines through the body of the spline 14 having a substantial rectangular shape with rounded sides (see, e.g., FIG. 34C). Throughout at least a major portion of the splines 14, the splines 14 may be about 0.013 to about 0.035 inches wide (W1) and about 0.002 to about 0.012 inches thick (T1), as depicted in FIGS. 22A through 22D. A preferred width (W1) is about 0.022 inches. Spline thickness (T1) may depend on the overall size of the basket 12 with small sized baskets, for example less than 60 mm in nominal diameter, the thickness may range from about 0.002 inches to about 0.010 inches, with 0.004 inches being preferred. For larger size baskets, for example greater than 60 mm in nominal diameter, the thickness may range from about 0.002 inches to about 0.012 inches, with 0.006 inches being preferred. These dimensions are not limiting and represent normal or typical spline width portions 86 and spline thickness portions 98.

Some portions of the splines 14 may have reduced with portions 88 and/or reduced thickness portions 100. Typically, these portions 88, 100 are disposed at distal spline portions 66 near or at the distal tip 16. However, the present invention is not so limited at these reduced portions 88, 100 may be present in proximal spline portions 62 and medial spline portions 64. The thinned spline portions 88, 100 may have a reduction in width and or thickness of several thousands of an inch. For example, the thickness (T2) of certain spline portions 100 may be thinned down to several thousands of an inch or to a thickness of about 0.003 inches to 0.004 inches, or less. Such thinning of the distal spline segments 66 near the membrane tip 14 reduces stresses during capture of the splines 14 within the guide catheter 34.

Low stress is an advantageous feature during collapse for introduction, repositioning and withdrawal of the spline basket. The width (W2) of the narrowed spline segments 88 may be narrowed from about 0.013 to 0.035 inches to about 0.008 to 0.014 inches. Such thinning aids the splines 14, when they fold up or collapse into the guide catheter 34, to overcome their tendency to push themselves apart and avoid them occupying more space in the catheter 34. Thus, a low profile catheter system 10 may be provided according to the present invention.

FIGS. 23A and 23B depict a spline portion, such as spline portion 86, having a buckle point 102. The buckle point 102 may be ground into the spline 14 or formed by any other suitable technique. The buckle point 102 is depicted as an inwardly curved notch, but other designs may suitably be used. As depicted in FIGS. 23A and 23B, the buckle points 102 provide the splines 14 with curvature inflection points, which provide the basket 12 with improved matching of the contours of the interior of the heart. The buckle points 102 may be disposed at any location along the proximal spline portions 62, the medial spline portions 64 and/or the distal spline portions 66 shown in FIG. 21. Further, the number or frequency of buckle points 102 may also vary.

As depicted in FIGS. 24 and 25, the splines 14 may emerge from the distal tip 16 at any useful emergence angle, a, with respect to the longitudinal axis L, which is defined by a line segment from the proximal anchor 18 to the distal tip 16. For example, as depicted in FIG. 24, the emergence angle α may be about 45° or less than about 45°. As depicted in FIG. 25, the emergence angle α may be about 90°. The splines 14 may include a bend 78 which is useful for, among things, controlling the shape of the expanded splines 14 or basket 12. The distal tip 16 shown in FIGS. 24 and 25 is merely a schematic depiction of a general tip. Any of the below-described distal tips of the present invention may be used with any of the emergence angles described in conjunction with FIGS. 24 to 25. The angles are non-limiting, and any suitable emergence angle or combination of emergence angles may be used.

Figure 26B:
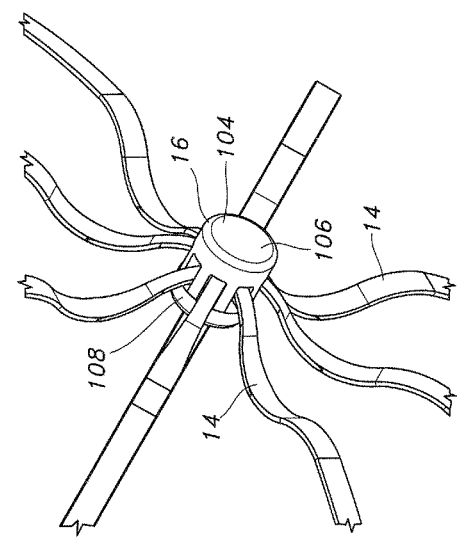
FIG. 26B is a rear perspective view of the distal tip of FIG. 26A, according to the present invention.
Figure 26A:
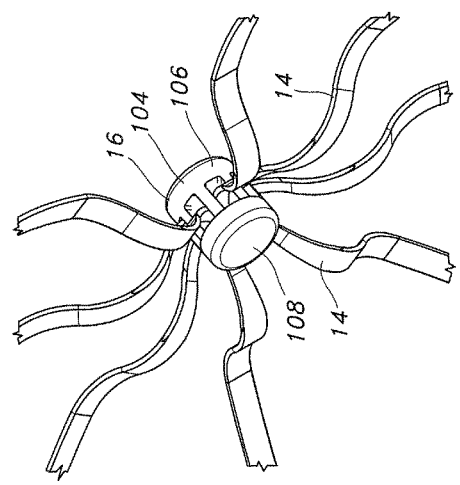
FIG. 26A is a front perspective view of a two-part, welded distal tip, according to the present invention.
Figure 26E:
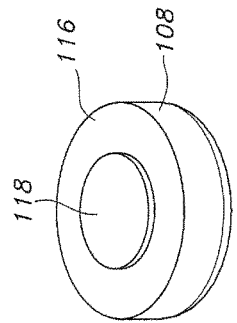
FIG. 26E is a front perspective view of a bottom top part of the distal tip of FIG. 26A, according to the present invention.
Figure 26D:
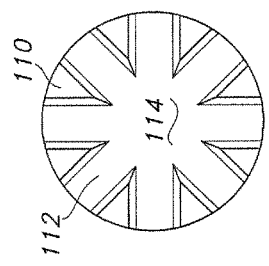
FIG. 26D is a bottom view of the top part of the distal tip of FIG. 26A, according to the present invention.
Figure 26C:
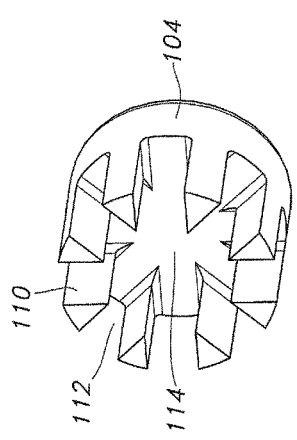
FIG. 26C is a front perspective view of a top part of the distal tip of FIG. 26A, according to the present invention.
Figure 26F:
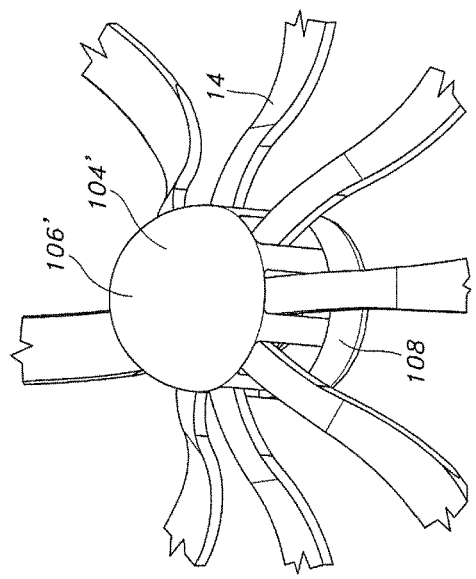
FIG. 26F is a front perspective view of another embodiment of a two-part, welded distal tip having a rounded or domed upper portion, according to the present invention.

FIGS. 26A through 26F depict a two-part welded distal tip 16, according to the present invention. FIG. 26A is a front perspective of distal tip 16; FIG. 26B is a back or rear perspective of distal tip 16; FIG. 26C is perspective view of a top part of the distal tip 16; FIG. 26D is a bottom view of the top part of the distal tip 16; FIG. 26E is a top perspective view of the bottom part of distal tip 16; and FIG. 26F depicts an alternate embodiment of the distal tip 16.

As depicted in FIGS. 26A through 26E, distal tip 16 may include a top part 104 and a bottom part 108. The distal portions 66 of the splines 14 are securably disposed within the distal tip 16. The top surface 106 of the top part 104 may have any suitable shape, such as a substantially flat surface 106 with rounded edges so that the distal tip 16 is an atraumatic tip, i.e., a tip that will not cause damage to atrial tissue. The bottom part 108 likewise should be free of any sharp edges or projections to avoid atrial tissue damage. The top part 104 and the bottom part 108 are secured to one and the other by any suitable means. One non-limiting means and useful means is welding the two parts together to provide a unitary distal tip 16. Such securement is typically performed after proper placement of the distal spline portions 66 within the distal tip 16.

As depicted in FIGS. 26C through 26D, the top part 104 of the distal tip 16 may include spline alignment posts 110. The spline alignment posts 110 are spaced apart so that the splines 14 may fit between the spline alignment channels 112. The spline alignment posts 110 do not extend completely into the center of the distal tip 16, but terminate to provide a center spline alignment portion 114 of the top part 104 of the distal tip 16. The center spline alignment portion 114 is useful for receiving the spline alignment members 89 of the distal portions 66 of the splines 14 into that region 114 of the distal tip 16. The combination of the center spline alignment portion 114 and the spline alignment channels 112 provide for, among other things, securably holding the splines 14 in any desired predetermined angular relationship. The number of spline alignment posts 110 may vary as the number of splines 14 may vary within the distal tip 16. The bottom part 108 of the distal tip 16 may contain flat top and inner surface 116. The surface 116 may generally correspond to the bottom surfaces of the spline alignment posts 110. The bottom part 108 may also include a raised central; portion 118. Desirably this raised central portion 118 is substantially flat. The raised portion 118 is sized so that it can be disposed within the center spline alignment portion 114 of the top part 104 of the distal spline 16.

While the splines are securably held within the distal tip 16, the spline alignment channels 112 allow some movement of the spline 14. For example, spline portions may move upward and or downward with the spline alignment channel 112 to provide flexibility of the splines 14 at the distal tip 16. If desired, an elastomeric material may also be placed within the two-part distal tip 16 to minimize tip voids and open spaces.

As depicted in FIG. 26F, the two-part distal tip 16 may include a rounded or domed upper 106' of the top part 104'. Such a rounded or domed design may be useful in providing more rounded surfaces for the atraumatic distal tip 16.

The distal tip 16 of FIGS. 26A through 26F may be made of any suitable biocompatible material. Although metal materials are preferred, plastic materials may be used.

Figure 27B:
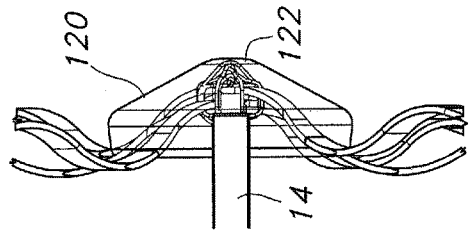
FIG. 27B is a side elevation view of the distal tip of FIG. 27A, according to the present invention.
Figure 27A:
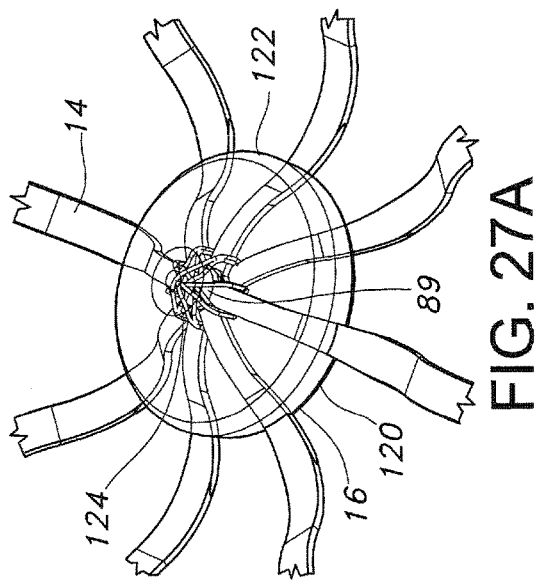
FIG. 27A is a front perspective view of an encapsulated, filament wound distal tip, according to the present invention.
Figure 27C:
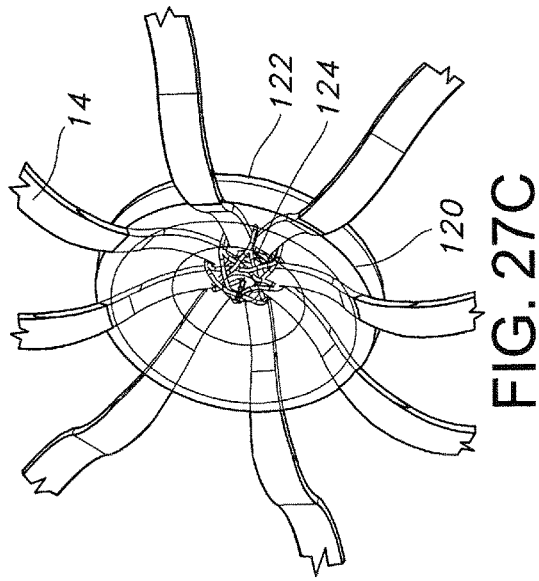
FIG. 27C is a rear perspective view of the distal tip of FIG. 27A, according to the present invention.
Figure 27E:
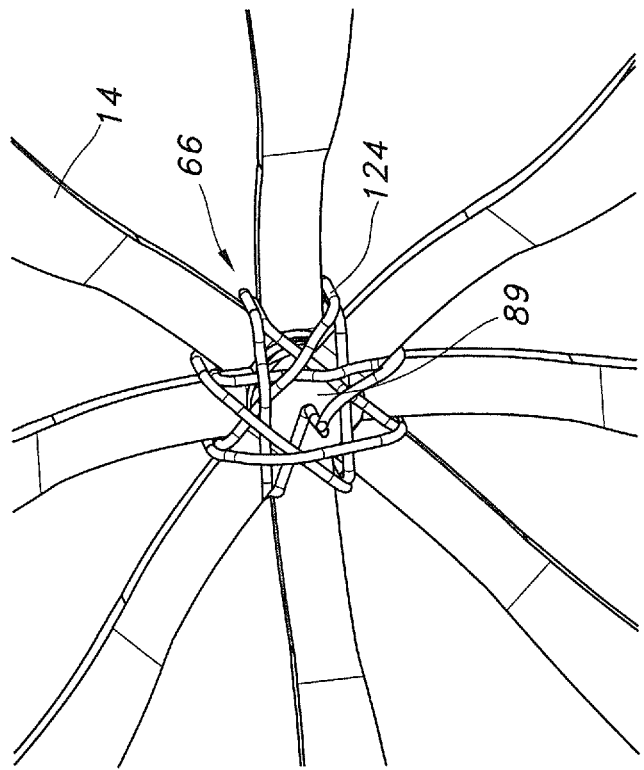
FIG. 27E is a rear perspective view of the filament wrapping of the distal tip of FIG. 27A, according to the present invention.
Figure 27D:
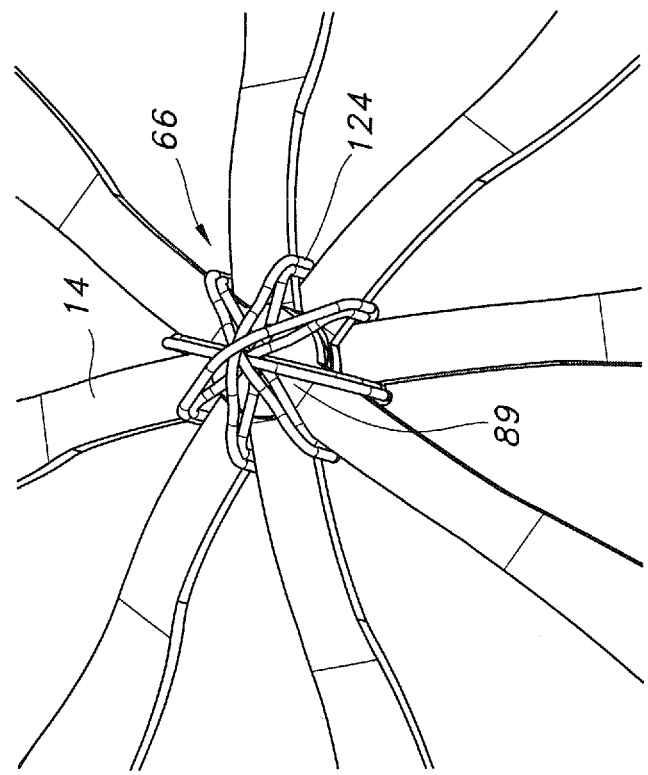
FIG. 27D is a top perspective view of the filament wrapping of the distal tip of FIG. 27A, according to the present invention.

FIGS. 27A through 27C depict an alternate embodiment of the distal tip 16 of the present invention, i.e., a filament wound and encapsulated distal tip 120, in which FIG. 27A is a front perspective view of the filament wound and encapsulated distal tip 120; FIG. 27B is a side view of the filament wound and encapsulated distal tip 120; and FIG. 27C is a back or rear perspective view of the filament wound and encapsulated distal tip 120. FIGS. 27D and 27E are exploded views of the filament wrapping for the filament wound and encapsulated distal tip 120, in which FIG. 27D is a top perspective view thereof and FIG. 27E is a back or rear perspective view thereof. The filament 124 is wrapped over, under and between the splines 14 and over and under the spline alignment members 89 to secure the splines 14 in any desired predetermined angular relationship.

The splines 14 are secured to each other at the filament wound and encapsulated distal tip 120. Tip 120 may be described as being a "filament wrapped and encapsulated" or a "suture wrapped and encapsulated" tip 16. Tip 120 is not limited to the use of suture materials and any suitable filaments, threads, wires and the like may be suitably used. Advantageously, the filament wound and encapsulated distal tip 120 is a low profile tip. Further, filament wound and encapsulated distal tip 120 has no open spaces, such as slots or holes, common with some basket catheters of the prior art. Such open spaces or holes present in tips of the prior art allow for entry of blood cells, thereby causing or having the potential to cause blood clot formation or thrombogenesis. As described below, the splines 14 are secured to each other at their circular alignment members 89 by the use of a suture(s) 124, filament(s) 124, wire(s) 124 or thread(s) 124. Multiple sutures 124, filaments 124, wires 124 or threads 124 may be used. After the splines 14 are so secured, the circular alignment members 89 of the splines 14, including the securing suture(s) 124, filament(s) 124, wire(s) 124 or thread(s) 124 are fully or substantially or partially encapsulated with an encapsulant 122 to provide the filament wound and encapsulated distal tip 120.

As depicted in FIGS. 27D and 27E, the circular tip spline alignment portions 89 of the splines 14 are aligned or substantially aligned with each other. Filaments(s) 124 are laced, looped or wound between, over and under the splines 14 at the circular tip spline alignment portions 89. A single filament or multiple filaments 124 may be used. Advantageously, the filament(s) 124 is laced, looped or wound between every adjacent spline portion. As depicted in FIGS. 27D and 27E, the filament(s) 124 is laced, looped or wound about opposite spline intersections or alternating spline intersections and then is crisscrossed in a similar fashion until all or substantially all of the spline intersection locations are secured.

The filament 124 may include any suitable material. The use of high tensile strength fibers, such as electrospun, braided or monofilament may be used. Some non-limiting examples include, but are not limited to, for example: Dyneema Purity® (Ultra High Molecular Weight Polyethylene or UHMWPE), Spectra® fiber (UHMWPE), Polyethyleneterephthalate or PET, polypropylene, etc. Metallic wires, such as stainless steel or nitinol, may also be used, but non-metallic fibers are preferred for their greater flexibility. The filament(s) 124 may be tied or twisted together to secure the circular tip or alignment portions 89 of the splines 14. The filament(s) 124 may be twisted or tied together at locations interior to the spline basket 12. The tied together circular tip or alignment portions 89 and the filament(s) 124 are then encapsulated with an encapsulant 122. One useful encapsulant 122 is polyurethane, but other biocompatible encapsulants may suitably be used. The encapsulant 122 is also disposed between the spline intersection points to provide the tip 120 of the present invention.

Some advantages of the filament wound and encapsulated distal tip 120 of the present invention include, but are not limited to improved flexibility over tips of the prior art; reduced thrombogenicity; significantly smaller overall tip size; transparency under fluoroscopy; no MR artifacts; superior strength, i.e., equal to or greater than 15 times the strength of steel of the same diameter; superior adhesive bond strength; resistance to cutting (scissor action); and very small diameters, as low as 25 decitex (dtex).

As depicted in FIGS. 27A through 27C, the filament wound and encapsulated distal tip 120 has an atraumatic profile with a smooth, somewhat rounded upper surface, an inwardly contoured bottom surface and smooth side surfaces. The amount of encapsulant 122 may be minimized to provide maximum spline flexibility.

FIG. 28A depicts another embodiment of the distal tip 16 in which two-part welded distal tip 126 with half splines is provided. As depicted in FIG. 28A, two-part tip 126 includes a top portion 128 insertable through a bottom portion 130. A space or detent is provided in either or both portions 128, 130 so that distal ends 67 of the splines 14 may be securably inserted therein. The portions 128, 130 of the two-part tip 126 are securably joined together to securably affix the distal spline ends 67 therein. The portions 128, 130 of the two-part tip 126 may be secured to each other by spot welds 132, but other securing techniques may suitably be used. Although the splines 14 are depicted as emerging from the sidewall of the two-part tip 126, the present invention is not so limited. If desired, the splines 14 may emerge from the top portion 128 (not shown) and/or the bottom portion 130 (not shown).

The emergence angle of the splines 14 from the two-part tip 126 may include any of the above-described emergence angles. The splines 14 depicted in FIG. 28A may be referred to as half-splines because these splines have both distal spline ends 67 and proximal spline ends 60.

FIG. 28B depicts another embodiment of the distal tip 16, in which a nitinol shrink ring tip 134 according to another aspect of the present invention. Spline ends 67 may be disposed within the tip 134. The tip 134 has a compression ring 138 and a core post 136. The spline ends 67 are disposed within and secured by the tip 134. The ring 138 may be made from metallic, nitinol shape memory metal, shrink tubes. It may be machined at room temperature to design specifications, and then chilled so it can be expanded and stored. One may slip the ring 138 over the mated spline ends 67 and post 136 and assemble quickly. As the ring 138 comes up to room temperature it shrinks and provides a very strong compression fitting to secure the spline 14 within the tip 134.

FIG. 28C depicts a tip 140 which may also be used with the present invention. A cap 144 and a base 146 may be secured to each other, by for example spot welding, via a square rivet 142. The square rivet 142 is passed through alignment square holes 148 punched in splines 14, as depicted in FIG. 28D. The splines 14 do not directly pass through the distal tip members 144, 146. In other words, the splines 14 do not pass through a sidewall of tip 140, as no sidewall is present between the distal tip members 144, 146.

In another embodiment of the present invention, the tips of the present invention may include a magnetic tip (not shown). With previously described constraining tips spline lengths should be about identical in order for the basket to collapse evenly into guide catheter. If atrium outline shape deviates from approximately cylindrical or oval, then equal length splines may not contact all endocardial surfaces. A way to circumvent this problem is to allow the splines to be of different lengths (to match the atria), and allow the tip to "assemble" itself in situ when deploying. The tip may also "disassemble" itself when being captured into the guide catheter. This design may be achieved by using a small magnetic portion on each spline that "self assemble" themselves into a tip when deployed from the guide catheter, and disassemble themselves (i.e., magnets pull apart) when the basket is collapsed into the guide catheter. It may be necessary to place an elastic thread between each magnet, pulling them close enough for magnetic force to pull into assembly. If the splines follow the inside wall of the heart during diastole, then the splines need to buckle or deform during systole. The buckling will bring parts of the spline out of contact with the endocardium. Deformation will move the electrodes to different locations on the endocardium, confusing the mapping software. Note that, during atrial fibrillation, the heart remains close to its diastolic dimensions during its entire contraction cycle. This reduces the significance of this effect, making the basket design easier. In order for the basket to collapse into the guide catheter the splines need to be the same length but would need to be different lengths in order to follow locally distended parts of the atrium. A magnetic tip would disassemble as the catheter goes into the guide catheter. An elastic thread could be used between them so that the magnetic field then grabs them the rest of the way.

Figure 29:
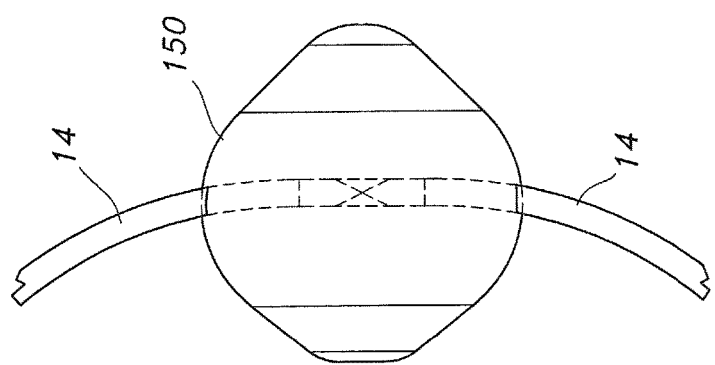
FIG. 29 is a side elevational view of an encapsulated distal tip, according to the present invention.

FIG. 29 depicts another embodiment of a distal tip 16, in which an encapsulated tip 150 is provided. The encapsulated tip may include any suitable flexible and/or elastomeric material. The overall profile of the tip 150 may be larger than for the filament and encapsulated tip 120 as tip 150 may not contain any filament wrapping or securement means. The encapsulated or molded tip 150 may be made from any suitable material. In one embodiment of the present invention, the encapsulated or molded tip 150 may be made from polyurethane, polyester block amide or silicone.

Figure 30A:
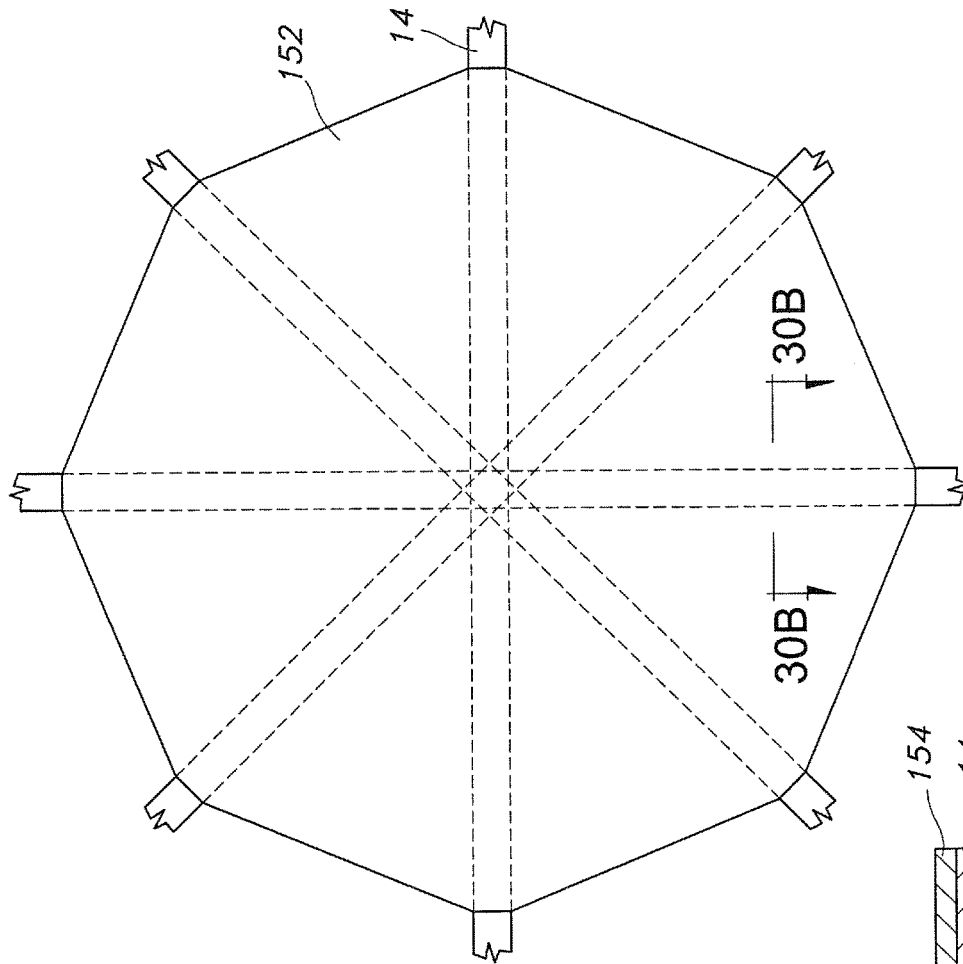
FIG. 30A is a top view of a membrane distal tip, according to the present invention.
Figure 30B:
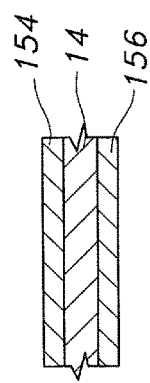
FIG. 30B is a partial cross-sectional view of the membrane tip of FIG. 30A.

FIGS. 30A and 30B depict another embodiment of the distal tip 16, in which a membrane distal tip 152 is provided. The membrane tip 152 may include an inner membrane or film 156 and an outer membrane or film 154 for securing the distal portions 66 of the splines 14. The distal portions 66 of the splines 14 may simply cross each other between the two membranes 154, 156. The membranes 154, 156 may be bonded, for example adhesive bonding, thermal bonding, and the like, together to provide the membrane tip 152.

The splines 14 may simply cross within the membrane tip 152. No separate connection between the splines 14 within the membrane 152 is needed. If desired, a connection (not shown) between the splines 14 may be provided. The inner membrane 156 and the outer membrane 154 may be adhesively bonded to all splines 14 within the membrane tip 152. Further, the inner membrane 156 and outer membrane 154 may be adhesively bonded to each other at locations between the splines 14. All elements may then be placed into fixture (not shown) so as to ensure the proper linear and angular orientation of the elements and then heat bonded together.

The present invention is not limited to the use of the inner membrane 156 and outer membrane 154 to form the membrane tip 152. Additional membrane layers or films may be used. The membrane tip 152 may have any suitable shape, for example a circular shape, an octagonal shape, and the like. Further, matched diameter adhesive pads (not shown) may be placed between splines 14 to add additional support beyond just membranes 154, 156. The adhesive pads between the splines 14 at the membrane tip 152 may fill in gaps between splines 14, thereby providing a slightly larger area for adhesive bonding, if desired. Thus, in either embodiment the width and/or thickness of the tip membrane 152 is minimal, i.e., less than the thickness of the splines 14, or about the same thickness of the splines 14 or even just slightly larger than the thickness of the splines 14. In any case, the tip membrane 152 does not have an appreciable sidewall as compared to the tips of the prior art.

Further, the tip membrane 152, including the inner membrane 156 and outer membrane 154, may be made from any suitable polymeric material, preferably non-elastic polymeric material, including flexible non-elastic polymeric material. In one embodiment the membranes 154, 156 may be made from a polyimide material. Desirably, the membranes 154, 156 are not made from polytetrafluoroethylene, i.e., PTFE, including expanded polytetrafluoroethylene, i.e., ePTFE.

Figure 31B:
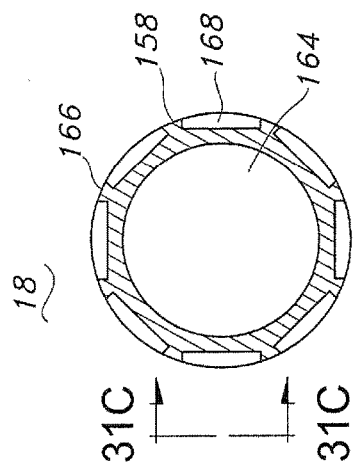
FIG. 31B is a right cross-sectional view of the slotted anchor of FIG. 31A, according to the present invention.
Figure 31D:
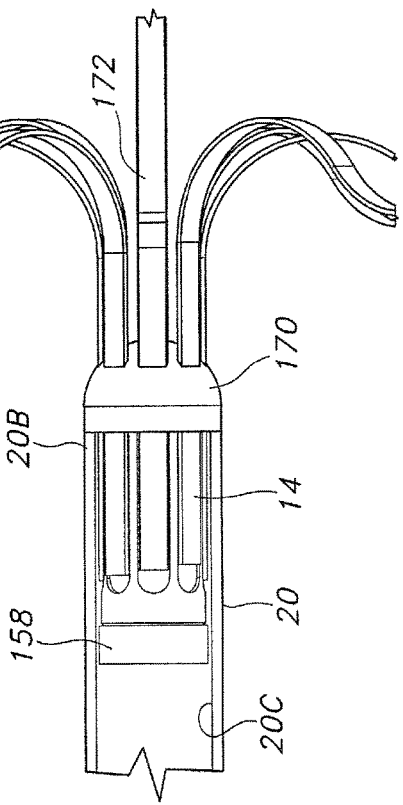
FIG. 31D is a partial cross-sectional view of the slotted anchor of FIG. 31A securable disposed with a portion of the catheter body of the system of FIG. 1, according to the present invention.
Figure 31A:
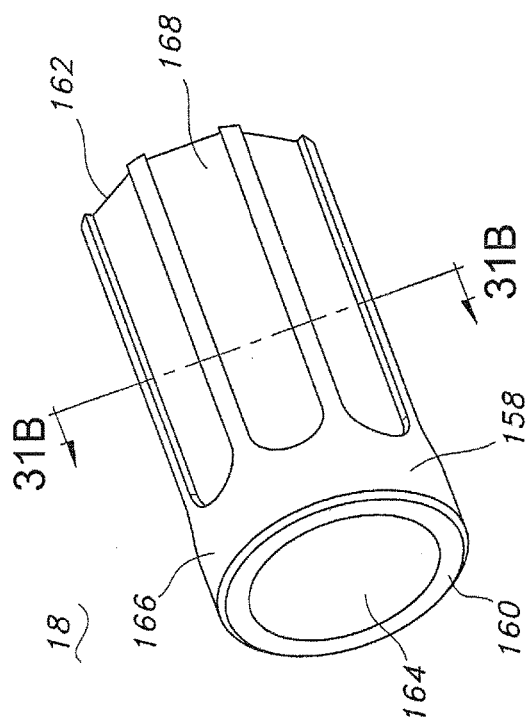
FIG. 31A is a perspective view of a slotted proximal anchor, according to the present invention.
Figure 31C:
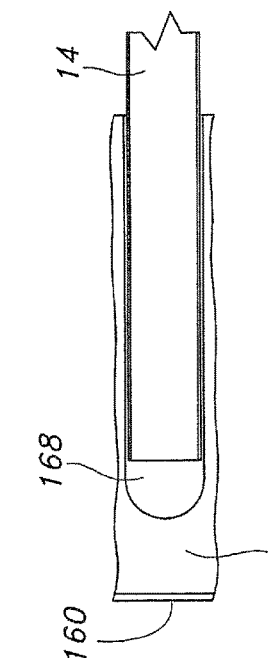
FIG. 31C is an exploded, partial side elevation view of the slotted anchor of FIG. 31A, according to the present invention.

FIGS. 31A through 31D depict an embodiment of the proximal anchor 18 of the present invention, in which a slotted proximal anchor is provided. FIG. 31A is a perspective view of the proximal end 160 of the slotted anchor 158. FIG. 31B is a cross-section view of the distal end 162 of the slotted anchor 158 taken along the 31B-31B axis. Slotted anchor 158 has an open diameter or open lumen 164. The open diameter or lumen 164 allows wires, flex circuits, etc. from the spline basket 12 to pass through the anchor 158. The proximal end 160 of the slotted anchor 158 presses into an inner diameter or lumen of a catheter shaft 20C or is otherwise connected to the catheter shaft 20. Anchor 158 also includes spline-receiving slots 168. The number of spline-receiving slots 168 typically is equal to the number of proximal spline end portions 60, and is shown in these drawings as a quantity of eight. As depicted in FIGS. 31A and 31B, the spline-receiving slots 168 may be evenly spaced to allow for the basket splines 14 to be equally spaced in the desired angular position. The present invention, however, is not so limited, and any number of proximal spline end portions 60 and spline-receiving slots 168, oriented at any desired relative angles may suitably be used.

One function of the anchor 158 is to attach the basket splines 14 to the catheter 20 and orient the splines 14 to give the basket 12 the proper shape and ensure it remains straight (not bent) upon collapse into the guide catheter 46. The anchor device 158 is a means by which to orient the basket splines 14 on the proximal end 68 of the spline basket 12 and to fasten them together. Additionally, the anchor 158 affixes the basket splines 14 to the catheter shaft 20. The anchor 158 may be fabricated from a single piece of material, e.g., a hypotube, or multiple sections that are attached (i.e. welded, glued, etc.) together. The slots 168 are sized to fit the basket splines 14 and the slot length ensures splines 14 are positioned accurately, which aids in even collapsing of the basket 12. The slots 168 have adequate length to allow for the variable positioning of the basket splines 14. The basket splines 14 may be attached to the anchor 158 by adhering with glue, welding, crimping or the like. Additionally, a ring (not shown) may be slid over the anchor 158 to hold the basket splines 14 in place. The outer ring (not shown) may be crimped, swaged, welded, glued, etc. to the outside 166 of the anchor 158 or the outside of the catheter shaft 20. The angular spacing of the slots 168 may be varied to accommodate the amount or number of basket splines 14 to be attached as well as to get the desired spacing of basket splines 14. As depicted in FIG. 31B, one typical angular spacing is 45° degrees. The proximal end 160 of the anchor 158 is sized to press fit into a catheter shaft. It can be changed to accommodate any desired catheter dimensions. Additionally, the proximal end 160 can have geometry to mechanically lock the anchor into the catheter shaft (i.e., barb(s), serrated edges, ribs, etc.). The inner diameter or lumen 164 of the anchor 158 is open to allow for catheter wiring, flex circuits, etc. to pass through the catheter shaft. Additionally, the wiring, flex circuits, etc. could be, if desired, run on the outer diameter of the anchor device 158. Additionally, when the splines 14 are inserted into the anchor 158 and it is press fitted into the catheter shaft 20C, the anchor 158 locks into the catheter shaft 20C to enable the shaft 20 to be rotated without the basket 12 slipping inside the catheter shaft 20C. Some non-limiting advantages of the anchor 158 of the present invention include, but are not limited to, ease of allowing fastening or gathering of basket splines 14 made of any material; may be fabricated from any suitable material or multiple materials; allows for variable positioning (length and angular) of the basket splines 14 to ensure even collapsing into the recovery sheath device; and provides sufficient clearance for device wiring. Further, as depicted in FIG. 31D, the anchor 158 may include a hemostat plug 170 into which a spline tube 172, which may contain a spline 14, passes to provide a sealed proximal spline tube lumen. The hemostat plug 170 may also be useful in securing the slotted anchor 158 to the catheter shaft 20.

Figure 32A:
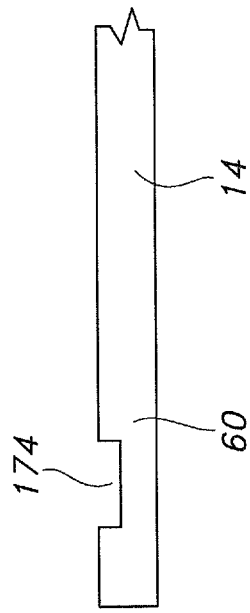
FIG. 32A is a depiction of a proximal portion of a spline having a spline notch, according to the present invention.
Figure 32C:
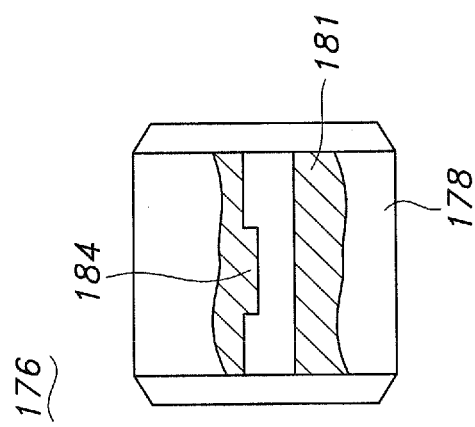
FIG. 32C is a partial exploded view of the anchor of FIG. 32B according to the preset invention.
Figure 32B:
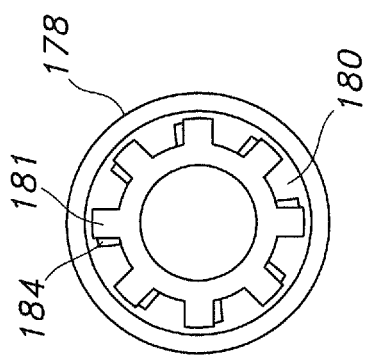
FIG. 32B is a schematic illustration of an anchor useful for securing the spline of FIG. 32A, according to the preset invention.

FIGS. 32A through 32C depict another embodiment of a proximal anchor 18 of the present invention, in which an anchor 176 is provided. The spline 14 may contain a notch 174 at the spline proximal end 60. The anchor 176 includes an inner ring 181 having spline alignment slots 180 through which the spline ends 60 may pass. The spline ends 60 are interlocked with the anchor 176 via the spline notch 174 and alignment detent 184. This interlock provides both excellent pull out retention and automatic, accurate alignment of all splines 14 with respect to each other so that they collapse neatly and reliably into the guide catheter 46 during introduction and removal of the catheter 20. Once the splines 14 interlock with the anchor 176, a second thin-walled tubing 178 is inserted over the anchor 176. This tube 178 prevents the splines 14 from disengaging their interlocks in the anchor 181. A complete lack of applicable forces on the internal anchor ring, adhesive and a slight interference fit between the external anchor and internal anchor rings prevents pull out of the inner anchor during use.

FIG. 33A is a perspective view of the basket 12 showing spline tubes 172 having spline tube assemblies 185 and exposed electrodes 186. FIG. 33B is a side elevational view of the basket 12 of FIG. 33A. The spline tubes 172 are disposed over the splines 14 except at distal basket portion 70 where the splines 14 emerge from the distal tip 16. The exposed electrodes 186 are spaced along spline distal portions 66, spline medial portions 64 and spline proximal portions 62. The number of exposed electrodes 186 may vary. The electrodes 186 are part of a flex electrode circuit 188, which will be described in further detail below.

FIGS. 34A and 34B are exploded partial cross-sectional views of the spline tubes 172 and spline tube assemblies 185. The splines are disposed within a lumen 208 of the spline tubes 172. As depicted in FIGS. 34A and 34B the splines 14 are not fixed to lumen 208 of the spline tube 172. The spline tube 172 may be slidingly assembled over the spline 14 to provide some interference there between. The spline tube 172 may desirably include a flexible material so that the lumen 208 of the spline tube 172 takes an elliptical shape substantially matching the cross-sectional extents of the spline 14.

FIG. 34C depicts a cross-section of the spline 14 of the present invention. As depicted in FIG. 10, spline 14 may have a flat or substantially flat upper surface 190, a flat or substantially flat lower surface 192, and rounded sidewalls 194, 196. The present invention, however is not so limited, and the upper surface 190 and/or the lower surface 192 may be rounded or otherwise have curvature, including concave and/or convex curvatures. The splines 14 desirably include and/or are made of a super-elastic material so that the splines bow outwardly into the basket shape 12, including asymmetric basket shapes. Any suitably super-elastic material may be used. Preferably, the splines include or are made of nitinol. If desired, the spline material may also be a shape memory material, such as but not limited to shape memory nitinol. Further, the splines 14 may be about 0.013 to about 0.025 inches wide and about 0.002 to about 0.010 inches thick. These dimensions are non-limiting and other dimensions may suitably be used.

FIGS. 34D through 34F depict radiopaque markers 198 useful with the spline tubes 172 and spline tube assemblies 185 of the present invention. As depicted in these figures, the radiopaque marker 198 may be disposed over a portion of the spline 14 that is near an electrode 186. Desirably, the radiopaque marker 198 is securably fixed to the spline 14. A significant useful feature of the current design over prior art is the radiotransparency of the flex circuit electrodes 186 (described below). This feature allows the separation of the fluoroscopic images of the splines and electrodes provided by the radiopaque markers 198 from the signal gathering function of the electrodes. This feature allows distinguishable patterns of electrode markings to be produced under fluoroscopy without modifying or compromising the electrogram gathering performance of the electrodes 186.

Figure 34G:
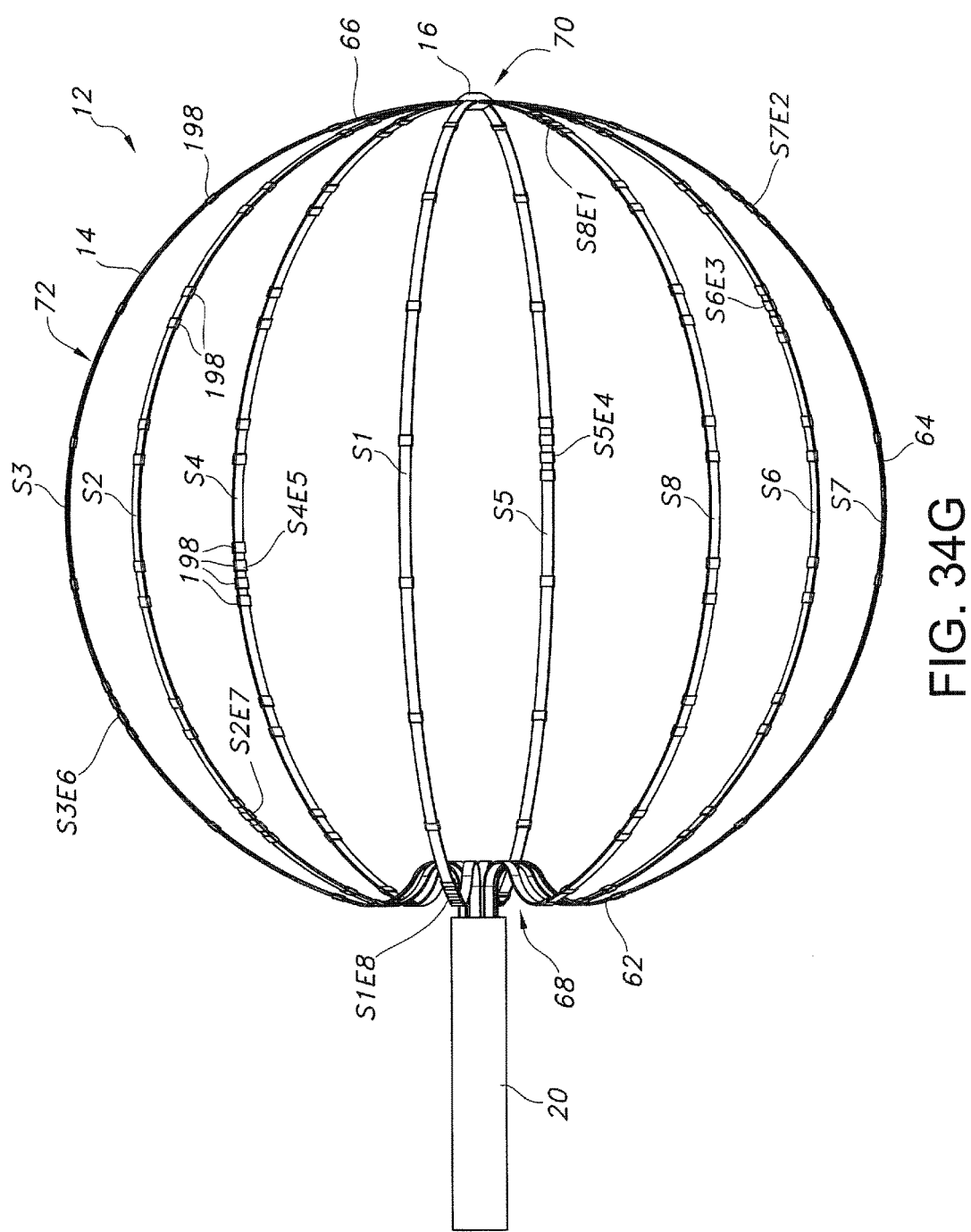
FIG. 34G is a representation of a fluoroscopic image of a side elevation view of a basket with radiopaque marker arrangement to depict spline and electrode locations, according to the present invention.
Figure 34H:
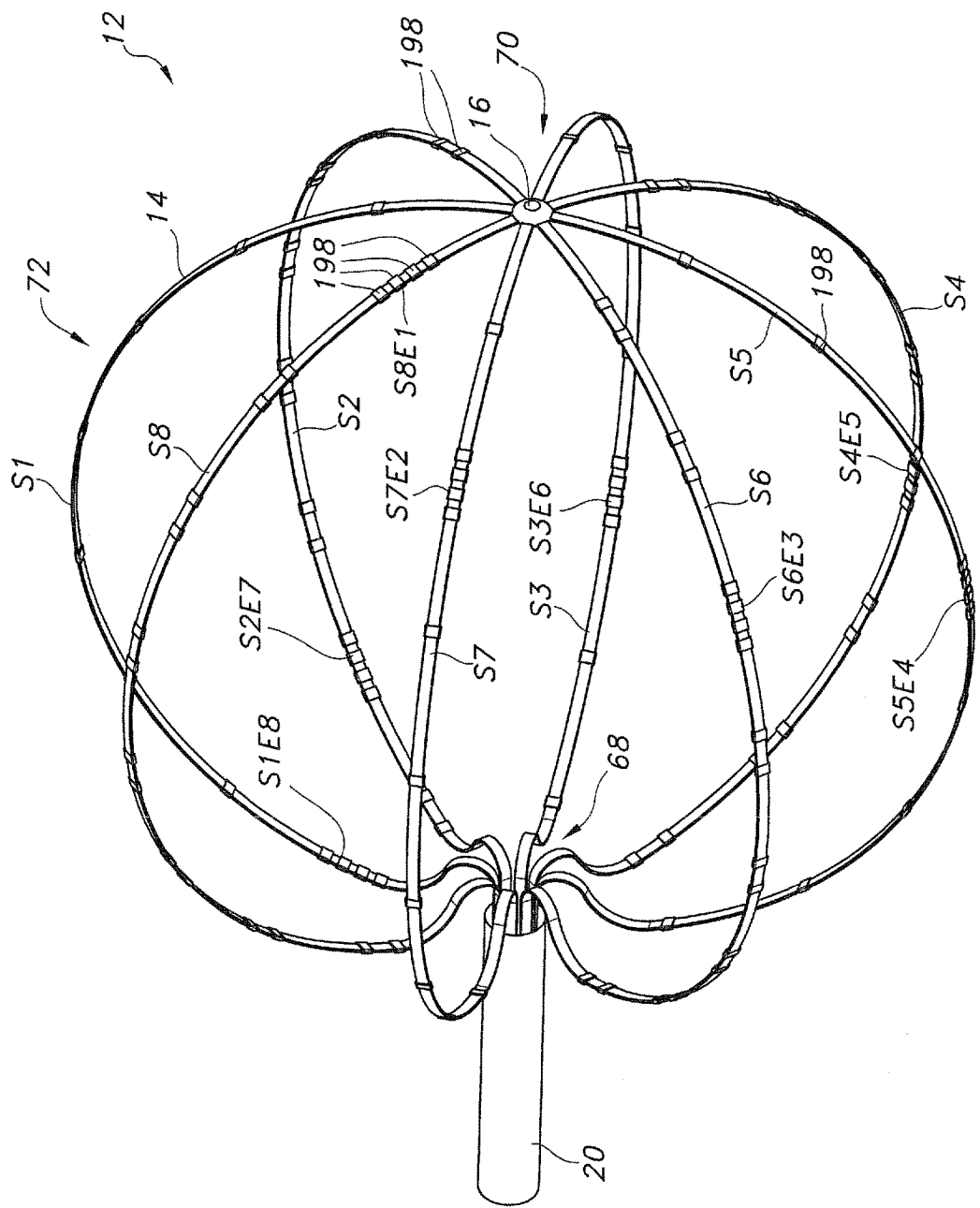
FIG. 34H is a representation of a fluoroscopic image of a perspective view of the basket of FIG. 34G, according to the present invention.
Figure 34I:
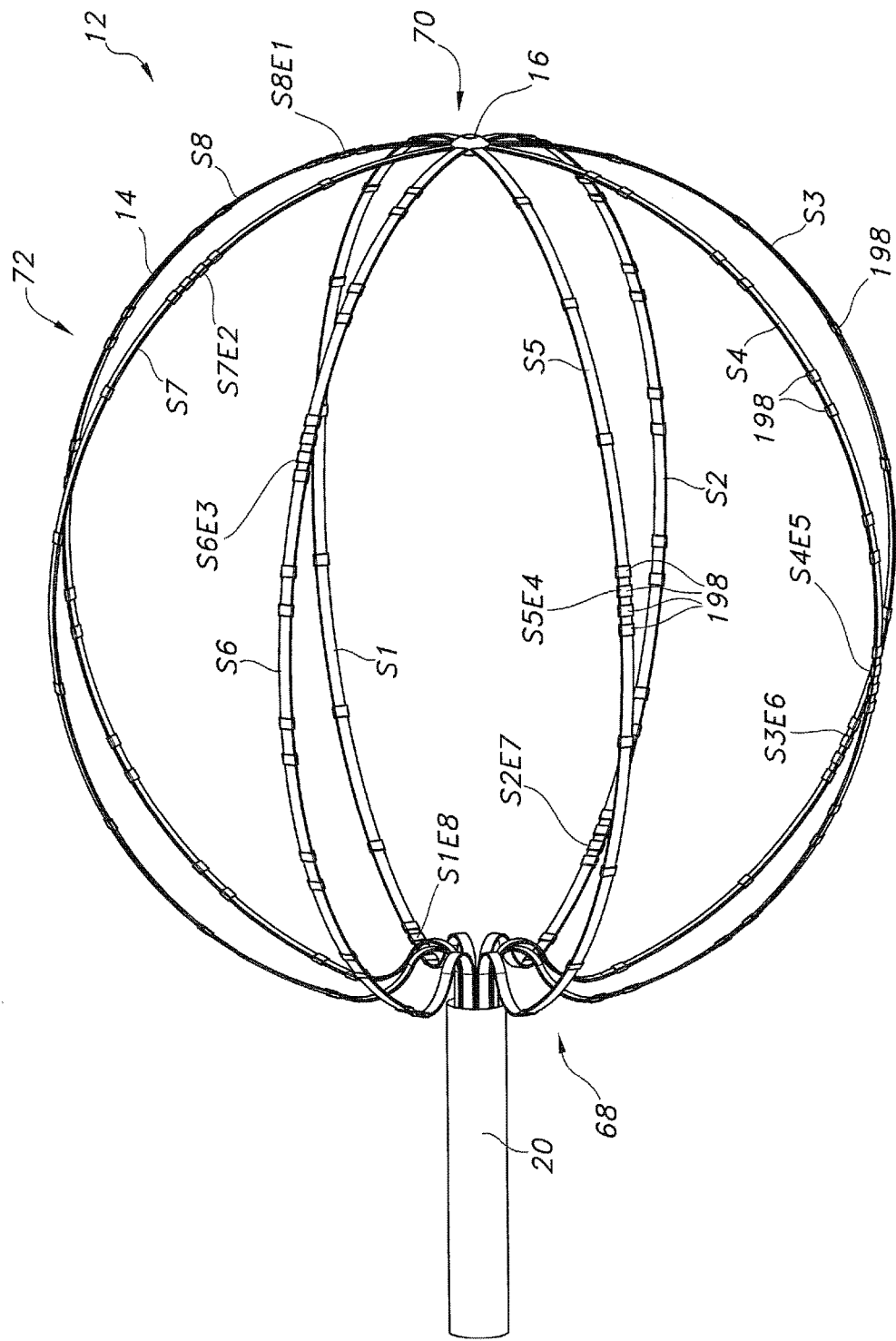
FIG. 34I is a representation of a fluoroscopic image of a rotated side view of the basket of FIG. 34G, according to the present invention.

FIGS. 34G through 34H depict a non-limiting arrangement of radiopaque markers 198 with the spline basket 12 of the present invention. The number of radiopaque markers 198 may vary along each spline 14 and may vary from spline to spline. These figures represent the two-dimensional shadowgraphs produced by fluoroscopy. FIG. 34G is a side perspective view of the basket 12 under fluoroscopy. Each spline 14 has four radiopaque markers 198 identifying a particular electrode on a particular spline 14. For example, the four radiopaque markers 198 at S1E8 refers to the unique combination set of {spline 1, electrode 8}; at S2E7 refers to {spline 2, electrode 7}; at S3E6 refers to {spline 3, electrode 6}; at S4E5 refers to {spline 4, electrode 5}; at S5E4 refers to {spline 5, electrode 4}; at S6E3 refers to {spline 6, electrode 3}; at S7E2 refers to {spline 7, electrode 2}; and at S8E1 refers to {spline 8, electrode 1}. In addition other electrodes 186 are marked with one marker 198 or two markers 198. Generally, even numbered splines have two markers 198 at each electrode position, and the odd numbered splines have one marker 198 at each electrode position not marked with the four markers. Such an arrangement, as depicted in FIG. 34H allows a practitioner to easily note the orientation of the basket 12 under fluoroscopy, including the location of the distal tip 16 and all of the electrodes 198. FIG. 34I depicts that when the basket 12 of FIG. 34 G is rotated, individual splines 14 and electrodes 186 become apparent with the placement of the radiopaque markers 198. For example, in FIG. 34I, the identity of each pair of crossed splines (S7 & S8, S1 & S6, S2 & S5, S3 & S4) would be ambiguous on one side of the crossing if each electrode were marked with a single RO marker. Further, a portion of the catheter body 20 (not shown) may also include radiopaque markers (not shown) to further aid the practitioner under fluoroscopy.

FIGS. 35A through 35H depict the spline tubes 172 with the spline tube assemblies 185 of the present invention. As depicted in FIG. 35A, the spline tube 172 is an elongate tubular member. The spline tube 172 or spline tube assembly 185 includes a proximal end 200 and a distal end 202. As depicted in FIG. 35A, a portion of the spline 14 may emerge from the tube distal end 202, where it may engage the distal tip 16. The present invention, however, is not limited to flexible tube assemblies 185 only with the use of the basket 12. The flexible spline tube assemblies 185 may be used by them themselves or with any other device where electrical activity within a body is to be monitored. In some cases spline tube assembly 185*a* may not need to have a spline portion 14 or similar component exiting from the distal end 202. The spline tube assembly 185 of FIG. 35A has two flex circuits 188, each with four electrodes 186, mounted sequentially on the spline tube 172, while the spline tube assembly of FIG. 35B has one flex circuit 188 with eight electrodes 186. These numbers of flex circuits and electrodes are non-limiting.

FIG. 35C is a partial exploded view of the spline tube assemblies 185, 185*a* of FIGS. 35A and 35B. As depicted in FIG. 35C, the spline tube assemblies 185, 185*a* may include a first flex circuit 188*a* having electrodes 186 and a second flex circuit 188*c* also having electrodes 186. The first flex circuit 188*a* may have a transition portion 188*b* where the first flex circuit 188*a* transitions to a position on the tube 173 below that of the second flex circuit 188*c*. In such a manner, multiple flex circuits may be places on the tubes 172, while still orienting the electrodes 186 in substantially one direction, typically in an outward direction from the spline basket 12.

As depicted in FIGS. 35D and 35E, the proximal end 200 of the spline tube 172 may be sealed with a plug 204 of material. The material may be an adhesive, polymer or any other useful material having sealing characteristics. The distal end 202 of the tube 172 may also be sealed with a plug 206 of material. Such sealing closes the internal lumen 208 of the spline tube 172 against the flow of fluids, including body fluids, such as blood. Such sealing also secures the spline tube 172 to the spline 14. The present invention, however, is not limited to having just the proximal end and/or distal end so sealed or secured and intermediate portions may also be so sealed or secured.

As depicted in FIGS. 35F and 35G, the flex circuit portions 188a, 188b and 188 exiting the spline tubes 172 may be embedded into the wall of the spline tube 172. The present invention is, however, not so limited and as depicted in FIG. 35H, a portion of the flex circuit 188 may transition from the outer surface 208A and past the inner surface 208B so that it is disposed within the lumen 208 of the tube 172. The spline tube 172 and the spline tube assembly 185 may comprise a biocompatible polymer such as a polyether block amide material, such as Pebax®. Other flexible biocompatible polymers, such as polyesters, silicones (e.g. Silastic®), silicone rubber, urethanes (e.g. Texin® and Pellethane®), and the like may suitably be used.

FIGS. 36A through 36E depict an embodiment of the flex circuit 188 as a flex circuit strip 212 of the present invention. The flex circuit 212 includes a proximal end 214 and a distal end 216. Towards the distal end 216 is an electrode-containing portion 218. The medial portion 220 may be free of electrodes. The flex circuit strip 212 may contain wings 222. These wings are useful in securing the flex circuit 212 to tubular members, such as spline tubes 172, especially where it is desirable to keep the electrodes 186 as substantially unidirectional flat electrodes. The flex circuit or electrode assembly strip 188 may have a thickness from about 0.001 inches to about 0.010 inches, more desirably from about 0.005 inches to about 0.008 inches.

Figure 36A:
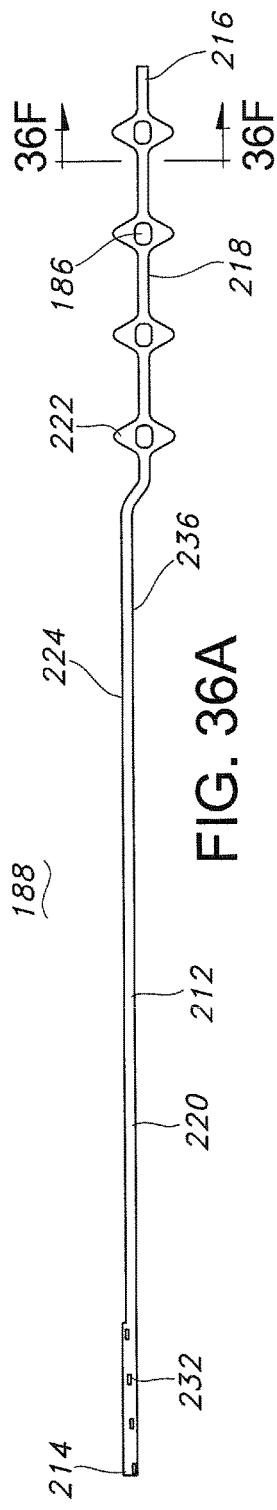
FIG. 36A is a top view of a flex circuit, according to the present invention.
Figure 36B:
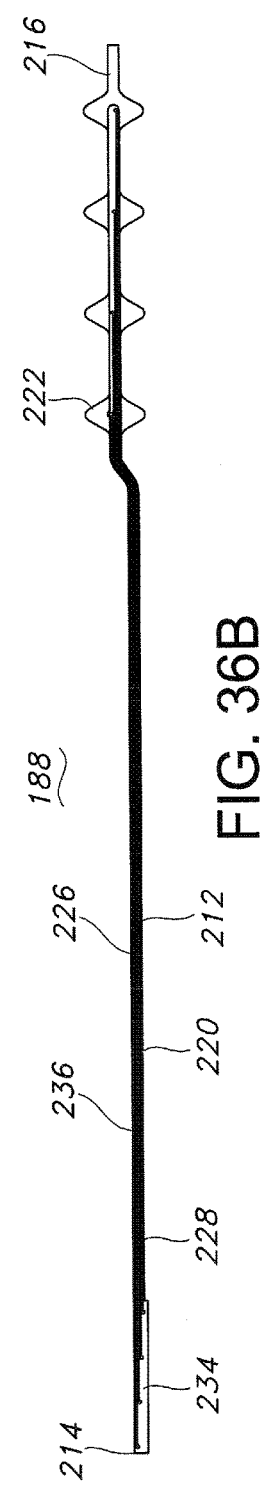
FIG. 36B is a bottom view of the flex circuit of FIG. 36A, according to the present invention.
Figure 36C:
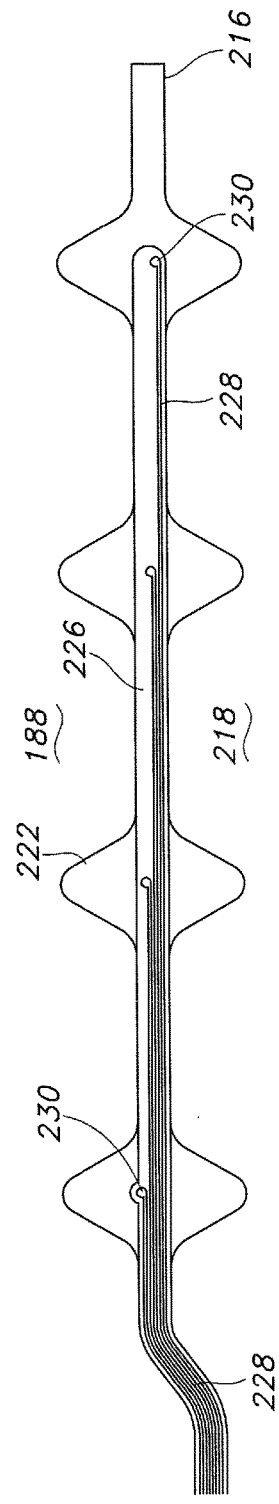
FIG. 36C is an exploded, right bottom view of a portion of the flex circuit of FIG. 36A, according to the present invention.
Figure 36D:
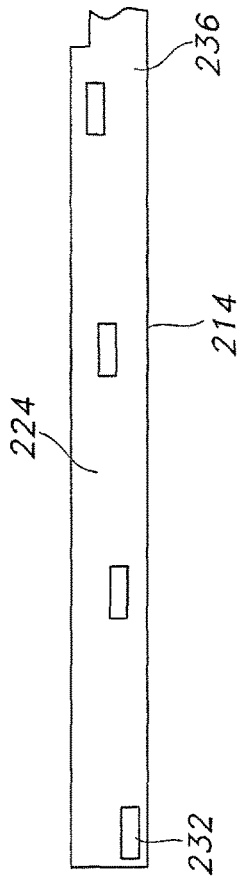
FIG. 36D is an exploded, left top view of a portion of the flex circuit of FIG. 36A, according to the present invention.
Figure 36E:
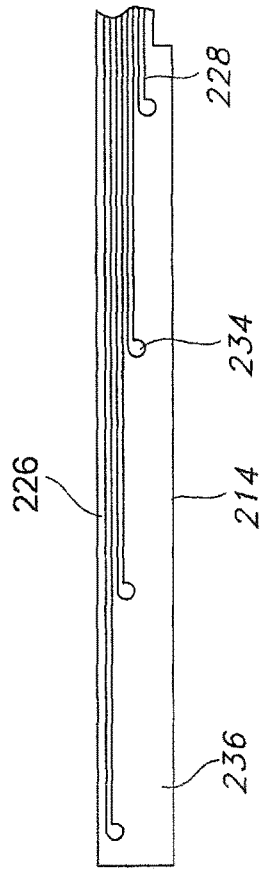
FIG. 36E is an exploded, left bottom view of a portion of the flex circuit of FIG. 36A, according to the present invention.

FIG. 36A is a top view of the flex circuit strip 212 showing electrodes 186 disposed on the upper surface 224 of the flex circuit substrate 236. The flex circuit substrate or polymeric substrate 236 may comprise a polyimide material, such as KAPTON polyimide available from DuPont, which is suitable for short term (single use medical device) or long term (medical implant) contact with skin, tissue or blood, depending on the intended application, but other suitable materials may be used, such as the above-described materials for the spline tube 172 or the spline tube assembly 185. At the proximal end 214 electrical pads are disposed on the upper surface 224. FIG. 36B is a bottom view of the flex circuit strip 212. Electrical traces 228 are disposed on the bottom surface 226 of the substrate 236. The traces run from location underneath the electrodes 186 to locations underneath the electrical pads 232. As depicted in FIGS. 36C through 36E, metal plated holes or vias 230 electrically connect individual traces to individual electrodes 186. In a similar fashion vias 234 connect individual electrical traces 228 to individual electrical pads 232.

Figure 36F:
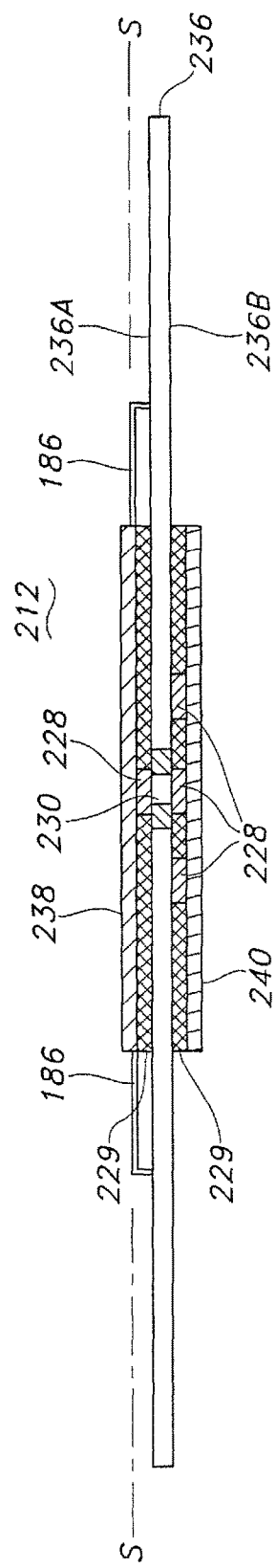
FIG. 36F is schematic, cross-sectional view of a portion of the flex circuit of FIG. 36A, according to the present invention.

As depicted in FIG. 36F, the flex circuit 212 may contain upper surface coverlays 238 to cover those areas of the upper substrate surface 236A not having electrodes 186 or connection pads 232. Likewise, if desired, bottom surface coverlays 240 may cover part or all of the electrical traces 228. Upper coverlays 238 and lower coverlays 240 are bonded to the substrate 236 with the use of suitable adhesive 239, usually acrylic adhesive. Desirably, the upper flex circuit axis S is substantially smooth, i.e., the coverlays 238 and the electrodes 186 being substantially the same height. The present invention, however, is not so limited, and electrodes may be raised slightly above the substrate surface with the use, for example, of strips of material disposed between the substrate 236 and the electrodes 186. Alternatively, the electrodes may be depressed slightly below the substrate surface, as shown in FIG. 36F. The coverlays 238, 240 may comprise a similar material as the substrate 236, but different materials may suitably be used.

Figure 37A:
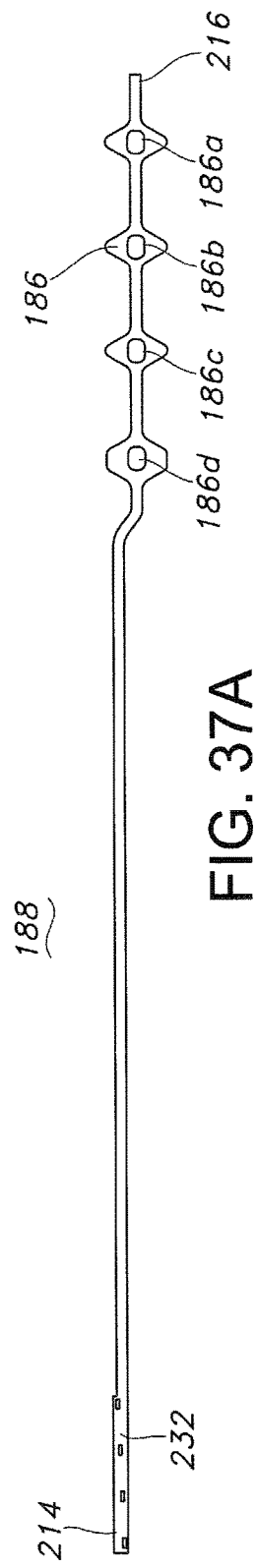
FIG. 37A is a top view of another embodiment of a flex circuit, according to the present invention.
Figure 37B:
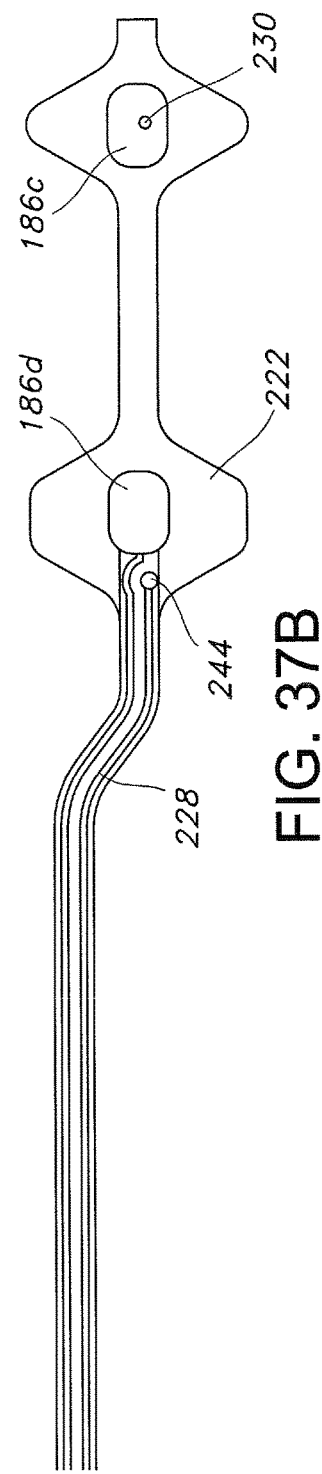
FIG. 37B is an exploded, right top view of a portion of the flex circuit of FIG. 37A, according to the present invention.
Figure 37C:
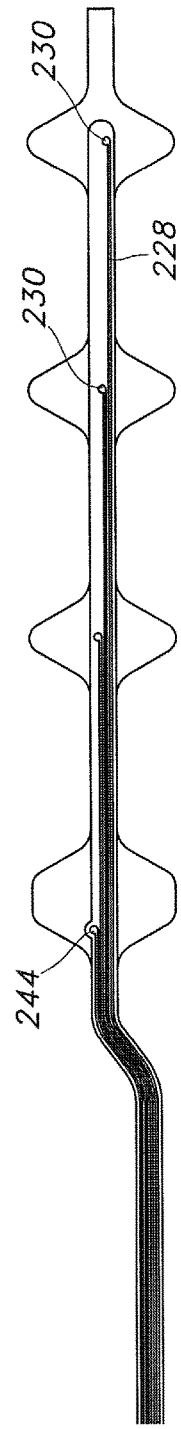
FIG. 37C is an exploded, right bottom view of a portion of the flex circuit of FIG. 37A, according to the present invention.

FIGS. 37A through 37C depict an alternate embodiment of the flex circuit 188. As depicted, electrical traces may run on both sides of the flex circuit substrate 236. For example, four electrodes, 186a, 186b, 186c and 186d are depictured in FIG. 37A. In the top view of FIGS. 37A and 37B no electrical traces run on the upper surface 224 between the electrodes 186. However, proximal to the electrodes, electrical traces 228 for two electrodes 186c, 186d run on the upper surface 224, and the electrical traces for the other electrodes 186a, 186b run on the bottom surface 226 of the flex circuit substrate. The electrical trace 228 for electrode 186c transitions from the bottom surface 226 to the upper surface 224 by means of a trace-to-trace via 244. Such as arrangement of electrical traces 228 as depicted in FIGS. 37A through 37C may make for a more overall compact flex circuit.

FIGS. 38A and 38B depict a flexible electrode assembly strip 247. The flexible electrode assembly strip includes a flex circuit or electrode assembly strip 188, 236 pressed into the substrate 246 of a flexible polymeric material, such as any of the above-described materials for the spline tube 172 or the spline tube assembly 185. The flex circuit or electrode assembly strip 188, 236 may also be thermally, compressively and/or adhesively bonded onto or into the substrate 246. While the substrate 246 is depicted as being a strip or being planar, the present invention is not so limited. The substrate could be tubular with or without an open lumen. As depicted in FIG. 38B the electrode assembly strip 188, 236 is pressed into the substrate wall 246b while leaving a substantially smooth upper surface 246A and lower surface 246C. If desired portions of the flex circuit 188, 236, for example those portions not containing electrodes, may be disposed between multiple two or more substrates 246, either in planar or tubular form. When covering the electrodes with a cover or substrate of polymeric material, it is desirable to remove cover or substrate material so that the electrodes 186 remain exposed.

All components, i.e., splines, electrode flex circuits, electrode elevation strips (used to raise the surface of the electrodes above the substrate, if desired; not shown), radiopaque marker strips are desirably thin, flat, planar elements. In a simple design, these elements may be stacked and adhesively bonded to each other. Alternately, a length of flexible tubing or membrane can be slid over the bonded spline/radiopaque marker/flex circuit/electrode elevation strip in order to contain all parts within a single body. This tube or membrane can be shrunk in place for a tight, contained fit using either heat shrink tubing or tubing that is chemically expanded (e.g., by absorption of alcohol or other chemical) for assembly, and then contracts when the chemical evaporates.

Figure 39:
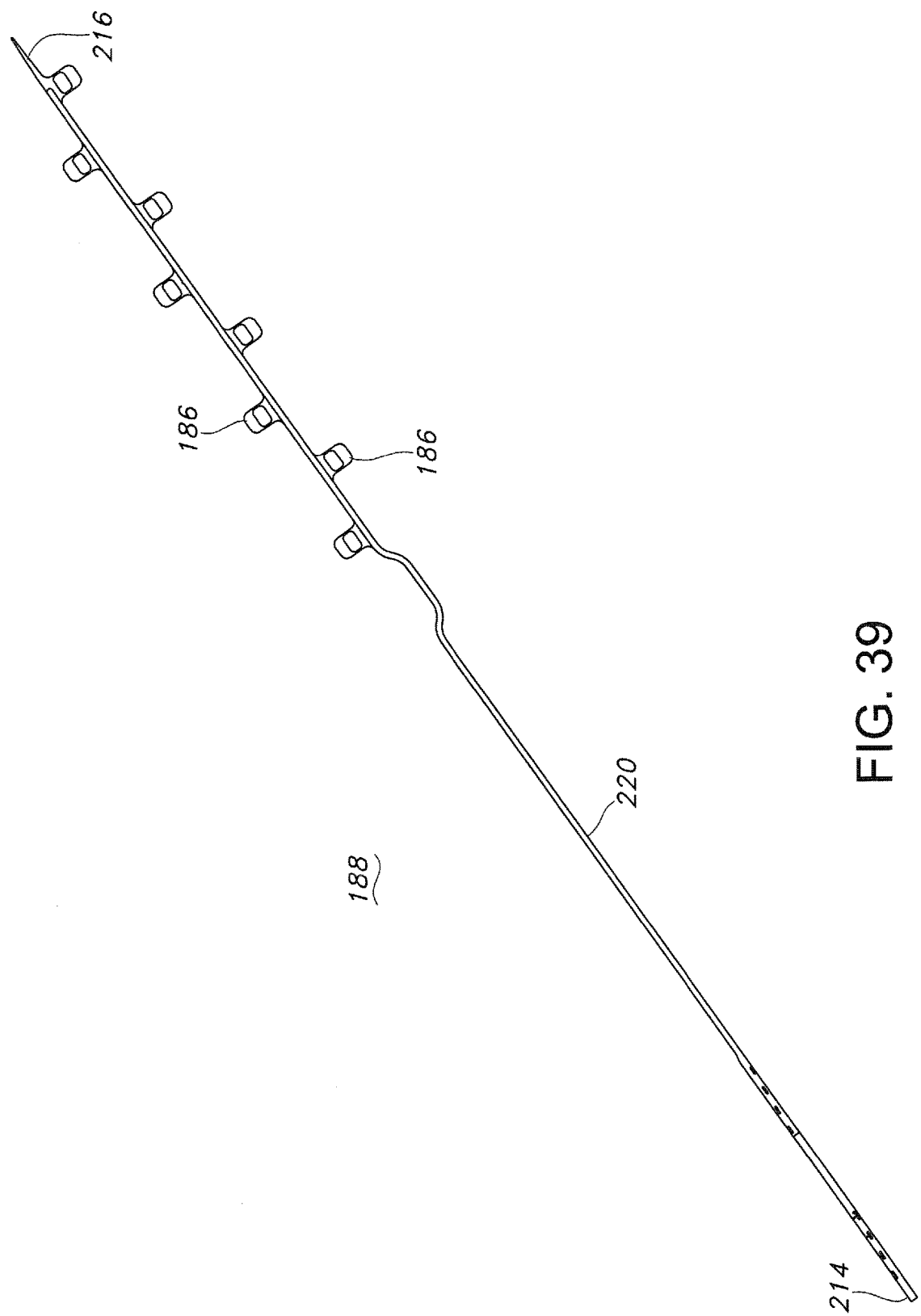
FIG. 39 is a top view of another embodiment of a flex circuit, according to the present invention.

FIG. 39 depicts yet another alternate embodiment of a flex circuit 188 having laterally staggered electrodes 186.

FIGS. 40A and 40B depict the use of quad wires 248 which connect proximal end 214 of the flex circuit 188. Individual quad wires 248 are connected to individual electrical pads 232 at the proximal ends 214 of the flex circuits. The quad wires 248 then are routed through the catheter body 20 and handle 28 to the catheter connector located at the proximal end of the handle 28.

Figure 41A:
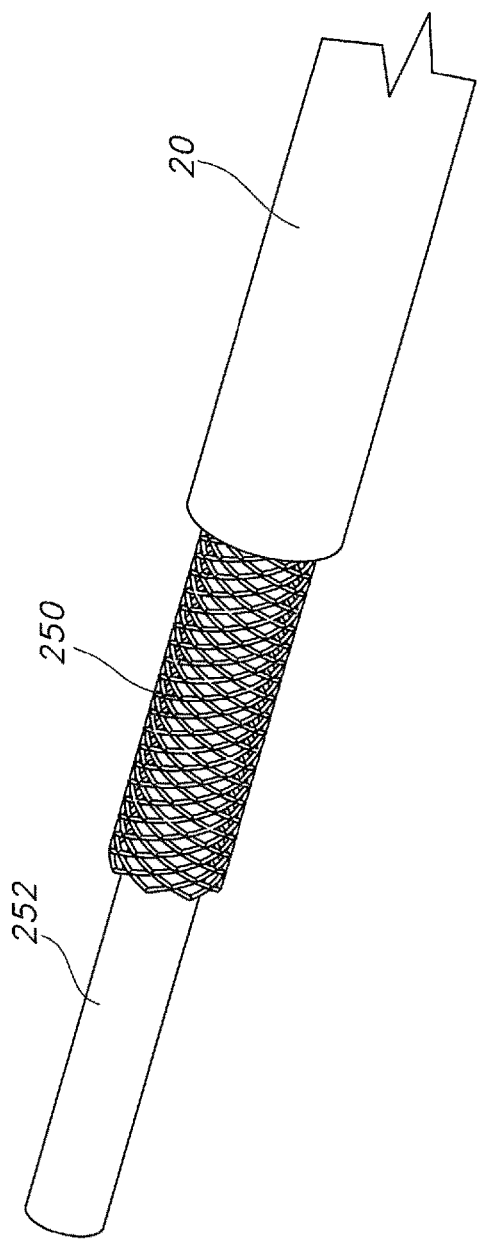
FIG. 41A is a partial cut-away perspective view of a catheter shaft with a braided shield and anti-kink beading, according to the present invention.
Figure 41B:
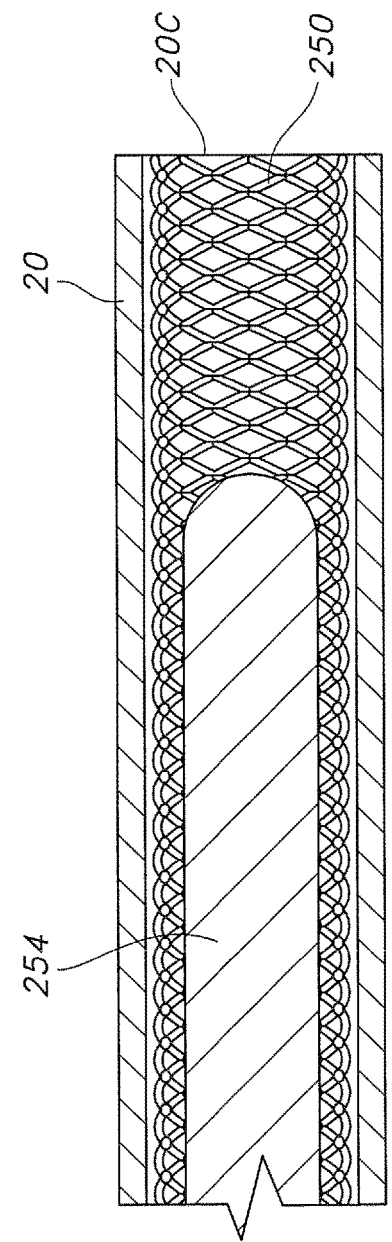
FIG. 41B is a partial cut-away perspective view of another embodiment of a catheter shaft with a braided shield and anti-kink beading, according to the present invention.

FIGS. 41A and 41B depict a portion of the catheter shaft 20 as having a braided shield 250 that minimizes possible electro-magnetic interference from outside sources. The catheter 20 may also have anti-kink beading sections 252 or 254, which provide greater support to prevent kinking of the catheter 20. Flexibility of the catheter body 20 may also be controlled which advantageously aids in having the basket 12 more closely match the contours of the heart.

FIGS. 42A through 42C further depict asymmetric basket shapes for basket 12. FIG. 42A is a side view of the asymmetric basket shape is depicted. The basket shape is asymmetric in this view in that, among other things, the basket shape is not spherical and/or the proximal spline portions 62 may contain different degrees of curvature or bends 82, 84. These bends 82, 84, also known as a dimple end and/or a puckered end, allows the basket 12 to compress when the heart contracts. In other words, the proximal portion 68 of the basket 12 is designed with greater flexibility to ensure, among other things, improved contact of the splines 14 with interior surfaces of the heart wall.

While one overall basket shape is depicted in FIG. 42A, it may be desirable to have different basket shapes, for example, a right atrial basket shape and a left atrial basket shape. These different baskets may have different basket outline shapes and therefore different compliances of the individual splines. These differences may allow each shape to optimally conform to the differently shaped left atrium and right atrium. In addition, each shape may come in several different overall sizes. Note that the specific shape shown in FIG. 42 is not intended to represent an "atrial shaped basket", but is instead an arbitrary shape that illustrates the design features required to fabricate an asymmetric basket that will successfully collapse within a guide catheter.

FIGS. 42B and 42C are an end views of the basket 12 of FIG. 42A. As depicted in FIG. 42B, all spline portions are substantially equidistant from the center longitudinal axis L and/or tip 16 or are substantially in the center of the overall basket outline C as depicted. As depicted in FIG. 42C, all spline portions are not substantially equidistant from the center longitudinal axis L and/or tip 16 or are not substantially in the center of the overall basket outline C as depicted. Such asymmetry provides for improved basket performance by more closely matching the shape of the atria of the heart. The splines 14 in FIG. 42A have an equal or substantially equal longitudinal length. The varying distances of the medial portions 64 of the splines from the center longitudinal axis L results from, in part, the flexibility of the splines 14 at the proximal spline portions 62 due to the inclusion of the bends 82, 84. While the longitudinal lengths of the splines 14 are equal or substantially equal in FIG. 42A if the basket 12 is in its compressed state, the present invention is not so limited, and splines 14 of varying lengths may be suitably used. Such varying lengths may be achieved by imparting geometries to different bends 82, 84. For example, some bends may have greater inward longitudinal extents than other bends such that, when compressed with the guide catheter 46, all the splines 14 of the basket 12 have an equal or substantially equal net line segment between the anchor 18 and the tip 16. When the basket 12 is expanded, the bends 82, 84 may "relax" and provide a basket assembly 12 with splines 14 of net different lengths, for example spline 14a having an effective longer length than spline 14b. Such asymmetry provided by, in part, splines 14 of varying lengths provide for a closer matching of the shape of the basket 12 with interior portions of the heart, i.e., the atria, as the heart is beating.

In a similar fashion, the bends 78, 80 at the distal basket portion 70 also provide for asymmetry, if desired. As depicted, both proximal and distal spline portions 62, 66 may have different recurves or incurvate bends to more effectively match the shape of a typical atrium. Different proximal recurves with different lengths and/or angles compensate for different spline lengths so that the basket may be disposed within the guide catheter where the splines would have the same or about the same effective length when the basket is compressed, but will have different effective lengths when the basket is expanded.

The apparatus, system or devices of the present invention may include electrodes are configured as Monophasic Action Potential (MAP) electrodes, where a single electrode at each site is configured to intimately contact the tissue, and a second electrode at each site is configured to face away from the tissue, acting as an MAP "reference" electrode. An electronic Data Acquisition System may be configured to record the electrograms produced by the catheter as MAP electrograms. The electronics Data Acquisition System may also be selected to record the electrograms produced by the catheter as either standard unipolar electrograms, bipolar electrograms or as MAP electrograms. Further, the electrodes may be configured as Modified Monophasic Action Potential (m-MAP) electrodes, where a single electrode at each site is configured to intimately contact the tissue, and a second electrode placed intermediate between two or more sensing (i.e., tissue facing) electrodes, which is configured to face away from the tissue, acting as an MAP "reference" electrode for multiple sensing electrodes. The curvature of the splines is specifically chosen to match the curvature of a "typical" atrium for the purpose of enhancing electrode to tissue contact, producing the contact force required for quality MAP mapping. The splines may be curved at the proximal end with different length segments in order to compensate for the different spline lengths that result from matching the splines to the shape of a typical atrium; where equal spline total length (tissue contact segment plus recurve segment) is required to allow collapsibility for introduction and withdrawal of the catheter through the second elongate tube.

Figure 43A:
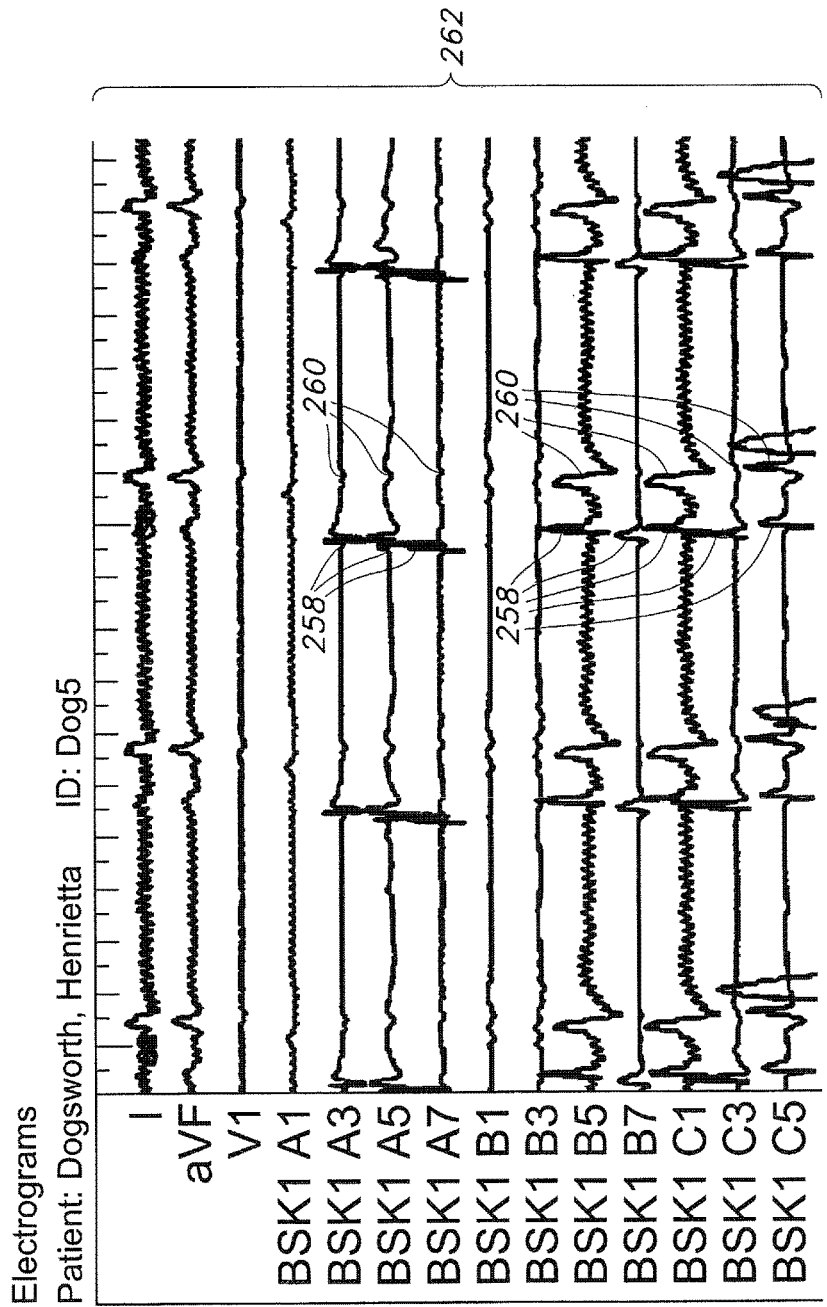
FIG. 43A is an electrogram obtained with the catheter basket system of the present invention.
Figure 43B:
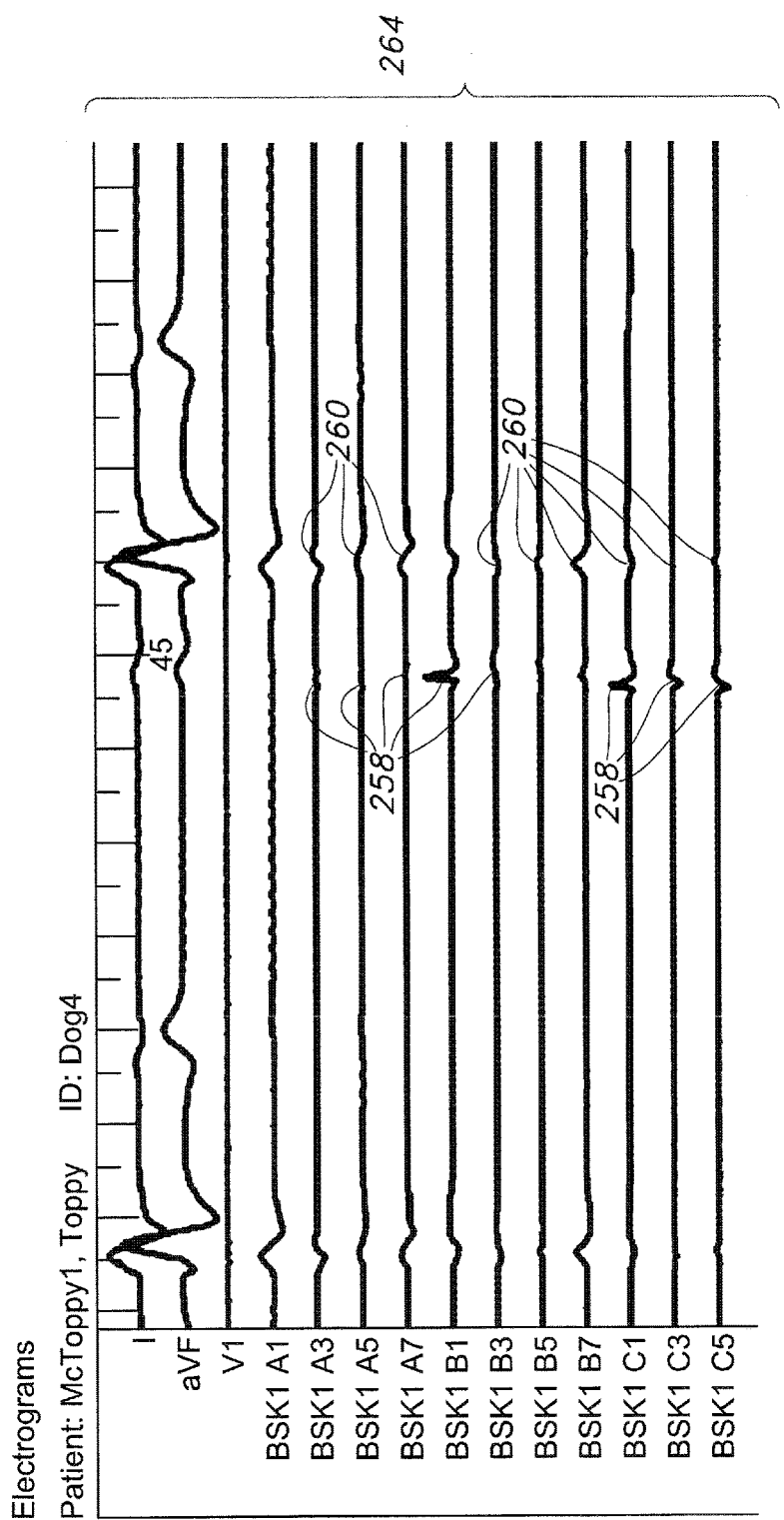
FIG. 43B is an electrogram obtained with a catheter basket system of the prior art.

FIGS. 43A and 43B are bipolar electrograms 262, 264 obtained from animal studies. In FIG. 43A the electrograms 262 were obtained from the use of the system 10 of the present invention. In FIG. 43A, the atrial signals 258 are much larger than the ventricular signals 260 on electrodes A3, A5, A7, B7 and C3. Further in FIG. 43A, the atrial signals 258 are approximately equal to the ventricular signals 260 on electrodes B5, C1 and C5. Moreover, in FIG. 43A, the electrogram traces I, aVF and V1 are not basket signals. In general the atrial signals 258 are much larger than or equal to the ventricular signals 260. This allows a practitioner to more easily map the atrial signals within the heart to locate heart tissue causing heart fibrillations. The practitioner may suitably ablate such areas.

FIG. 43B depicts electrograms 264 obtained from animal studies using a commercially available prior art basket catheter. In FIG. 43B, atrial signals 258 are absent on electrodes A1, A5 and A7. Also in FIG. 43B, the atrial signals 258 are smaller than the ventricular signals 260 on electrodes A3, B5 and B7. Further in FIG. 43B, the atrial signals 258 are approximately equal to the ventricular signals 260 on electrode B3. Still further in FIG. 43B, the atrial signal 258 are larger than ventricular signals 260 on electrodes B1, C1, C3 and C5. Moreover, in FIG. 43B, the electrogram traces I, aVF and V1 are not basket signals. In general, the atrial signals 258, when present, are much smaller than ventricular signals 260 on some electrodes, but may also be larger on other electrodes. The recorded signals of FIG. 43A represent a significant improvement over the recorded signals of FIG. 34B. While not being bound by any theory, it is believed that the substantially flat, single sided flex electrodes 186 of the present invention with the described flex circuits and spline tube assemblies, superior contact and contact force generate higher atrial signals from the heart while reducing the ventricular signals from the heart.

Further, the improved basket geometries of the present invention also contribute to improve mapping of the atrial signals as the baskets of the present invention are not only more stable within the atrium of the beating heart, but also can flex and contour to the varying complexities of the beating heart.

The devices of the present invention may suitably be used to detect or map cardiac rhythm disorders. Details of methods for detecting or mapping cardiac rhythm disorders may be found in U.S. Provisional Application No. 61/342,016, filed on Apr. 8, 2010, entitled "Methods, System And Apparatus For The Detection, Diagnosis And Treatment Of Biological Rhythm Disorders", which published as U.S. Patent Application Publication No. 2011/0251505 A1 for its corresponding Non-Provisional application Ser. No. 13/081,411, the contents of all which are incorporated herein by reference.

The following aspects, embodiments, and the like are part of the detailed description for the present invention. Embodiments directed to distal tip embodiments include, but are not limited to, as follows:

In one embodiment, a system (10) for sensing multiple local electric voltages from endocardial surface of a heart is provided. The system may comprise a first elongate tubular member (20) having a lumen (20C), a proximal end (20A) and a distal end (20B); and a basket assembly (12) comprising: a plurality of flexible splines (14) for guiding a plurality of exposed electrodes (186), the splines (14) having proximal portions (62) and distal portions (66); an anchor (18) for securably affixing the proximal portions (62) of the splines (14); said anchor (18) being secured at the distal end (20B) of the first elongate tubular member (20); an encapsulated and filament-wrapped distal tip (16, 120) comprising an encapsulant (122) and a filament (124) for securably affixing the distal portions (66) of the splines (14) in a predetermined angular relationship at said distal tip (16, 120); wherein the splines (14) comprise a superelastic material; and wherein the basket assembly (12) has a radially expanded non-cylindrical shape. The system (10) of may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has a substantially cylindrical shape when compressed within the lumen (48) of the second elongate tubular member (46); and wherein the basket assembly (12) has said radially expanded non-cylindrical shape when not compressed within the lumen (48) of the second elongate tubular member (46) and disposed past the distal end (54) of the second elongate tubular member (46). The encapsulant may have a smooth, non-thrombogenic outer surface free of voids and slots which would permit the passage or entry of blood thereinto. The encapsulant (122) may comprise a thermoplastic material. The encapsulant (122) may also comprise a polyurethane material. The filament (124) may comprise a polymeric filament, a metallic filament or combinations thereof. The filament (124) may be laced, looped or wound between, over and under the splines (14) to substantially align and secure the distal portions (66) of the splines (14) in said predetermined angular relationship. The flexible splines (14) may further comprise alignment members (89) at the distal portions (66) of the splines (14); and wherein the filament (124) is also laced, looped or wound between, over and under the alignment members (89). The alignment members (89) may comprise circular portions at the distal spline portions (66). The angles ($\theta 1$-$\theta 8$) between said splines (14) at said distal tip (16, 120) forming said predetermined angular relationship may be all substantially equal to each other. Alternatively, at least one angle ($\theta 1$-$\theta 8$) between said splines (14) at said distal tip (16, 120) forming said predetermined angular relationship may be different from another angle ($\theta 1$-$\theta 8$) between said splines (14) at said distal tip (16, 120). When basket assembly (12) is in said radially expanded non-cylindrical shape, the splines (14) may extend beyond the distal tip (16, 120) and may comprise excurvate bends (80) beyond the distal tip (16) to bend the splines (14) back towards the anchor (18).

In one embodiment, a system (10) for sensing multiple local electric voltages from endocardial surface of a heart, may comprise: a first elongate tubular member (20) having a lumen (20C), a proximal end (20A) and a distal end (20B); and a basket assembly (12) comprising: a plurality of flexible splines (14) for guiding a plurality of exposed electrodes (186), the splines (14) having proximal portions (62) and distal portions (66); an anchor (18) for securably affixing the proximal portions (62) of the splines (14); said anchor (18) being secured at the distal end (20B) of the first elongate tubular member (20); a distal tip (16, 150) comprising an elastomeric material for securably affixing the distal portions of the splines (14) in a predetermined relationship at said distal tip (16, 150); wherein the splines (14) comprise a superelastic material; and wherein the basket assembly (12) has a radially expanded non-cylindrical shape. The system may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has a substantially cylindrical shape when compressed within the lumen (48) of the second elongate tubular member (46); and wherein the basket assembly (12) has said radially expanded non-cylindrical shape when not compressed within the lumen (48) of the second elongate tubular member (46) and disposed past the distal end (54) of the second elongate tubular member (46). The distal tip (16, 150) may have a smooth, non-thrombogenic outer surface free of voids and slots which would permit the passage or entry of blood there into. Angles ($\theta 1$-$\theta 8$) between said splines (14) at said distal tip (16, 150) forming said predetermined angular relationship may be all substantially equal to each other. Alternatively, at least one angle ($\theta 1$-$\theta 8$) between said splines (14) at said distal tip (16, 150) forming said predetermined angular relationship is different from another angle ($\theta 1$-$\theta 8$) between said splines (14) at said distal tip (16, 150). The elastomeric material may comprise polyurethane, silicone and combinations thereof.

In one embodiment, a system (10) for sensing multiple local electric voltages from endocardial surface of a heart, may comprise: a first elongate tubular member (20) having a lumen (20C), a proximal end (20A) and a distal end (20B);

a basket assembly (12) comprising: a plurality of flexible splines (14) for guiding a plurality of exposed electrodes (186), the splines (14) having proximal portions (62) and distal portions (66); an anchor (18) for securably affixing the proximal portions (62) of the splines (14); said anchor (18) being secured at the distal end (20B) of the first elongate tubular member (20); a distal tip (16, 150) comprising a flexible material for securably affixing the distal portions of the splines (14); wherein the basket assembly (12) has a radially expanded non-cylindrical shape; wherein the splines (14) comprise a superelastic material; wherein said flexible material comprises a material selected from the group consisting of an elastomeric material, a non-elastic polymeric material, a thermoplastic material and combinations thereof; and wherein the splines (14) approach the tip (16) at an angle (α) of less than about 45° as measured from a line segment between the anchor (18) and the tip (16) along a longitudinal axis (L) between the proximal anchor (18) and the distal tip (16, 150). The system (10) of embodiment 19, may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has a substantially cylindrical shape when compressed within the lumen (48) of the second elongate tubular member (46); and wherein the basket assembly (12) has said radially expanded non-cylindrical shape when not compressed within the lumen (48) of the second elongate tubular member (46) and disposed past the distal end (54) of the second elongate tubular member (46). When basket assembly (12) is in said radially expanded non-cylindrical shape, the splines (14) may extend beyond the distal tip (16, 150) and may comprise excurvate bends (80) beyond the distal tip (16) to bend the splines (14) back towards the anchor (18). The angles (θ1-θ8) between said splines (14) at said distal tip (16, 150) forming said predetermined angular relationship may be all substantially equal to each other. Alternatively, at least one angle (θ1-θ8) between said splines (14) at said distal tip (16) forming said predetermined angular relationship may be different from another angle (θ1-θ8) between said splines (14) at said distal tip (16, 150).

In one embodiment, a system (10) for sensing multiple local electric voltages from endocardial surface of a heart, may comprise: a first elongate tubular member (20) having a lumen (20C), a proximal end (20A) and a distal end (20B); a basket assembly comprising: a plurality of flexible splines (14) for guiding a plurality of exposed electrodes (186), the splines (14) having proximal portions (62) and distal portions (66); an anchor (18) for securably affixing the proximal portions (62) of the splines (14); said anchor (18) being secured at the distal end (20B) of the first elongate tubular member (20); a distal tip (16, 104, 104', 126, 134, 140, 152) for comprising a first part and a second part that are securably affixed to one and the other; wherein the distal portions (66) of the splines (14) are securably and non-slidingly disposed within said distal tip (16) in a predetermined angular relationship; wherein the splines (14) approach the distal tip (16) at an angle (α) of about 90° or less than about 90° as measured from a line segment between the anchor (18) and the tip (16) along the longitudinal axis (L); wherein the basket assembly (12) has a radially expanded non-cylindrical shape; and wherein the splines (14) comprise a superelastic material. The system (10) may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has a substantially cylindrical shape when compressed within the lumen (48) of the second elongate tubular member (46); and wherein the basket assembly (12) has said radially expanded non-cylindrical shape when not compressed within the lumen (48) of the second elongate tubular member (46) and disposed past the distal end (54) of the second elongate tubular member (46). Angles (θ1-θ8) between said splines (14) at said distal tip (16, 104, 104', 126, 134, 140, 152) forming said predetermined angular relationship may be all substantially equal to each other. Alternatively, at least one angle (θ1-θ8) between said splines (14) at said distal tip (16) forming said predetermined angular relationship may be different from another angle (θ1-θ8) between said splines (14) at said distal tip (16, 104, 104', 126, 134, 140, 152). When basket assembly (12) is in said radially expanded non-cylindrical shape, the splines (14) may extend beyond the distal tip (16, 104, 104', 126, 134, 140, 152) and may comprise excurvate bends (80) beyond the distal tip (16, 104, 104', 126, 134, 140, 152) to bend the splines (14) back towards the anchor (18). The splines (14) may have distal end portions (67); and further wherein the distal spline end portions (67) may be securably and non-slidingly disposed within said distal tip (16, 104, 104', 126, 134, 140). The splines (14) may approach said distal tip (16) at an angle (α) of less than 45° as measured from a line segment between said anchor (18) and said distal tip (16, 104, 104', 126, 134, 140) along the longitudinal axis (L).

Embodiments directed to spline bends and recurves embodiments include, but are not limited to, as follows:

A system (10) for sensing multiple local electric voltages from endocardial surface of a heart, may comprise: a first elongate tubular member (20) having a lumen (20C), a proximal end (20A) and a distal end (20B); a basket assembly (12) comprising: a plurality of flexible splines (14) for guiding a plurality of exposed electrodes (186), the splines (14) having proximal portions (62), distal portions (66) and medial portions (64) therein between; a proximal anchor (18) for securably affixing the proximal portions (62) of the splines (14); said proximal anchor (18) being secured at the distal end (20B) of the first elongate tubular member (20); a distal tip (16) for securably affixing the distal portions (66) of the splines (14), said proximal anchor (18) and said distal tip (16) defining a longitudinal axis (L) therein between about which the splines (14) are disposed; wherein the splines (14) approach the distal tip (18) at an angle (α) of about 90° or less than about 90° as measured from a line segment between the proximal anchor (18) and the distal tip (16) along the longitudinal axis (L); wherein the splines (14) comprise a superelastic material such that the basket assembly (12) exhibits a substantially cylindrical shape when radially compressed and exhibits a radially expanded non-spherical shape when not radially compressed; and wherein at least some of the splines (14) in the radially expanded non-spherical shape contain a distal excurvate outward bend (80) disposed at the distal portion (66) of the spline (14) at a location near to the distal tip (16) of the basket assembly (12) to bend the splines (14) back towards the proximal anchor (18). The system may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has said substantially cylindrical shape when compressed within the lumen (48) of the second elongate tubular member (46); and wherein the basket assembly (12) has said radially expanded non-spherical shape when not compressed within the lumen (48) of the second elongate tubular member (46) and disposed past the distal end (54) of the second elongate tubular member (46). When basket assembly (12) is in said radially expanded non-spherical shape, the splines (14) may extend beyond the distal tip (16); and, when basket assembly (14) is in said radially expanded non-spherical shape, apices (81) of the distal excurvate bends (80) may be disposed beyond the distal tip (16). The distal spline portions (66) may be securably and non-slidingly disposed within said distal tip (16). The distal spline portions (66) may be securably and non-slidingly disposed within said distal tip (16) in a predetermined angular relationship, wherein angles (θ1-θ8) between said splines (14) at said distal tip (16) forming said predetermined angular relationship may be all substantially equal to each other; or wherein at least one angle (θ1-θ8) between said splines (14) at said distal tip (16) forming said predetermined angular relationship may be different from another angle (θ1-θ8) between said splines (14) at said distal tip (16). The splines (14) have distal end portions (67); and further wherein the distal spline end portions (67) may be securably and non-slidingly disposed within said distal tip (16). The splines (14) may approach said distal tip (16) at an angle (α) of less than about 45° as measured from the line segment between said proximal anchor (18) and said distal tip (16) along the longitudinal axis (L). The splines (14) may have a distal incurvate inward bend (78) between said distal tip (16) and said distal excurvate outward bends (80). The distal tip (16) may have a non-thrombogenic outer surface free of voids and slots that would permit the passage or entry of blood thereinto. The splines (14) may have reduced widths at said distal portions (66) near the tip (16) as compared to spline widths at said medial portions (64).

A system (10) for sensing multiple local electric voltages from endocardial surface of a heart, may comprise: a first elongate tubular member (20) having a lumen (20C), a proximal end (20A) and a distal end (20B); a basket assembly (12) comprising: a plurality of flexible splines (14) for guiding a plurality of exposed electrodes (186), the splines (14) having proximal portions (62), distal portions (66) and medial portions (64) therein between; a proximal anchor (18) for securably affixing the proximal portions (62) of the splines (14); said anchor (18) being secured at the distal end (20B) of the first elongate tubular member (20); a distal tip (16) for securably affixing the distal portions (66) of the splines (14), said proximal anchor (18) and said distal tip (16) defining a longitudinal axis (L) about which the splines (14) are disposed; wherein the splines (14) approach the distal tip (16) at an angle (α) of about 90° or less than about 90° as measured from a line segment between the proximal anchor (18) and the distal tip (16) along the longitudinal axis (L); wherein the splines (14) comprise a superelastic material such that the basket assembly (12) exhibits a substantially cylindrical shape when radially compressed and exhibits a radially expanded non-spherical shape when not radially compressed; and wherein each of the splines (14) in the radially expanded non-spherical shape contain a proximal recurve (76) in the proximate portion (62) of the spline (14) at a location near to the proximal anchor (18) of the basket assembly (12), the proximal recurve (76) comprises a proximal excurvate outward bend (84) and a proximal incurvate inward bend (82) between said proximal excurvate outward bend (84) and said proximal anchor (18), where an apex (83) of the proximal incurvate inward bend (82) is disposed in a direction toward the distal tip (16) and is further disposed inwardly closer toward the distal tip (16) than the proximal excurvate outward bend (84). The system (10) may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has said substantially cylindrical shape when compressed within the lumen (48) of the second elongate tubular member (46); and wherein the basket assembly (12) has said radially expanded non-spherical shape when not compressed within the lumen (48) of the second elongate tubular member (46) and disposed past the distal end (54) of the second elongate tubular member (46). The splines (14) may approach said distal tip (16) at an angle (α) of less than about 45° as measured from the line segment between said proximal anchor (18) and said distal tip (16) along the longitudinal axis (L). The splines (14) in the radially expanded non-spherical shape may contain a distal excurvate outward bend (80) disposed at the distal portion (66) of the spline (14) at a location near to the distal tip (16) of the basket assembly (12) to bend the splines (14) back towards the proximal anchor (18); wherein the splines (14) may have a distal incurvate inward bend (78) between said distal tip (16) and said distal excurvate outward bends (80); and wherein, when basket assembly (12) is in said radially expanded non-spherical shape, the splines (14) may extend beyond the distal tip (16) and, when basket assembly (12) is in said radially expanded non-spherical shape, apices (81) of the distal excurvate bends (80) may be disposed beyond the distal tip (16). The distal tip (16) may have a non-thrombogenic outer surface free of voids and slots that would permit the passage or entry of blood thereinto. The splines (14) may have reduced widths at said distal portions near the distal tip (16) as compared to spline widths at said medial portions (64). Each of the splines (14) have a length between said apex (83) of said proximal incurvate inward bend (82) and said proximal excurvate outward bend (84); and further wherein said length of at least one spline (14) may be different from said length of another of said splines (14). Alternatively, each of the splines (14) may have a substantially equal overall length between said proximal anchor (18) and said distal tip (16). Alternatively, each of the splines (14) may have a substantially equal overall length from said proximal anchor (18) and to said distal tip (16); and further wherein a length from said proximal excurvate outward bend (84) to said distal tip (16) for at least one of said splines (14) may be different from said length for another one of said splines (14).

A system (10) for sensing multiple local electric voltages from endocardial surface of a heart, may comprise: a first elongate tubular member (20) having a lumen (20C), a proximal end (20A) and a distal end (20B); a basket assembly (12) comprising: a plurality of flexible splines (14) for guiding a plurality of exposed electrodes (186), the splines (14) having proximal portions (62) and distal portions (66); a proximal anchor (18) for securably affixing the proximal portions (62) of the splines (14); said proximal anchor (18) being secured at the distal end (20B) of the first elongate tubular member (20); a distal tip (16) for securably affixing the distal portions (66) of the splines (14), said proximal anchor (18) and said distal tip (16) defining a longitudinal axis (L) about which the splines (14) are disposed; wherein the splines (14) approach the distal tip (16) at an angle (α) of less than about 45° as measured from a line segment between the proximal anchor (18) and the distal tip (16) along the longitudinal axis (L); wherein the splines (14)

comprise a superelastic material such that the basket assembly (12) exhibits a substantially cylindrical shape when radially compressed and exhibits a radially expanded non-spherical shape when not radially compressed; wherein the splines (14) in the radially expanded non-spherical shape contain a distal excurvate outward bend (80) disposed at the distal portion of the spline (14) at a location near to the distal tip (16) of the basket assembly (12) to bend the splines (14) back towards the proximal anchor (18); wherein the splines (14) have a distal incurvate inward bend (78) between said distal tip (16) and said distal excurvate outward bends (80); wherein, when basket assembly (12) is in said radially expanded non-spherical shape, the splines (14) extend beyond the distal tip (16) and, when basket assembly (12) is in said radially expanded non-spherical shape, apices (80) of the distal excurvate bends (80) are disposed beyond the distal tip (16); and wherein each of the splines (14) in the radially expanded non-spherical shape contain a proximal recurve (76) in the proximate portion (62) of the spline (14) at a location near to the proximal anchor (18) of the basket assembly (12), the proximal recurve (76) comprises a proximal excurvate outward bend (84) and a proximal incurvate inward bend (82) between said proximal excurvate outward bend (84) and said proximal anchor (18), where an apex (83) of the proximal incurvate inward bend (82) is disposed in a direction toward the distal tip (16) and is further disposed inwardly closer toward the distal tip (16) than the proximal excurvate outward bend (84). The system (10) may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has said substantially cylindrical shape when compressed within the lumen (48) of the second elongate tubular member (46); and wherein the basket assembly (12) has said radially expanded non-spherical shape when not compressed within the lumen (48) of the second elongate tubular member (46) and disposed past the distal end (54) of the second elongate tubular member (46). The distal spline portions (66) may be securably and non-slidingly disposed within said distal tip (16). The splines (14) may have distal end portions (67); and further wherein the distal spline end portions (67) may be securably and non-slidingly disposed within said distal tip (16). Each of the splines (14) may have a substantially equal overall length from said proximal anchor (18) and to said distal tip (16); and further wherein a length from said proximal excurvate outward bend (84) to said distal tip (16) is for at least one of said splines (14) is different from said length for another one of said splines (14).

A system (10) for sensing multiple local electric voltages from endocardial surface of a heart, may comprise: a first elongate tubular (20) member having a lumen (20C), a proximal end (20A) and a distal end (20B); a basket assembly (12) comprising: a plurality of flexible splines (14) for guiding a plurality of exposed electrodes (186), the splines (14) having proximal portions (62) and distal portions (66); a proximal anchor (18) for securably affixing the proximal portions (62) of the splines (14); said proximal anchor (18) being secured at the distal end (20B) of the first elongate tubular member (20); a distal tip (16) for securably affixing the distal portions (66) of the splines (14), said proximal anchor (18) and said tip (16) defining a longitudinal axis (L) about which the splines (14) are disposed; wherein the splines (14) comprise a superelastic material such that the basket assembly (12) exhibits a substantially cylindrical shape when radially compressed and exhibits a radially expanded non-spherical shape when not radially compressed; wherein each of the splines (14) in the radially expanded non-spherical shape contain a proximal recurve (76) in the proximate portion of the spline (14) at a location near to the anchor (18) of the basket assembly (12), the proximal recurve (76) comprises a proximal excurvate outward bend (84) and a proximal incurvate inward bend (82) between said proximal excurvate outward bend (84) and said proximal anchor (18), where an apex (83) of the proximal incurvate inward bend (82) is disposed in a direction toward the distal tip (16) and is further disposed inwardly closer toward the distal tip (16) than the proximal excurvate outward bend (84); and wherein the proximal incurvate inward bends (82) of some splines (14) have a different geometry from the proximal incurvate inward bends (82) of other splines (14); and wherein one or more tissue-contacting portions of the individual splines (14) are of unequal length with respect to each other, and each of the proximal incurvate inward bend portions (82) of the splines (14) possess compensating lengths such that the sum of the tissue facing portion plus proximal incurvate inward bend portion (82) of all splines (14) are substantially the same. The system (10) may further comprise: a second elongate tubular member (46) having a lumen (48), a proximal end (56) and a distal end (54); wherein the basket assembly (12) is slidingly compressible to fit within the lumen (48) of the second elongate tubular member (46); wherein the basket assembly (12) has said substantially cylindrical shape when compressed within the lumen (48) of the second elongate tubular member (46); and wherein the basket assembly (12) has said radially expanded non-spherical shape when not compressed within the lumen (48) of the second elongate tubular member (46) and disposed past the distal end (54) of the second elongate tubular member (46). The splines (14) may have distal end portions (67); and further wherein the distal spline end portions (67) may be securably and non-slidingly disposed within said distal tip (16). The splines (14) in the radially expanded non-spherical shape may contain a distal excurvate outward bend (80) disposed at the distal portion (66) of the spline (14) at a location near to the distal tip (16) of the basket assembly (12) to bend the splines (14) back towards the proximal anchor (18); wherein the splines (14) may have a distal incurvate inward bend (78) between said distal tip (16) and said distal excurvate outward bends (80); and wherein, when basket assembly (12) is in said radially expanded non-spherical shape, the splines (14) may extend beyond the distal tip (16) and, when basket assembly (12) is in said radially expanded non-spherical shape, apices (81) of the distal excurvate bends (80) are disposed beyond the distal tip (16).

Embodiments directed to spline assemblies for basket catheters include, but are not limited to, as follows:

A system (10) for sensing multiple local electric voltages from endocardial surface of a heart, may comprise: an elongate tubular member (20) having a lumen (20C), a proximal end (20A) and a distal end (20B); a plurality of flexible splines (14) having proximal portions (62), distal portions (66) and medial portions (64) therein between, wherein the splines (14) comprise an outer surface (190), an inner surface (192) and two side surfaces (194, 196); an anchor (18) for securably affixing the proximal portions (62) of the splines (14), wherein the anchor (18) is securably affixed within the lumen (20C) of the elongate tubular member (20) at the distal end (20B) of the elongate tubular member (20); a tip (16) for securably affixing the distal portions (66) of the splines (14); and a polymeric member (185) comprising opposed a first open end (202) and a second open end (200) defining an open lumen (208) therein between and an inner member surface (208B) and an outer member surface (208A), wherein at least one of the plurality of flexible splines (14) is at least partially disposed within the lumen (208) of said polymeric member; a flexible electrode assembly strip (188) with one or more exposed electrodes (186) disposed on at least a portion of the outer surface (208A) of said polymeric member (185); wherein the flexible electrode assembly strip (188) comprises: a polymeric substrate (236) having an inner surface (236B) and an opposed outer surface (236A); said one or more exposed electrodes (186) disposed over at least part of the outer surface (236A) of the polymeric substrate (236); and one or more electrical traces (228) disposed over at least a portion of the inner surface (236B) of the polymeric substrate (236) or over at least a portion of the outer surface (236A) of the polymeric substrate (236), said one or more electrical traces (228) being in electrical communication with said one or more exposed electrodes (186); wherein a portion of the flexible electrode assembly (188) transitions from the outer surface (208A) of said polymeric member (185) towards the inner surface (208B) of said polymeric member (185) prior to said anchor (18); and wherein another portion of the flexible electrode assembly (188) extends through at least a portion of said anchor (18) and into said lumen (20C) of said elongate tubular member (20). The system (10) may further comprise: a plurality of polymeric members (185) each comprising said flexible electrode assembly strip (188); wherein each of said plurality of flexible splines (14) are at least partially disposed within a different one of said plurality of polymeric members (185). The one or more electrical traces (228) may be disposed over at least a portion of the inner surface (236B) of the polymeric substrate (236) and may further comprise vias (230) to provide said electrical communication between said one or more electrical traces (228) and said one or more exposed electrodes (186). The one or more electrical traces (228) may be disposed over at least a portion of the outer surface (236A) of the polymeric substrate (236) and further comprising a polymeric covering (238, 240) over the outer surface (236A) of the polymeric substrate (236) and said electrical traces (228) with the one or more exposed electrodes (186) being substantially free of the polymeric covering (238, 240). The first opposed open end (202) of the polymeric member (185) may be secured to the distal spline portion (66) of said at least one of the plurality of flexible splines (14) at a position near to the distal tip (16) and the second opposed open end (200) of the polymeric member (185) may be secured to the proximal spline portion (62) of said at least one of the plurality of flexible splines (14) at a position near to the anchor (18). The first opposed open end (202) of the polymeric member (185) may be sealingly secured to the distal spline portion (66) at the position near to the distal tip (16) by a seal (206). Medial portions of the polymeric member (185) between said first opposed open end (202) and said second opposed open end (200) of the polymeric member (185) may not be secured to said medial portions (64) of said at least one of the plurality of flexible splines (14). At least one intermediate medial portion of the polymeric member (185) between said first opposed open end (202) and said second opposed open end (200) of the polymeric member (185) may be secured to at least one intermediate portion of said medial portions (64) of said at least one of the plurality of flexible splines (14). The one or more exposed electrodes (186) may comprise copper, gold, platinum, platinum black, platinum-iridium and combinations thereof. The outer surface (190) and the inner surface (192) of said plurality of flexible splines (14) may be substantially flat surfaces and the two side surfaces (194, 196) of said plurality of flexible splines (14) may be convexly rounded surfaces. The one or more exposed electrodes (186) may have a substantially flat upper surface.

A system (10) for sensing multiple local electric voltages from endocardial surface of a heart, may comprise: an elongate tubular member (20) having a lumen (20C), a proximal end (20A) and a distal end (20B); a plurality of flexible splines (14) having proximal portions (62), distal portions (66) and medial portions (64) therein between, wherein the splines (14) comprise an outer surface (190), an inner surface (192) and two side surfaces (194. 196); an anchor (18) for securably affixing the proximal portions (62) of the splines (14), wherein the anchor (18) is securably affixed within the lumen (20C) of the elongate tubular member (20) at the distal end (20B) of the elongate tubular member (20); a tip (16) for securably affixing the distal portions (66) of the splines (14); and a polymeric member (185) comprising opposed first (202) and second (200) open ends defining an open lumen (208) therein between and an inner member surface (208B) and an outer member surface (208A), wherein at least one of the plurality of flexible splines (14) is at least partially disposed within the lumen (208) of said polymeric member (185); a flexible electrode assembly strip (188) with one or more exposed electrodes (186) disposed on at least a portion of the outer surface (208A) of said polymeric member (185); wherein the flexible electrode assembly strip (188) comprises: a polymeric substrate (236) having an inner surface (236B) and an opposed outer surface (236A); said one or more exposed electrodes (186) disposed over at least part of the outer surface (236A) of the polymeric substrate (236); and one or more electrical traces (228) disposed over at least a portion of the inner surface (236B) of the polymeric substrate (236) or over at least a portion of the outer surface (236A) of the polymeric substrate (236), said one or more electrical traces (228) being in electrical communication with said one or more exposed electrodes (186); wherein the first opposed open end (202) of the polymeric member (185) is secured to the distal spline portion (66) of said at least one of the plurality of flexible splines (14) at a position near to the distal tip (16) and the second opposed open end (200) of the polymeric member (185) is secured to the proximal spline portion (62) of said at least one of the plurality of flexible splines (14) at a position near to the anchor (18); and wherein medial portions of the polymeric member (185) between said first opposed open end (202) and said second opposed open end (200) of the polymeric member (185) are not secured to said medial portions (64) of said at least one of the plurality of flexible splines (14). The system (10) may further comprise a seal (206) for sealingly engaging said first opposed open end (202) of the polymeric member (185) and said distal spline portion (66). A portion of the flexible electrode assembly (188) may extend through at least a portion of said anchor (18) and into said lumen (20C) of said elongate tubular member (20). The system (10) may further comprise: a plurality of polymeric members (185) each comprising said flexible electrode assembly strip (188); wherein each of said plurality of flexible splines (14) may be at least partially disposed within a different one of said plurality of polymeric members (185). The one or more electrical traces (228) may be disposed over at least a portion of the inner surface (236B) of the polymeric substrate (236) and may further comprise vias (230) to provide said electrical communication between said one or more electrical traces (228) and said one or more exposed electrodes (186).

The one or more electrical traces (228) may be disposed over at least a portion of the outer surface (236A) of the polymeric substrate (236) and may further comprise a polymeric covering (238, 240) over the outer surface (236A) of the polymeric substrate (236) and said electrical traces (228) with the one or more exposed electrodes (186) being substantially free of the polymeric covering (238, 240). The one or more exposed electrodes (186) may comprise copper, gold, platinum, platinum black, platinum-iridium and combinations thereof. The outer surface (190) and the inner surface (192) of said plurality of flexible splines (14) may be substantially flat surfaces and the two side surfaces (194, 196) of said plurality of flexible splines (14) may be convexly rounded surfaces. The one or more exposed electrodes (186) have a substantially flat upper surface.

A system (10) for sensing multiple local electric voltages from endocardial surface of a heart, may comprise: an elongate tubular member (20) having a lumen (20C), a proximal end (20A) and a distal end (20B); a plurality of flexible splines (14) having proximal portions (62), distal portions (66) and medial portions (64) therein between, wherein the splines (14) comprise an outer surface (190), an inner surface (192) and two side surfaces (194, 196), wherein said inner and outer spline surfaces (190, 192) have a substantially flat portion with the substantially flat portions being parallel to one and the other, and further wherein the two side spline surfaces (194, 196) are convexly rounded to define a rounded-rectangular shape; an anchor (18) for securably affixing the proximal portions (62) of the splines (14), wherein the anchor (18) is securably affixed within the lumen (20C) of the elongate tubular member (20) at the distal end (20B) of the elongate tubular member (20); a tip (16) for securably affixing the distal portions (66) of the splines (14); and a plurality of polymeric members (185) each having opposed first (202) and second (200) open ends defining an open lumen (208) therein between, wherein the polymeric members (185) comprise an outer surface (208A), an inner surface (208B) and two side surfaces where a cross-sectional profile of the polymeric members is elliptical to match a cross-sectional profile of the rounded-rectangular shape of the splines (14) and is slightly larger than the cross-sectional profile of the rounded-rectangular shape of the splines (14) and wherein each of the plurality of flexible splines (14) is at least partially disposed within the lumen (208) of a different one of said plurality of polymeric members (185); a flexible electrode assembly strip (188) with one or more exposed electrodes (186) disposed on at least a portion of the outer surface (208A) of said polymeric members (185); wherein the flexible electrode assembly strip (188) comprises: a polymeric substrate (236) having an inner surface (236B) and an opposed outer (236A) surface; said one or more exposed electrodes (186) disposed over at least part of the outer surface (236A) of the polymeric substrate (236); and one or more electrical traces (228) disposed over at least a portion of the inner surface (236B) of the polymeric substrate (236) or over at least a portion of the outer surface (236A) of the polymeric substrate (236), said one or more electrical traces (228) being in electrical communication with said one or more exposed electrodes (186); wherein a portion of said flexible electrode assembly strip (188) extends through at least a portion of said anchor (18) and into said lumen (20C) of said elongate tubular member (20). The one or more electrical traces (228) may be disposed over at least a portion of the inner surface (236B) of the polymeric substrate (236) and may further comprise vias (230) to provide said electrical communication between said one or more electrical traces (228) and said one or more exposed electrodes (186). The one or more electrical traces (228) may be disposed over at least a portion of the outer surface (236A) of the polymeric substrate (236) and may further comprise a polymeric covering (238, 240) over the outer surface (236A) of the polymeric substrate (236) and said electrical traces (228) with the one or more exposed electrodes (186) being substantially free of the polymeric covering (238, 240). The first opposed open end (202) of the polymeric member (185) may be sealingly secured to the distal spline portion (66) of said at least one of the plurality of flexible splines (14) at a position near to the distal tip (16) and the second opposed open end (200) of the polymeric member (185) may be secured to the proximal spline portion (62) of said at least one of the plurality of flexible splines (14) at a position near to the anchor (18). Medial portions of the polymeric member between said first opposed open end (202) and said second opposed open end (200) of the polymeric member (185) may not be secured to said medial portions (64) of said at least one of the plurality of flexible splines (14). At least one intermediate medial portion of the polymeric member (185) between said first opposed open end (202) and said second opposed open end (200) of the polymeric member (185) may be secured to at least one intermediate portion of said medial portions (64) of said at least one of the plurality of flexible splines (14). The one or more exposed electrodes (186) may comprise copper, gold, platinum, platinum black, platinum-iridium and combinations thereof. The one or more exposed electrodes (186) may have a substantially flat upper surface.

A system (10) for sensing multiple local electric voltages from endocardial surface of a heart, may comprise: an elongate tubular member (20) having a lumen (20C), a proximal end (20A) and a distal end (20B); a plurality of flexible splines (14) having proximal portions (62), distal portions (66) and medial portions (64) therein between, wherein the splines (14) comprise an outer surface (190), an inner surface (192) and two side surfaces (194, 196); an anchor (18) for securably affixing the proximal portions (62) of the splines (14), wherein the anchor (18) is securably affixed within the lumen (20C) of the elongate tubular member (20) at the distal end (20B) of the elongate tubular member (20); a tip (16) for securably affixing the distal portions (66) of the splines (14); and a plurality of polymeric members (185) each having opposed first (202) and second (200) open ends defining an open lumen (208) therein between and an outer surface (208A) and an inner surface (208B), wherein each of the plurality of flexible splines (14) is at least partially disposed within the lumen (208) of a different one of said plurality of polymeric members (185); a flexible electrode assembly strip (188) with one or more exposed electrodes (186) disposed on at least a portion of the outer surface (208A) of said polymeric members (185); wherein the flexible electrode assembly strip (188) comprises: a polymeric substrate (236) having an inner surface (236B) and an opposed outer surface (236A); said one or more exposed electrodes (186) disposed over at least part of the outer surface (236A) of the polymeric substrate (236); and one or more electrical traces (228) disposed over at least a portion of the inner surface (236B) of the polymeric substrate (236) or over at least a portion of the outer surface (236A) of the polymeric substrate (236), said one or more electrical traces (228) being in electrical communication with said one or more exposed electrodes (186); wherein the flexible electrode assembly strip (188) is compressed into the outer surface (208A) of the polymeric member (185); and wherein the flexible electrode assembly strip (188) is thermally or adhesively bonded to the outer surface (208A) of the polymeric member (185).

Embodiments directed to flex circuits and flexible electrode assemblies include, but are not limited to, as follows:

A device for insertion into a body lumen, may comprise: an electrode assembly strip (188) with exposed electrodes (186) comprising: a polymeric substrate (236) having an upper surface (236A) and an opposed lower surface (236B); one or more electrodes (186) disposed over a portion of the upper surface (236A) of the polymeric substrate (236); one or more electrical traces (228) disposed over a portion of the lower surface (236B) of the polymeric substrate (236) in electrical communication with the one or more electrodes (186) by way of metal plated holes (230) through the substrate (236); and a flexible polymeric substrate (246) having a substrate surface (246A) and a substrate wall (246C); wherein the electrode assembly strip (188) is compressingly and thermally bonded to the substrate surface (246A) of the flexible polymeric substrate (246) to define a flexible electrode assembly strip (247); and wherein the electrode assembly strip (188) has a thickness from about 0.0005 inches to about 0.008 inches. The electrode assembly strip (188) may have a thickness from about 0.002 inches to about 0.004 inches. The device may further comprise: a first polymeric covering (238) disposed portions of the substrate surface (236A) of the polymeric substrate (236) not having the one or more electrodes (186) thereon, said first polymeric covering (238) having holes disposed over the one or more electrodes (186) thereby defining one or more exposed electrodes (186); and a second polymeric covering (240) disposed over the one or more electrical traces (228) and portions of the lower surface (236B) of the substrate (236) not having the one or more electrical traces (228) thereon. The polymeric substrate (236), the first polymeric covering (238) and the second polymeric covering (240) may comprise a biocompatible polyimide material. The flexible polymeric substrate (236) may comprise a biocompatible polyether block amide material. The flexible polymeric substrate (236) may comprise a biocompatible polymer selected from the group consisting of polyesters, silicones, silicone rubbers, urethanes and combinations thereof. The flexible polymeric substrate (236) may be a sheet. Alternatively, the flexible polymeric substrate (236) may be an extruded tube having an open lumen.

A device for insertion into a body lumen, may comprise: an electrode assembly strip (188) with exposed electrodes (186) comprising: a polymeric substrate (236) having an upper surface (236A) and an opposed lower surface (236B); at least two electrodes (186) disposed over a portion of the upper surface (236A) of the polymeric substrate (236); at least two electrical traces (228) disposed over a portion of the lower surface (236B) of the polymeric substrate (236) in electrical communication with the at least two electrodes by way of metal plated holes (230) through the substrate (236); a first polymeric covering (238) disposed portions of the upper surface (236A) of the polymeric substrate (236) not having the at least two of said electrodes (186) thereon, said first polymeric covering (238) having holes disposed over the at least two of said electrodes (186) thereby defining at least two exposed electrodes (186); a second polymeric covering (240) disposed over the at least two of the electrical traces (228) and portions of the lower surface of the substrate not having the at least two electrical traces (228) thereon; a first flexible polymeric tube (185) having opposed open ends (200, 202) defining an open lumen (208) therein between and an inner tubular surface (208B) and an outer tubular surface (208A); wherein the electrode assembly strip (188) is disposed over the outer surface (208A) of the first flexible polymeric tube (185); and a second flexible polymeric tube (185) having opposed open ends (200, 202) defining an open lumen (208) therein between and an inner tubular surface (208B) and an outer tubular surface (208A), wherein the second flexible polymeric tube (185) is disposed over portions of the electrode assembly strip (188) not having the exposed electrodes (186); wherein the electrode assembly strip (188), the first flexible polymeric tube (185) and the second flexible polymeric tube (185) are compressingly and thermally bonded to each other to define a flexible electrode assembly strip (247); and wherein the electrode assembly strip (188) has a thickness from about 0.0005 inches to about 0.008 inches. The polymeric substrate (236), the first polymeric covering (238) and the second polymeric covering (240) may comprise a biocompatible polyimide material. The first and second flexible polymeric tubes (185) may comprise a polyether block amide material. The first flexible polymeric tube (185) may be an extruded tube. The flexible electrode assembly strip (247) may have a substantially smooth and atraumatic overall outer surface (246A). The device may further comprise: an elongate tubular member (20) having a lumen (20C), a proximal end (20A) and a distal end (20B); a plurality of flexible splines (14) having proximal portions (62), distal portions (66) and medial portions (64) therein between, wherein the splines (14) comprise an outer surface (190), an inner surface (192) and two side surfaces (194, 196); an anchor (18) for securably affixing the proximal portions (62) of the splines (14), wherein the anchor (18) is securably affixed within the lumen (20C) of the elongate tubular member (20) at the distal end (20B) of the elongate tubular member (20); and a tip (16) for securably affixing the distal portions (66) of the splines (14); wherein the flexible electrode assembly strip (247) is disposed over at least one of the plurality of splines (14). The device may further comprise a plurality of flexible electrode assembly strips (247), wherein each of said plurality of splines (14) has at least one of said plurality of flexible electrode assembly strips (247) disposed there over.

A device for insertion into a body lumen, may comprise: an electrode assembly strip (188) with exposed electrodes (186) comprising: a polymeric substrate (236) having an upper surface (236A) and an opposed lower surface (236B); one or more substantially flat electrodes (186) disposed over a portion of the upper surface (236A) of the polymeric substrate (236); one or more of electrical traces (228) disposed over a portion of the lower surface (236B) of the polymeric substrate (236) in electrical communication with the one or more electrodes (186) by way of metal plated holes (230) through the substrate (236); a first polymeric covering (238) disposed portions of the upper surface (236A) of the polymeric substrate (236) not having the one or more of the electrodes (186) thereon, said first polymeric covering (238) having holes disposed over the one or more electrodes (186) thereby defining one or more exposed electrodes (186); a second polymeric covering (240) disposed over the over the one or more electrical traces (228) and portions of the lower surface (236B) of the substrate (236) not having the one or more electrical traces (228) thereon; and a flexible polymeric tube (185) having opposed open ends (200, 202) defining an open lumen (208) therein between and an inner tubular surface (208B) and an outer tubular surface (208A) defining a tubular wall (210) therein between; wherein the electrode assembly strip (188) is compressingly and thermally bonded to the outer surface (208A) of the flexible polymeric tube (185) to define a flexible electrode assembly strip (247); wherein substantial portions of the substantially flat electrodes (186) remain substantially flat to provide substantially flat exposed electrodes (186); and wherein the electrode assembly strip (188) has a thickness from 0.0005 inches to about 0.008 inches. The polymeric substrate (236) may comprise a polyimide material. The first polymeric covering (238) and the second polymeric covering (240) may comprise a polyimide material. The flexible polymeric tube (185) may comprise a polyether block amide material. The flexible polymeric tube (185) may be an extruded tube. The electrode assembly strip (188) may be compressed into the tubular wall (210) of the flexible polymeric tube (185) to provide a substantially smooth and atraumatic overall outer surface for the flexible electrode assembly strip. The device may further comprise: an elongate tubular member (20) having a lumen (20C), a proximal end (20A) and a distal end (20B); one or more flexible splines (14) having proximal portions (62), distal portions (66) and medial portions (64) therein between, wherein the one or more splines (14) comprise an outer surface (190), an inner surface (192) and two side surfaces (194, 196); an anchor (18) for securably affixing the proximal portions (62) of the one or more splines (14), wherein the anchor (18) is securably affixed within the lumen (20C) of the elongate tubular member (20) at the distal end (20B) of the elongate tubular member (20); and a tip (16) for securably affixing the distal portions (66) of the one or more splines (14); wherein the flexible electrode assembly strip (247) is disposed over at least one of the one or more splines (14). The device may further comprise one or more of flexible electrode assembly strips (247), wherein each of said one or more of the splines (14) may have at least one of said one or more of the flexible electrode assembly strips (247) disposed there over.

A device for insertion into a body lumen, may comprise an electrode assembly strip (188) with exposed electrodes (186) comprising: a polymeric substrate (236) having an upper surface (236A) and an opposed lower surface (236B); at least two substantially flat electrodes (186) disposed over a portion of the upper surface (236A) of the polymeric substrate (236); at least two electrical traces (228) disposed over a portion of the lower surface (236B) of the polymeric substrate (236) in electrical communication with the at least two electrodes (186) by way of metal plated holes (230) through the substrate (236); a first polymeric covering (238) disposed portions of the upper surface (236A) of the polymeric substrate (236) not having the at least two of said electrodes (186) thereon, said first polymeric covering (238) having holes disposed over the at least two of said electrodes (186) thereby defining at least two exposed electrodes (186); a second polymeric covering (240) disposed over the over the plurality of electrical traces (228) and portions of the lower surface (236B) of the substrate (236) not having electrical traces (228) thereon; a first flexible polymeric tube (185) having opposed open ends (200, 202) defining an open lumen (208) therein between and an inner tubular surface (208B) and an outer tubular surface (208A); wherein the electrode assembly strip (188) is disposed over the outer surface (208A) of the first flexible polymeric tube (185); and a second flexible polymeric tube (185) having opposed open ends (200, 202) defining an open lumen (208) therein between and an inner tubular surface (208B) and an outer tubular surface (208A), wherein the second flexible polymeric tube (185) is disposed over portions of the electrode assembly strip (188) not having the exposed electrodes (186), wherein the electrode assembly strip (186), the first flexible polymeric tube (185) and the second flexible polymeric tube (185) are compres singly and thermally bonded to each other to define a flexible electrode assembly strip (247); wherein substantial portions of the at least two substantially flat electrodes (186) remain substantially flat to provide at least two substantially flat exposed electrodes (186); and wherein the electrode assembly strip (188) has a thickness from about 0.0005 inches to about 0.008 inches. The polymeric substrate (236) may comprise a polyimide material. The first polymeric covering (238) and the second polymeric covering (240) may comprise a polyimide material. The first and second flexible polymeric tubes (185) may comprise a polyether block amide material. The first flexible polymeric tube (185) may be an extruded tube. The flexible electrode assembly strip (247) may have a substantially smooth and atraumatic overall outer surface. The device may further comprise: an elongate tubular member (20) having a lumen (20C), a proximal end (20A) and a distal end (20B); one or more flexible splines (14) having proximal portions (62), distal portions (66) and medial portions (64) therein between, wherein the splines (14) comprise an outer surface (190), an inner surface (192) and two side surfaces (194, 196); an anchor (18) for securably affixing the proximal portions (62) of the splines (14), wherein the anchor (18) is securably affixed within the lumen (20C) of the elongate tubular member (20) at the distal end (20B) of the elongate tubular member (20); and a tip (16) for securably affixing the distal portions (66) of the one or more splines (14); wherein the flexible electrode assembly strip (247) is disposed over at least one of the one or more of the splines (14).

Embodiments directed to methods for sensing multiple local electric voltages from endocardial surface of a heart include, but are not limited to, as follows:

A method for sensing multiple local electric voltages from endocardial surface of a heart, may comprise: providing a system (10) for sensing multiple local electric voltages from endocardial surface of a heart, comprising: a first elongate tubular member (20) having a lumen (20C), a proximal end (20A) and a distal end (20B); a basket assembly (12) comprising: a plurality of flexible splines (14) for guiding a plurality of exposed electrodes (186), the splines (14) having proximal portions (62), distal portions (66) and medial portions (64) therein between, wherein the electrodes (186) are substantially flat electrodes and are substantially unidirectionally oriented towards a direction outside of the basket assembly (12); a proximal anchor (18) for securably affixing the proximal portions (62) of the splines (14); said anchor (18) being secured at the distal end (20B) of the first elongate tubular member (20); a distal tip (16) for securably affixing the distal portions (66) of the splines (14), said proximal anchor (18) and said distal tip (16) defining a longitudinal axis (L) about which the splines (14) are disposed; wherein the splines (14) approach the distal tip (16) at an angle ($\alpha$) of about 90° or less than about 90° as measured from a line segment between the proximal anchor (18) and the distal tip (16) along the longitudinal axis (L); wherein the splines (14) comprise a superelastic material such that the basket assembly (12) exhibits a substantially cylindrical shape when radially compressed and exhibits a radially expanded non-spherical shape when not radially compressed; and wherein each of the splines (14) in the radially expanded non-spherical shape contain a proximal recurve (76) in the proximate portion (62) of the spline (14) at a location near to the proximal anchor (18) of the basket assembly (12), the proximal recurve (76) comprises a proximal excurvate outward bend (84) and a proximal incurvate inward bend (82) between said proximal excurvate outward bend (84) and said proximal anchor (18), where an apex (83)

of the proximal incurvate inward bend (82) is disposed in a direction toward the distal tip (16) and is further disposed inwardly closer toward the distal tip (16) than the proximal excurvate outward bend (84); delivering the system (10) to the heart so that the basket assembly (12) is disposed within the right atrium of the heart; contacting proximal atrial tissue with the electrodes (186) disposed on the proximal spline portions (62) to detect multiple local electric voltages from endocardial surface thereat; and contacting atrial tissue with the electrodes (186) disposed on the medial spline portions (64) and the distal spline portions (66) to detect multiple local electric voltages from endocardial surface thereat. The splines (14) of the basket assembly (12) may be flexible to match the contours of the right atrium. Substantially all of the electrodes (186) may contact atrial tissue. Substantially all of the electrodes (186) may remain substantially spatially fixed with respect to atrial tissue. A substantial portion of atrial signals detected by the system (10) may have larger amplitudes than ventricular signals detected by the system (10). The splines (14) in the radially expanded non-spherical shape may contain a distal excurvate outward bend (80) disposed at the distal portion (66) of the spline (14) at a location near to the distal tip (16) of the basket assembly (12) to bend the splines (14) back towards the proximal anchor (18); and wherein the splines (14) have a distal incurvate inward bend (78) between said distal tip (16) and said distal excurvate outward bends (80). The splines (14) of the basket assembly (12) may be flexible to match the contours of the right atrium.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

What is claimed is:

1. A system for sensing multiple local electric voltages from endocardial surface of a heart, comprising:
    a first elongate tubular member having a lumen, a proximal end and a distal end;
    a basket assembly comprising:
        a plurality of exposed electrodes;
        a plurality of flexible splines for guiding the plurality of exposed electrodes, said plurality of flexible splines having proximal spline portions, distal spline portions and medial spline portions therein between, wherein the splines comprise an outer surface, an inner surface and two side surfaces, and wherein the splines further comprise alignment members projecting laterally outwardly from the two side surfaces at the distal spline portions;
    a proximal anchor for securably affixing the proximal spline portions, wherein the proximal anchor is securably affixed within the lumen of the first elongate tubular member at the distal end of the first elongate tubular member; and
    a distal tip comprising a top part and an opposed bottom part;
        said top part comprising an atraumatic top surface and an opposed bottom surface;
        said opposed bottom surface of said top part comprising a plurality of spline alignment posts disposed therefrom defining a lateral portion of said distal tip, wherein adjacent pairs of the spline alignment posts define spline channels there between, wherein interior portions of the spline alignment posts are spaced apart to define a spline alignment portion, and wherein the alignment members of the splines are securably disposed within the spline alignment portion of the top part;
        said opposed bottom part comprising an atraumatic bottom surface and an opposed upper surface;
        said opposed upper surface of said bottom part comprising a raised central portion configured to fit within the spline alignment portion of the top part;
    wherein the splines have reduced lateral extents between the two side surfaces to define reduced spline widths at said distal spline portions near the distal tip and proximal to the alignment members as compared to spline widths at said medial spline portions;
    wherein spacing between adjacent pairs of the spline alignment posts is greater than the reduced spline widths and less than lateral extents between the two side surfaces at said medial spline portions;
    wherein the spacing between adjacent pairs of the spline alignment posts is less than lateral extents of the laterally projecting alignment members at the distal portions of the splines;
    wherein the basket assembly has a radially expanded non-cylindrical shape; and
    wherein the splines comprise a superelastic material.

2. The system of claim 1, further comprising:
    a second elongate tubular member having a lumen, a proximal end and a distal end, the second elongate tubular member being slidably disposed over the first elongate tubular member;
    wherein the basket assembly is slidingly compressible to fit within the lumen of the second elongate tubular member;
    wherein the basket assembly has a substantially cylindrical shape when compressed within the lumen of the second elongate tubular member; and
    wherein the basket assembly has said radially expanded non-cylindrical shape when not compressed within the lumen of the second elongate tubular member and disposed past the distal end of the second elongate tubular member.

3. The system of claim 1, wherein each spline channel of the distal tip contains only one distal spline portion.

4. The system of claim 1, wherein each spline channel extends from the bottom surface of the top part of the distal tip to the upper surface of the bottom part of the distal tip.

5. The system of claim 1, wherein, when said basket assembly is in said radially expanded non-cylindrical shape, the splines extend beyond the distal tip and comprise excurvate bends beyond the distal tip to bend the splines back towards the proximal anchor.

6. The system of claim 1, wherein the splines approach the distal tip at an angle of about 90° as measured from a line segment between the proximal anchor and the distal tip along the longitudinal axis.

7. The system of claim 1, wherein the splines further comprise spline ends and further wherein the spline ends terminate at the proximal portions of the splines.

8. The system of claim 1, wherein said distal tip is a metallic distal tip.

9. The system of claim 8, wherein the top part of the distal tip and the opposed bottom part of the distal tip are welded together to secure the distal spline portions within the distal tip.

10. The system of claim 1, wherein the atraumatic top surface of the top part of the distal tip is domed shaped.

11. The system of claim 1, further comprising an elastomeric material disposed within the distal tip to minimize tip voids and open spaces at the distal tip.

12. The system of claim 1, wherein the superelastic material of the splines comprises nitinol.

13. The system of claim 1, wherein the superelastic material of the splines comprises a shape memory material.

14. A method for assembling a system for sensing multiple local electric voltages from endocardial surface of a heart, comprising:
providing a first elongate tubular member having a lumen, a proximal end and a distal end;
providing a plurality of exposed electrodes;
providing a plurality of flexible splines for guiding the plurality of exposed electrodes, said plurality of flexible splines having proximal spline portions, distal spline portions and medial spline portions therein between, wherein the splines comprise an outer surface, an inner surface and two side surfaces, and wherein the splines further comprise alignment members projecting laterally outwardly from the two side surfaces at the distal spline portions;
providing a proximal anchor for securably affixing the proximal portions of the splines, wherein the proximal anchor is securably affixable within the lumen of the first elongate tubular member at the distal end of the first elongate tubular member; and
providing a distal tip comprising a top part and an opposed bottom part;
said top part comprising an atraumatic top surface and an opposed bottom surface;
said opposed bottom surface of said top part comprising a plurality of spline alignment posts disposed therefrom defining a lateral portion of said distal tip, wherein adjacent pairs of the spline alignment posts define spline channels there between, wherein interior portions of the spline alignment posts are spaced apart to define a spline alignment portion, and wherein the alignment members of the splines are securably disposed within the spline alignment portion of the top part;
said bottom part comprising an atraumatic bottom surface and an opposed upper surface;
said opposed upper surface of said bottom part comprising a raised central portion configured to fit within the spline alignment portion of the top part;
wherein the splines have reduced lateral extents between the two side surfaces to define reduced spline widths at said distal spline portions near the distal tip and proximal to the alignment members as compared to spline widths at said medial spline portions;
wherein spacing between adjacent pairs of the spline alignment posts is greater than the reduced spline widths and less than lateral extents between the two side surfaces at said medial spline portions;
wherein the spacing between adjacent pairs of the spline alignment posts is less than lateral extents of the laterally projecting alignment members at the distal portions of the splines;
disposing the splines within the top part so that the alignment members of the splines are disposed within the spline alignment portion of the top part and so that the reduced spline widths at the distal spline portions are disposed within the spline channels;
aligning the top part and the bottom part to dispose the raised central portion of the upper surface of the bottom part into the spline alignment portion of the top part; and
securing the top part and bottom part to one and the other.

15. The method of claim 14, wherein each spline channel of the distal tip contains only one distal spline portion.

16. The method of claim 14, wherein each spline channel extends from the bottom surface of the top part of the distal tip to the upper surface of the bottom part of the distal tip.

17. The method of claim 14, wherein top part of the distal tip and the bottom part of the distal tip are metallic members.

18. The method of claim 17, wherein the step of securing the top part and bottom part to one and the other further comprises welding the top part and bottom part to one and the other.

19. The method of claim 14, further comprising:
securably affixing the proximal portions of the splines at the proximal anchor to form a basket assembly; and
securably affixing the proximal anchor within the lumen of the first elongate tubular member at the distal end of the first elongate tubular member.

\* \* \* \* \*